US012643943B2

(12) United States Patent
Nishihara et al.

(10) Patent No.: US 12,643,943 B2
(45) Date of Patent: Jun. 2, 2026

(54) ANTI-GDF15 ANTIBODY

(71) Applicant: OTSUKA PHARMACEUTICAL CO., LTD., Tokyo (JP)

(72) Inventors: Shigeki Nishihara, Osaka (JP); Yuichi Ishikawa, Osaka (JP); Yuichiro Nakaishi, Osaka (JP); Tatsuya Kawato, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 977 days.

(21) Appl. No.: 17/782,456

(22) PCT Filed: Dec. 3, 2020

(86) PCT No.: PCT/JP2020/045062
§ 371 (c)(1),
(2) Date: Jun. 3, 2022

(87) PCT Pub. No.: WO2021/112185
PCT Pub. Date: Jun. 10, 2021

(65) Prior Publication Data
US 2023/0036655 A1 Feb. 2, 2023

(30) Foreign Application Priority Data
Dec. 6, 2019 (WO) .................. PCT/JP2019/047956

(51) Int. Cl.
*C07K 16/22* (2006.01)
*A61P 35/00* (2006.01)
(Continued)

(52) U.S. Cl.
CPC .............. *C07K 16/22* (2013.01); *A61P 35/00* (2018.01); *C07K 16/24* (2013.01); *C12N 15/74* (2013.01);
(Continued)

(58) Field of Classification Search
CPC .. C07K 16/22; C07K 16/24; C07K 2317/565; C07K 2317/92; A61P 35/00; C12N 15/74; C12N 15/81; A61K 2039/505
See application file for complete search history.

(56) References Cited

U.S. PATENT DOCUMENTS

| | | | |
|---|---|---|---|
| 5,225,539 A | 7/1993 | Winter | |
| 5,530,101 A | 6/1996 | Queen et al. | |

(Continued)

FOREIGN PATENT DOCUMENTS

| | | |
|---|---|---|
| JP | H01-59878 B2 | 12/1989 |
| JP | 2016-508984 A | 3/2016 |

(Continued)

OTHER PUBLICATIONS

Hummer AM, Abanades B, Deane CM. Advances in computational structure-based antibody design. Curr Opin Struct Biol. 2022;74: 102379. (Year: 2022).*

(Continued)

*Primary Examiner* — Joanne Hama
*Assistant Examiner* — Hannah Sunshine
(74) *Attorney, Agent, or Firm* — Sughrue Mion, PLLC

(57) ABSTRACT
The present disclosure includes an anti-hGDF15 antibody that binds to an epitope of hGDF15 comprising the amino acid sequence of DHCPLGPGRCCRLH (SEQ ID NO: 3) and uses thereof.

15 Claims, 15 Drawing Sheets
Specification includes a Sequence Listing.

(51) Int. Cl.
| | |
|---|---|
| *C07K 16/24* | (2006.01) |
| *C12N 15/74* | (2006.01) |
| *C12N 15/81* | (2006.01) |
| *A61K 39/00* | (2006.01) |

(52) U.S. Cl.
CPC ........ *C12N 15/81* (2013.01); *A61K 2039/505* (2013.01); *C07K 2317/565* (2013.01); *C07K 2317/92* (2013.01)

(56) References Cited

U.S. PATENT DOCUMENTS

| | | | |
|---|---|---|---|
| 5,565,332 A | 10/1996 | Hoogenboom et al. | |
| 5,585,089 A | 12/1996 | Queen et al. | |
| 5,693,761 A | 12/1997 | Queen et al. | |
| 5,693,762 A | 12/1997 | Queen et al. | |
| 5,859,205 A | 1/1999 | Adair et al. | |
| 6,054,297 A | 4/2000 | Carter et al. | |
| 6,180,370 B1 | 1/2001 | Queen et al. | |
| 6,982,321 B2 | 1/2006 | Winter | |
| 7,022,500 B1 | 4/2006 | Queen et al. | |
| 9,738,723 B2 * | 8/2017 | Hammond ......... | C07K 16/2878 |
| 2011/0262444 A1 | 10/2011 | Kim | |

FOREIGN PATENT DOCUMENTS

| | | |
|---|---|---|
| JP | 2018-019690 A | 2/2018 |
| JP | 2019-521647 A | 8/2019 |
| WO | 2005/099746 A1 | 10/2005 |
| WO | 2014/049087 A1 | 4/2014 |
| WO | 2014/100689 A1 | 6/2014 |
| WO | 2016/049470 A1 | 3/2016 |
| WO | 2017/055613 A2 | 4/2017 |
| WO | 2017/172260 A8 | 10/2017 |
| WO | 2017/189724 A1 | 11/2017 |
| WO | 2022/101263 A1 | 5/2022 |

OTHER PUBLICATIONS

Koenig P, Lee CV, Walters BT, et al. Mutational landscape of antibody variable domains reveals a switch modulating the interdomain conformational dynamics and antigen binding. Proc Natl Acad Sci U S A. 2017;114(4):E486-E495. (Year: 2017).*

Rabia LA, Desai AA, Jhajj HS, Tessier PM. Understanding and overcoming trade-offs between antibody affinity, specificity, stability and solubility. Biochem Eng J. Sep. 15, 2018;137:365-374. (Year: 2019).*

Wischhusen, et al., "Growth/Differentiation Factor-15 (GDF-15): From Biomarker to Novel Targetable Immune Checkpoint", Frontiers in Immunology, vol. 11, Article 951, May 19, 2020, XP055758674 (21 pages).

Wang, et al., "GDF15: emerging biology and therapeutic applications for obesity and cardiometabolic disease", Nature Reviews, Endocrinology, Nature Publ. Group, US, vol. 17, No. 10, Aug. 11, 2021, pp. 592-607, XP037559962 (16 pages).

Extended European Search Report dated Nov. 24, 2023 in European Application No. 20895663.1.

Vicky W.W. Tsai et al., "The MIC-1/GDF15-GFRAL Pathway in Energy Homeostasis: Implications for Obesity, Cachexia, and Other Associated Diseases", Cell Metabolism, 2018, vol. 28, pp. 353-368 (16 pages total).

Asne R. Bauskin et al., "Role of Macrophage Inhibitory Cytokine-1 in Tumorigenesis and Diagnosis of Cancer", Cancer Res, 2006, vol. 66, No. 10, pp. 4983-4986 (4 pages total).

Jasper J. Haringman et al., "A Randomized Controlled Trial With an Anti-CCL2 (Anti-Monocyte Chemotactic Protein 1) Monoclonal Antibody in Patients With Rheumatoid Arthritis", Arthritis & Rheumatism, 2006, vol. 54, No. 8, pp. 2387-2392 (6 pages total).

William J. Evans et al., "Cachexia: A new definition", Clinical Nutrition, 2008, vol. 27, pp. 793-799 (7 pages total).

Vicky W.W. Tsai et al., "Anorexia /cachexia of chronic diseases: a role for the TGF-β family cytokine MIC-1/GDF15", J Cachexia Sarcopenia Muscle, 2012, vol. 3, pp. 239-243 (5 pages total).

Heiko Johnen et al., "Tumor-induced anorexia and weight loss are mediated by the TGF-β superfamily cytokine MIC-1", Nature Medicine, 2007, vol. 13, No. 11, pp. 1333-1340 (8 pages total).

Linda Yang et al., "GFRAL is the receptor for GDF15 and is required for the anti-obesity effects of the ligand", Nature Medicine, 2017, vol. 23, No. 10, pp. 1158-1166 (16 pages total).

Paul J. Emmerson et al., "The metabolic effects of GDF15 are mediated by the orphan receptor GFRAL", Nature Medicine, 2017, vol. 23, No. 10, pp. 1215-1219 (9 pages total).

Jer-Yuan Hsu et al., "Non-homeostatic body weight regulation through a brainstem-restricted receptor for GDF15", Nature, 2017, vol. 550, pp. 255-259 (23 pages total).

International Search Report dated Feb. 9, 2021 in International Application No. PCT/JP2020/045062.

International Search Report dated Feb. 18, 2020 in International Application No. PCT/JP2019/047956.

Asne R. Bauskin, et al., "The Propeptide Mediates Formation of Stromal Stores of PROMIC-1: Role in Determining Prostate Cancer Outcome", Cancer Res 2005, Mar. 15, 2005, vol. 65, No. 6, pp. 2330-2336 (7 pages total).

Noriaki Takeda, et al., "Pica in Rats Is Analogous to Emesis: An Animal Model in Emesis Research", Pharmacology Biochemistry and Behavior, 1993, vol. 45, pp. 817-821 (5 pages total).

Ivana Dostálová, et al. "Association of macrophage inhibitory cytokine-1 with nutritional status, body composition and bone mineral density in patients with anorexia nervosa: the influence of partial realimentation", Nutrition & Metabolism, 2010, vol. 7, No. 34, pp. 1-9 (9 pages total).

J L Balligand, et al., "Hypoleptinemia in patients with anorexia nervosa: loss of circadian rhythm and unresponsiveness to short-term refeeding", European Journal of Endocrinology, 1998, vol. 138, pp. 415-420 (6 pages total).

Danna M. Breen, et al., "GDF-15 Neutralization Alleviates Platinum-Based Chemotherapy-Induced Emesis, Anorexia, and Weight Loss in Mice and Nonhuman Primates", Cell Metabolism, Dec. 1, 2020, vol. 32, pp. 938-950 (20 pages total).

Marlena S. Fejzo, et al., "Placenta and appetite genes *GDF15* and *IGFBP7* are associated with hyperemesis gravidarum", Nature Communications, 2018, vol. 9, No. 1178, pp. 1-9 (9 pages total).

Yumei Xiong, et al., "Long-acting MIC-1/GDF15 molecules to treat obesity: Evidence from mice to monkeys", Sci. Transl. Med., 2017, vol. 9, pp. 1-11 (11 pages total).

Ryan G. Walker, et al., "New Insight Into Hyperemesis Gravidarum and a Potential Role for GDF15", Endocrinology, Jul. 2018, vol. 159, No. 7, pp. : 2698-2700 (3 pages total).

Renske Altena, et al., "Growth Differentiation Factor 15 (GDF-15) Plasma Levels Increase during Bleomycin-and Cisplatin-Based Treatment of Testicular Cancer Patients and Relate to Endothelial Damage", PLoS ONE, Jan. 15, 2015, vol. 10, No. 1, pp. 1-15 (15 pages total).

Tito Borner, et al., "GDF15 Induces Anorexia through Nausea and Emesis", Cell Metab., Feb. 4, 2020, vol. 31, No. 2, pp. 351-362 (33 pages total).

Eurasian Patent Office, Communication issued Nov. 13, 2025 in copending Eurasian Application No. 202291541, with English translation.

Rudikoff et al., "Single amino acid substitution altering antigen-binding specificity", Proc. Nat. Acad. Sci., Immunology, USA, vol. 79, pp. 1979-1983, Mar. 1982.

Colman, "Effects of amino acid sequence changes on antibody-antigen interactions", 55th Forum in Immunology, 1988, pp. 33-36.

Chen et al., "Enhancement and destruction of antibody function by somatic mutation: unequal occurrence is controlled by V gene combinatorial associations", The EMBO Journal, vol. 14, No. 1 2, pp. 2784-2794, 1995.

Brown et al., "Tolerance to Single, but Not Multiple, Amino Acid Replacements in Antibody $V_H$ CDR2", The American Association of Immunologists, 1996, 0022-1 767/96, pp. 3285-3291.

(56)         References Cited

OTHER PUBLICATIONS

Christian Klein et al., "Epitope interactions of monoclonal antibod-
ies targeting CD20 and their relationship to functional properties",
mAbs, 2013, vol. 5, No. 1, pp. 22-33 (12 pages total).

* cited by examiner

Fig. 2B
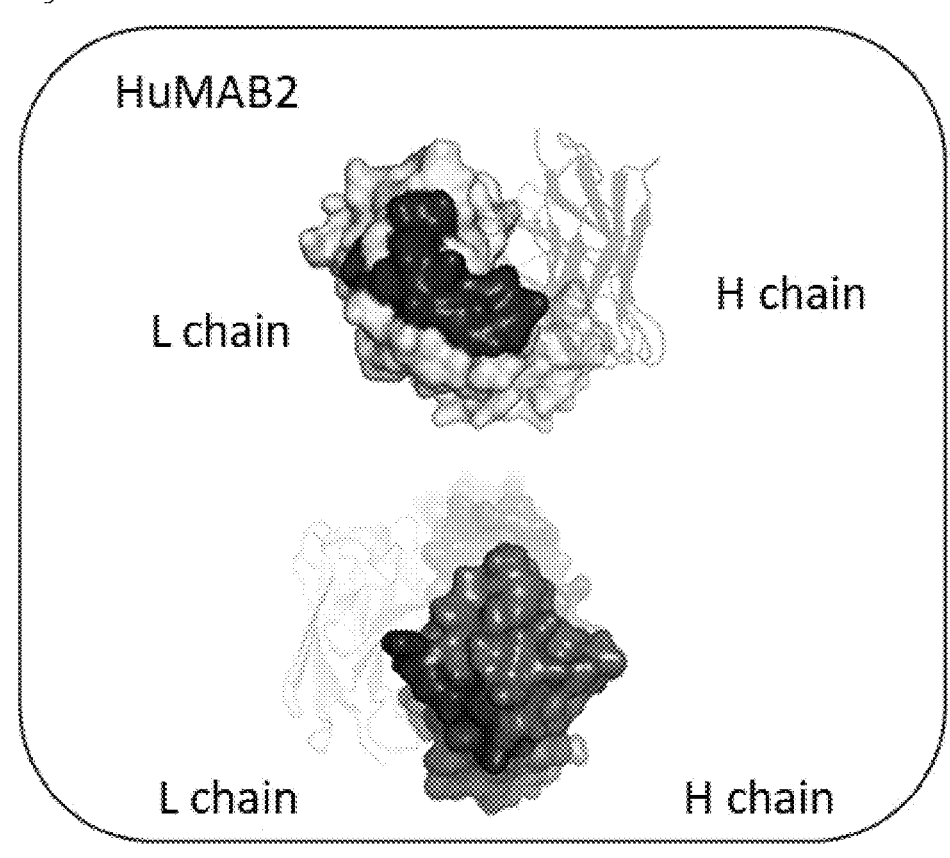
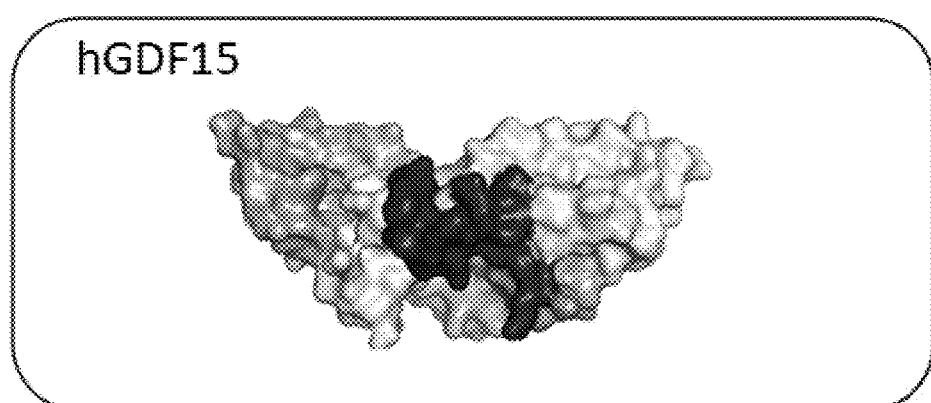

hGDF15

```
             10        20          30          40
ARNGDHCPLG PGRCCRLHTV RASLEDLGWA DWVLSPREVQ
             50        60          70          80
VTMCIGACPS QFRAANMHAQ IKTSLHRLKP DTVPAPCCVP
             90       100         110  112
ASYNPMVLIQ KTDTGVSLQT YDDLLAKDCH CI    (SEQ ID NO: 2 )
```

| Group | Treatment |
|-------|-----------|
| 1 | Vehicle |
| 2 | rhGDF15 0.3mg/kg |
| 3 | rhGDF15 1mg/kg |
| 4 | rhGDF15 3mg/kg |
| 5 | rhGDF15 3mg/kg + MAB17   3mg/kg |
| 6 | rhGDF15 3mg/kg + HuMAB2   3mg/kg |

Fig. 7
Test schedule
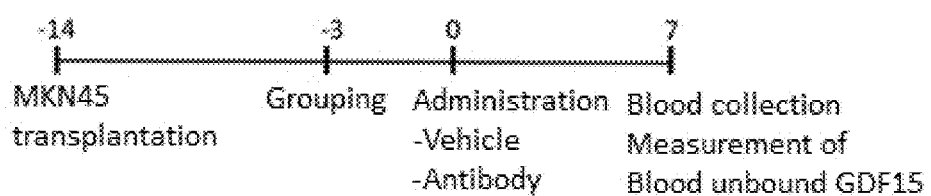
Blood unbound GDF15
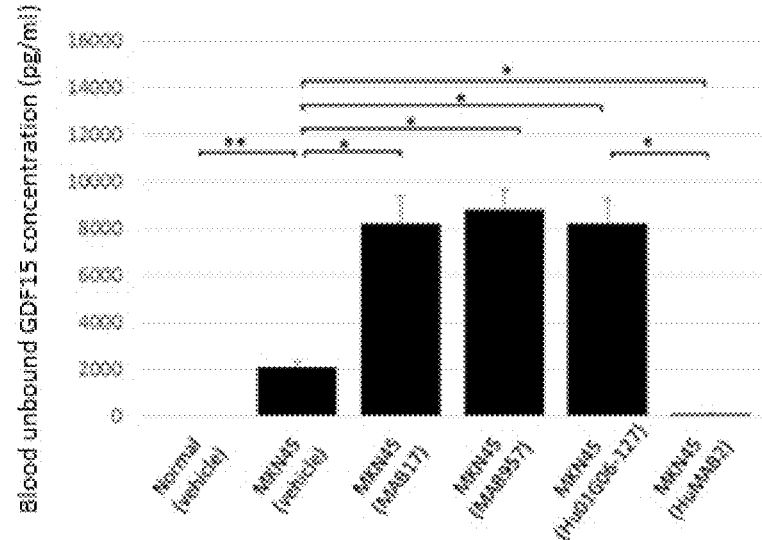
N=5 mean±SEM, *P<0.05, **P<0.01

Fig. 10
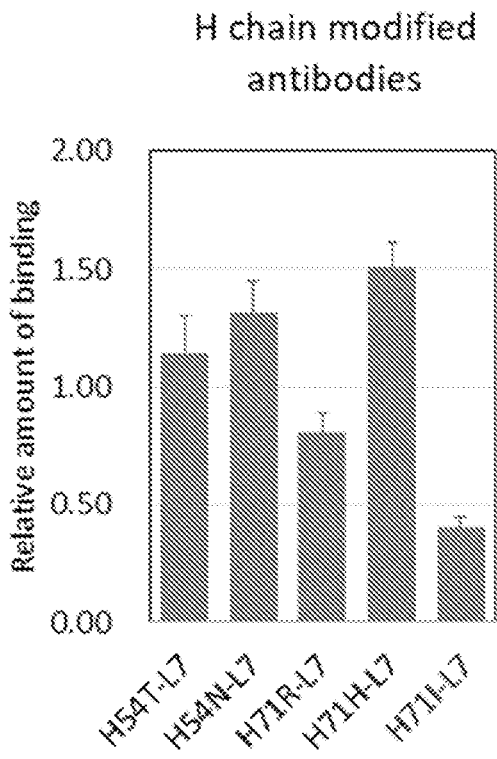
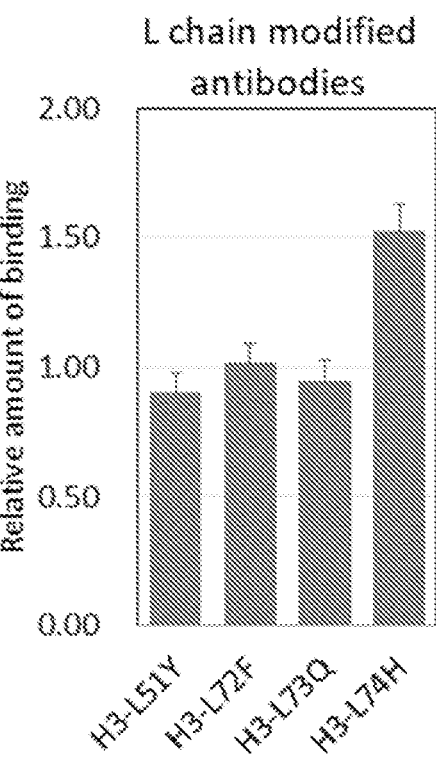

Fig. 13
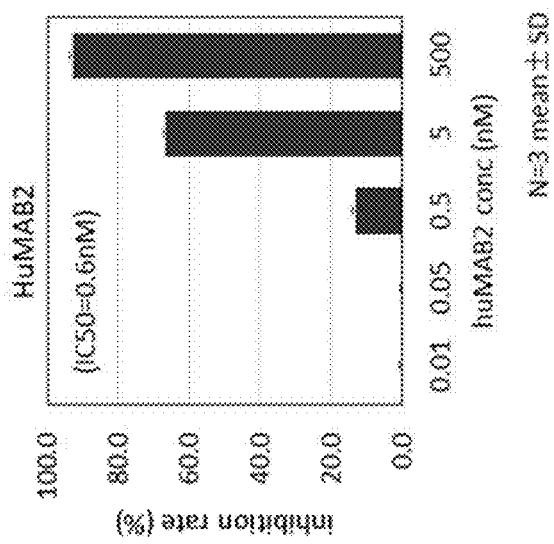
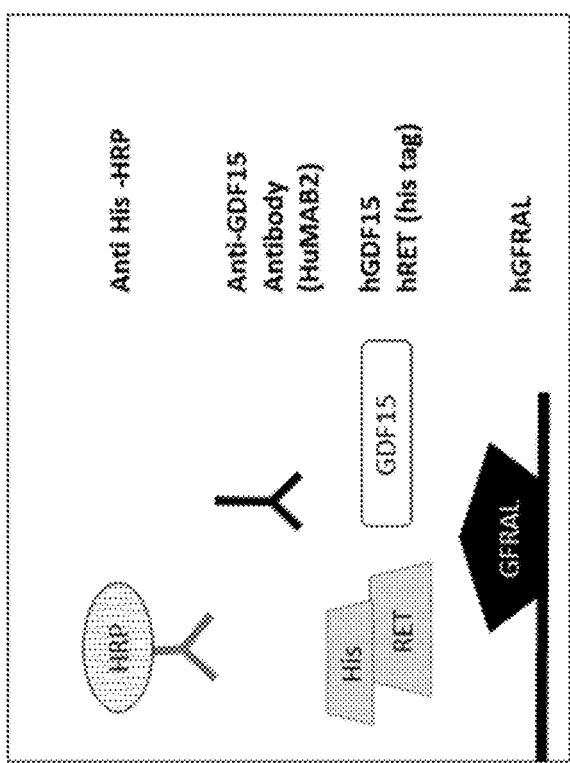

Fig. 14

Blood unbound GDF15 concentration

Cumulative food intake

Body weight change

ANTI-GDF15 ANTIBODY

CROSS REFERENCE TO RELATED APPLICATIONS

This application is a National Stage of International Application No. PCT/JP2020/045062 filed Dec. 3, 2020, claiming priority based on International Application No. PCT/JP2019/047956 filed Dec. 6, 2019.

TECHNICAL FIELD

The present application claims priority with respect to International Application No. PCT/JP2019/047956, which is incorporated herein by reference in its entirety.

The present disclosure relates to anti-GDF15 antibodies and uses thereof.

BACKGROUND

Cachexia is a complex metabolic disease characterized by weight loss and muscle weakness associated with chronic diseases. Among them, cancer cachexia is found in many patients with advanced cancer and requires aggressive treatment as it deteriorates prognosis and QOL of the patients. However, since pathophysiology of cachexia is complicated and there are many unclear points about the mechanism of its occurrence, no effective therapeutic agent is currently available.

GDF15 (Growth Differentiation Factor 15) is a secretory protein of the TGF-β superfamily and has been reported to be involved in various diseases such as cancer and diabetes. There are many reports of clinical studies on blood GDF15 concentration. For example, high GDF15 levels in blood and cancer tissues in cancer patients and correlation between blood GDF15 levels and prognosis in cancer patients are reported. GDF15 is also known to act on the feeding center of the brain to induce anorexia and known to be involved in the development of cachexia.

SUMMARY

Problem to be Solved

An object of the present disclosure is to provide an anti-GDF15 antibody useful in the treatment of a disease or symptom associated with GDF15.

Means for Solving Problem

In an aspect, the present disclosure provides an anti-hGDF15 antibody, wherein the antibody binds to an epitope of hGDF15 comprising the amino acid sequence of DHCPLGPGRCCRLH (SEQ ID NO: 3).

In a further aspect, the present disclosure provides an anti-hGDF15 antibody, wherein the antibody comprises a heavy chain variable region that contains CDR1 contained in a heavy chain variable region comprising the amino acid sequence of SEQ ID NO: 4, or CDR1 consisting of an amino acid sequence that differs from the amino acid sequence of the CDR1 contained in the heavy chain variable region comprising the amino acid sequence of SEQ ID NO: 4 by having amino acid modification of one to three amino acid residues, CDR2 contained in a heavy chain variable region comprising the amino acid sequence of SEQ ID NO: 4, or CDR2 consisting of an amino acid sequence that differs from the amino acid sequence of the CDR2 contained in the heavy chain variable region comprising the amino acid sequence of SEQ ID NO: 4 by having amino acid modification of one to three amino acid residues, and CDR3 contained in a heavy chain variable region comprising the amino acid sequence of SEQ ID NO: 4, or CDR3 consisting of an amino acid sequence that differs from the amino acid sequence of the CDR3 contained in the heavy chain variable region comprising the amino acid sequence of SEQ ID NO: 4 by having amino acid modification of one to three amino acid residues; and a light chain variable region that contains CDR1 contained in a light chain variable region comprising the amino acid sequence of SEQ ID NO: 5, or CDR1 consisting of an amino acid sequence that differs from the amino acid sequence of the CDR1 contained in the light chain variable region comprising the amino acid sequence of SEQ ID NO: 5 by having amino acid modification of one to three amino acid residues, CDR2 contained in a light chain variable region comprising the amino acid sequence of SEQ ID NO: 5, or CDR2 consisting of an amino acid sequence that differs from the amino acid sequence of the CDR2 contained in the light chain variable region comprising the amino acid sequence of SEQ ID NO: 5 by having amino acid modification of one to three amino acid residues, and CDR3 contained in a light chain variable region comprising the amino acid sequence of SEQ ID NO: 5, or CDR3 consisting of an amino acid sequence that differs from the amino acid sequence of the CDR3 contained in the light chain variable region comprising the amino acid sequence of SEQ ID NO: 5 by having amino acid modification of one to three amino acid residues.

In a further aspect, the present disclosure provides an anti-hGDF15 antibody, wherein the antibody comprises a heavy chain variable region that contains CDR1 comprising the amino acid sequence of SEQ ID NO: 18 or an amino acid sequence that differs from the amino acid sequence of SEQ ID NO: 18 by having amino acid modification of one to three amino acid residues, CDR2 comprising the amino acid sequence of SEQ ID NO: 19 or an amino acid sequence that differs from the amino acid sequence of SEQ ID NO: 19 by having amino acid modification of one to three amino acid residues, and CDR3 comprising the amino acid sequence of SEQ ID NO: 20 or an amino acid sequence that differs from the amino acid sequence of SEQ ID NO: 20 by having amino acid modification of one to three amino acid residues; and a light chain variable region that contains CDR1 comprising the amino acid sequence of SEQ ID NO: 21 or an amino acid sequence that differs from the amino acid sequence of SEQ ID NO: 21 by having amino acid modification of one to three amino acid residues, CDR2 comprising the amino acid sequence of SEQ ID NO: 22 or an amino acid sequence that differs from the amino acid sequence of SEQ ID NO: 22 by having amino acid modification of one to three amino acid residues, and CDR3 comprising the amino acid sequence of SEQ ID NO: 23 or an amino acid sequence that differs from the amino acid sequence of SEQ ID NO: 23 by having amino acid modification of one to three amino acid residues.

In a further aspect, the present disclosure provides an anti-hGDF15 antibody, wherein the antibody comprises a heavy chain variable region comprising an amino acid sequence having 80%, 85%, 90%, 95%, or more sequence identity to the amino acid sequence of SEQ ID NO: 8, or the amino acid sequence of SEQ ID NO: 8 or an amino acid sequence that differs from the amino acid sequence of SEQ ID NO: 8 by having amino acid modification of 1 to 20, 1 to 15, 1 to 10, 1 to 5, or 1 to 3 amino acid residues; and a light chain variable region comprising an amino acid sequence having 80%, 85%, 90%, 95%, or more sequence identity to the amino acid sequence of SEQ ID NO: 9, or the amino acid sequence of SEQ ID NO: 9 or an amino acid sequence that differs from the amino acid sequence of SEQ ID NO: 9 by having amino acid modification of 1 to 20, 1 to 15, 1 to 10, 1 to 5, or 1 to 3 amino acid residues.

In a further aspect, the present disclosure provides an anti-hGDF15 antibody, wherein the antibody comprises a heavy chain variable region that contains CDR1 contained in a heavy chain variable region comprising the amino acid sequence of SEQ ID NO: 133, or CDR1 consisting of an amino acid sequence that differs from the amino acid sequence of the CDR1 contained in the heavy chain variable region comprising the amino acid sequence of SEQ ID NO: 133 by having amino acid modification of one to three amino acid residues, CDR2 contained in a heavy chain variable region comprising the amino acid sequence of SEQ ID NO: 133, or CDR2 consisting of an amino acid sequence that differs from the amino acid sequence of the CDR2 contained in the heavy chain variable region comprising the amino acid sequence of SEQ ID NO: 133 by having amino acid modification of one to three amino acid residues, and CDR3 contained in a heavy chain variable region comprising the amino acid sequence of SEQ ID NO: 133, or CDR3 consisting of an amino acid sequence that differs from the amino acid sequence of the CDR3 contained in the heavy chain variable region comprising the amino acid sequence of SEQ ID NO: 133 by having amino acid modification of one to three amino acid residues; and a light chain variable region that contains CDR1 contained in a light chain variable region comprising the amino acid sequence of SEQ ID NO: 134, or CDR1 consisting of an amino acid sequence that differs from the amino acid sequence of the CDR1 contained in the light chain variable region comprising the amino acid sequence of SEQ ID NO: 134 by having amino acid modification of one to three amino acid residues, CDR2 contained in a light chain variable region comprising the amino acid sequence of SEQ ID NO: 134, or CDR2 consisting of an amino acid sequence that differs from the amino acid sequence of the CDR2 contained in the light chain variable region comprising the amino acid sequence of SEQ ID NO: 134 by having amino acid modification of one to three amino acid residues, and CDR3 contained in a light chain variable region comprising the amino acid sequence of SEQ ID NO: 134, or CDR3 consisting of an amino acid sequence that differs from the amino acid sequence of the CDR3 contained in the light chain variable region comprising the amino acid sequence of SEQ ID NO: 134 by having amino acid modification of one to three amino acid residues.

In a further aspect, the present disclosure provides an anti-hGDF15 antibody, wherein the antibody comprises a heavy chain variable region that contains CDR1 comprising the amino acid sequence of SEQ ID NO: 137 or an amino acid sequence that differs from the amino acid sequence of SEQ ID NO: 137 by having amino acid modification of one to three amino acid residues, CDR2 comprising the amino acid sequence of SEQ ID NO: 138 or an amino acid sequence that differs from the amino acid sequence of SEQ ID NO: 138 by having amino acid modification of one to three amino acid residues, and CDR3 comprising the amino acid sequence of SEQ ID NO: 139 or an amino acid sequence that differs from the amino acid sequence of SEQ ID NO: 139 by having amino acid modification of one to three amino acid residues; and a light chain variable region that contains CDR1 comprising the amino acid sequence of SEQ ID NO: 140 or an amino acid sequence that differs from the amino acid sequence of SEQ ID NO: 140 by having amino acid modification of one to three amino acid residues, CDR2 comprising the amino acid sequence of SEQ ID NO: 141 or an amino acid sequence that differs from the amino acid sequence of SEQ ID NO: 141 by having amino acid modification of one to three amino acid residues, and CDR3 comprising the amino acid sequence of SEQ ID NO: 142 or an amino acid sequence that differs from the amino acid sequence of SEQ ID NO: 142 by having amino acid modification of one to three amino acid residues.

In a further aspect, the present disclosure provides an anti-hGDF15 antibody, wherein the antibody comprises a heavy chain variable region that contains CDR1 contained in a heavy chain variable region comprising the amino acid sequence of SEQ ID NO: 135, or CDR1 consisting of an amino acid sequence that differs from the amino acid sequence of the CDR1 contained in the heavy chain variable region comprising the amino acid sequence of SEQ ID NO: 135 by having amino acid modification of one to three amino acid residues, CDR2 contained in a heavy chain variable region comprising the amino acid sequence of SEQ ID NO: 135, or CDR2 consisting of an amino acid sequence that differs from the amino acid sequence of the CDR2 contained in the heavy chain variable region comprising the amino acid sequence of SEQ ID NO: 135 by having amino acid modification of one to three amino acid residues, and CDR3 contained in a heavy chain variable region comprising the amino acid sequence of SEQ ID NO: 135, or CDR3 consisting of an amino acid sequence that differs from the amino acid sequence of the CDR3 contained in the heavy chain variable region comprising the amino acid sequence of SEQ ID NO: 135 by having amino acid modification of one to three amino acid residues; and a light chain variable region that contains CDR1 contained in a light chain variable region comprising the amino acid sequence of SEQ ID NO: 136, or CDR1 consisting of an amino acid sequence that differs from the amino acid sequence of the CDR1 contained in the light chain variable region comprising the amino acid sequence of SEQ ID NO: 136 by having amino acid modification of one to three amino acid residues, CDR2 contained in a light chain variable region comprising the amino acid sequence of SEQ ID NO: 136, or CDR2 consisting of an amino acid sequence that differs from the amino acid sequence of the CDR2 contained in the light chain variable region comprising the amino acid sequence of SEQ ID NO: 136 by having amino acid modification of one to three amino acid residues, and CDR3 contained in a light chain variable region comprising the amino acid sequence of SEQ ID NO: 136, or CDR3 consisting of an amino acid sequence that differs from the amino acid sequence of the CDR3 contained in the light chain variable region comprising the amino acid sequence of SEQ ID NO: 136 by having amino acid modification of one to three amino acid residues.

In a further aspect, the present disclosure provides an anti-hGDF15 antibody, wherein the antibody comprises a heavy chain variable region that contains CDR1 comprising the amino acid sequence of SEQ ID NO: 143 or an amino acid sequence that differs from the amino acid sequence of SEQ ID NO: 143 by having amino acid modification of one to three amino acid residues, CDR2 comprising the amino acid sequence of SEQ ID NO: 144 or an amino acid sequence that differs from the amino acid sequence of SEQ ID NO: 144 by having amino acid modification of one to three amino acid residues, and CDR3 comprising the amino acid sequence of SEQ ID NO: 145 or an amino acid sequence that differs from the amino acid sequence of SEQ ID NO: 145 by having amino acid modification of one to three amino acid residues; and a light chain variable region that contains CDR1 comprising the amino acid sequence of SEQ ID NO: 146 or an amino acid sequence that differs from the amino acid sequence of SEQ ID NO: 146 by having amino acid modification of one to three amino acid residues, CDR2 comprising the amino acid sequence of SEQ ID NO: 147 or an amino acid sequence that differs from the amino acid sequence of SEQ ID NO: 147 by having amino acid modification of one to three amino acid residues, and CDR3 comprising the amino acid sequence of SEQ ID NO: 148 or an amino acid sequence that differs from the amino acid sequence of SEQ ID NO: 148 by having amino acid modification of one to three amino acid residues.

In a further aspect, the present disclosure provides an anti-hGDF15 antibody that competes for binding to hGDF15 with the antibody of any one of the preceding paragraphs.

In a further aspect, the present disclosure provides a polynucleotide encoding the antibody of any one of the preceding paragraphs, an expression vector comprising the polynucleotide, or a transformed cell comprising the polynucleotide.

In a further aspect, the present disclosure provides a pharmaceutical composition comprising the antibody of any one of the preceding paragraphs.

Effect of Invention

The anti-hGDF15 antibody of the present disclosure recognizes an epitope different from epitopes of existing anti-hGDF15 antibodies and it is useful for treating a disease or symptom associated with GDF15.

BRIEF DESCRIPTION OF DRAWINGS

FIG. 2B shows the results of analysis of an epitope and a paratope by the three-dimensional structure analysis of the cocrystal of HuMAB2 Fab and hGDF15.

FIG. 7 shows the effect of an anti-hGDF15 antibody on blood unbound hGDF15 concentration in a cancer-bearing mouse model.

FIG. 10 shows the binding of HuMAB2 variants to hGDF15.

FIG. 13 shows a schema of evaluation of inhibitory activity of HuMAB2 against GDF15, GFRAL and RET complex formation and the results of the evaluation.

7

Figure 14:
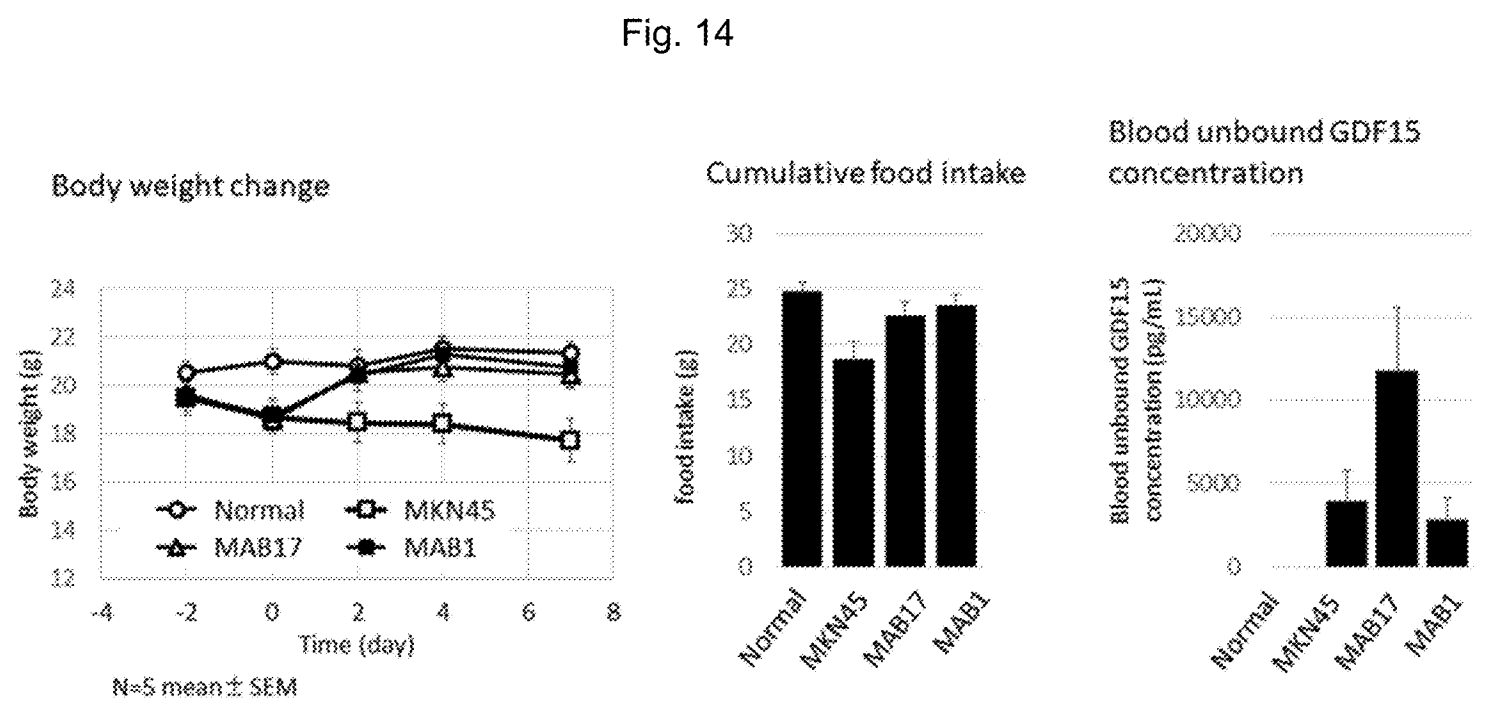
Figure 1:
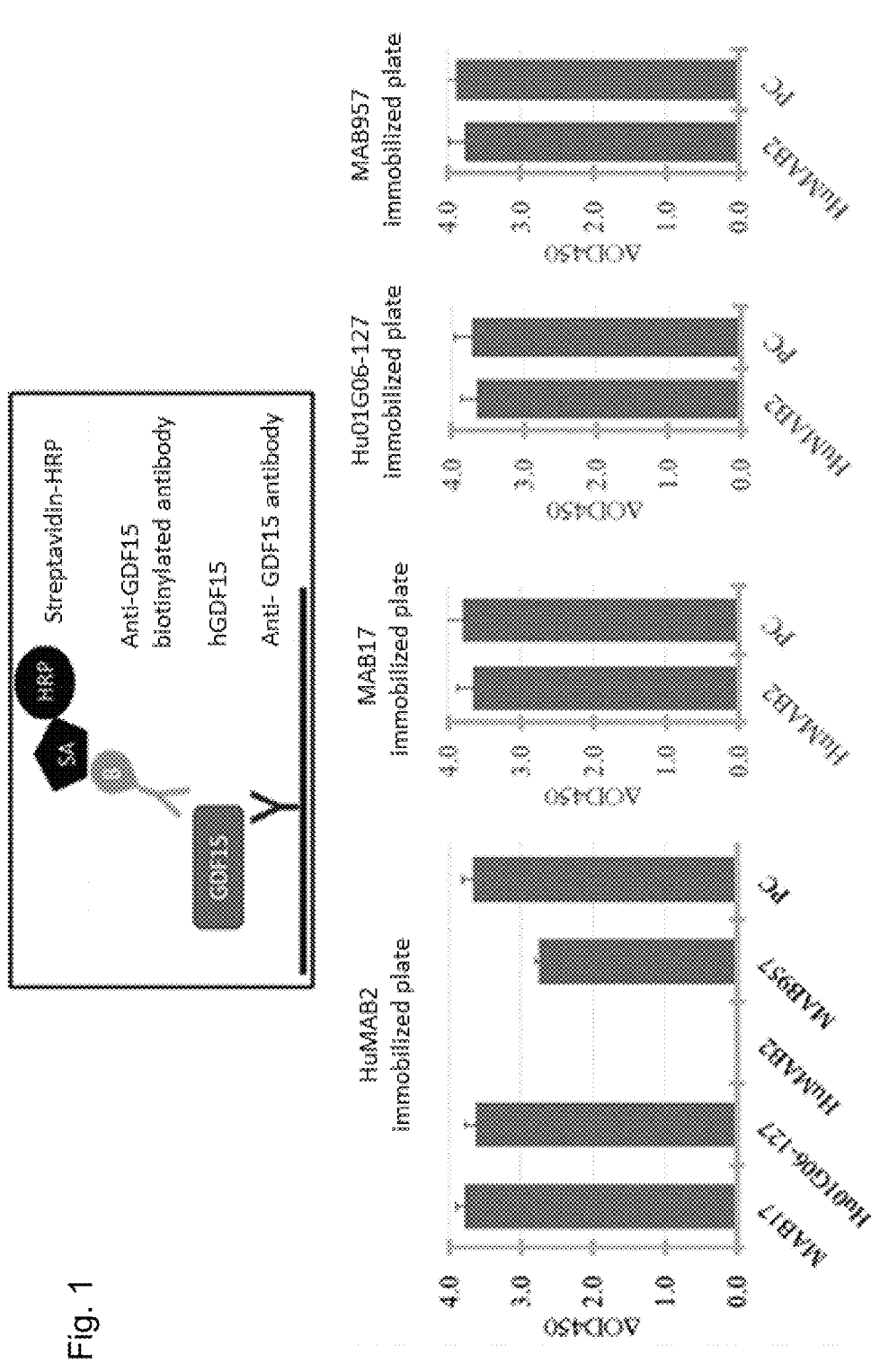
FIG. 1 shows the results of competitive tests using four anti-hGDF15 monoclonal antibodies (HuMAB2, MAB17, Hu01G06-127, MAB957).

FIG. 14 shows the effect of MAB1 on weight loss, cumulative food intake, and blood unbound hGDF15 concentration in the cancer-bearing mouse model.

DETAILED DESCRIPTION OF EMBODIMENTS

Unless otherwise specified, the terms used herein have the meanings generally understood by those skilled in the art in the fields such as organic chemistry, medical science, pharmaceutical science, molecular biology, and microbiology. Definitions of some terms used herein are provided below, and these definitions herein supersede the general understandings.

In the present disclosure, when a number is accompanied by the term "about", it is intended to include a range of ±10% of that value. For example, "about 20" shall include "18 to 22". A range of numbers includes all numbers between the endpoints and the numbers at the endpoints. The "about" for a range applies to both ends of the range. Thus, for example, "about 20 to 30" shall include "18 to 33".

In the present specification, amino acid residues are represented by the following abbreviations.

Ala or A: Alanine
Arg or R: Arginine
Asn or N: Asparagine
Asp or D: Aspartic acid
Cys or C: Cysteine
Gln or Q: Glutamine
Glu or E: Glutamic acid
Gly or G: Glycine
His or H: Histidine
Ile or I: Isoleucine
Leu or L: Leucine
Lys or K: Lysine
Met or M: Methionine
Phe or F: Phenylalanine
Pro or P: Proline
Ser or S: Serine
Thr or T: Threonine
Trp or W: Tryptophan
Tyr or Y: Tyrosine
Val or V: Valine In the present specification, an amino acid residue in an amino acid sequence may be indicated by the number representing its position and an abbreviation representing the amino acid residue (for example, an arginine residue at position 13 is referred to as "13R").

GDF15 (Growth Differentiation Factor 15) is a secreted protein of the TGF-β superfamily, also known as MIC-1, PLAB, PDF, and NAG-1. The GDF15 gene expresses a precursor, pro GDF15, and this pro GDF15 is cleaved by a membrane-type metalloendoprotease to produce mature GDF15. GDF15 is soluble and thought to form a dimer to be recognized by its receptor, GFRAL. Unless otherwise stated, the term GDF15 as used herein means mature GDF15.

As used herein, the term GDF15 is intended to include GDF15 of any species. In an embodiment, GDF15 is human GDF15 (hGDF15). The representative amino acid sequence of pro hGDF15 is shown in SEQ ID NO: 1. Pro hGDF15 is a 308 amino acid polypeptide composed of a signal peptide of 29 amino acids (underlined), a propeptide of 167 amino acids, and a mature peptide of 112 amino acids (double underlined, hGDF15). The representative amino acid sequence of hGDF15 is shown in SEQ ID NO: 2, but hGDF15 in the present disclosure is not limited to polypeptides comprising the amino acid sequence of SEQ ID NO: 2.

8

```
Pro hGDF15
                                        (SEQ ID NO: 1)
MPGQELRTVN GSQMLLVLLV LSWLPHGGAL SLAEASRASF

PGPSELHSED SRFRELRKRY EDLLTRLRAN QSWEDSNTDL

VPAPAVRILT PEVRLGSGGH LHLRISRAAL PEGLPEASRL

HRALFRLSPT ASRSWDVTRP LRRQLSLARP QAPALHLRLS

PPPSQSDQLL AESSSARPQL ELHLRPQAAR GRRRARARNG

DHCPLGPGRC CRLHTVRASL EDLGWADWVL SPREVQVTMC

IGACPSQFRA ANMHAQIKTS LHRLKPDTVP APCCVPASYN

PMVLIQKTDT GVSLQTYDDL LAKDCHCI hGDF15
                                        (SEQ ID NO: 2)
ARNGDHCPLG PGRCCRLHTV RASLEDLGWA DWVLSPREVQ

VTMCIGACPS QFRAANMHAQ IKTSLHRLKP DTVPAPCCVP

ASYNPMVLIQ KTDTGVSLQT YDDLLAKDCH CI
```

The term "antibody" as used herein means a molecule comprising an immunoglobulin or a part thereof and being capable of binding to an antigen, and is intended to include not only molecules in the form of natural immunoglobulins, but also various molecules having different structures such as chimeric antibodies, humanized antibodies, multispecific antibodies and antibody fragments. The term "monoclonal" as used herein is used to distinguish the antibody from "a polyclonal antibody", which is a mixture of multiple antibodies against different epitopes, and means that the antibody can be obtained from a population of a single antibody. Therefore, the term "monoclonal antibody" can mean, for example, a chimeric antibody, a humanized antibody, a human antibody, a multispecific antibody, and an antibody fragment. An antibody fragment means a molecule comprising a part of an immunoglobulin as its constituent. Examples of antibody fragments include, but are not limited to, heavy and light chain variable regions of an antibody ($V_H$ and $V_L$), F (ab')$_2$, Fab', Fab, Fv, disulphide-linked FV (sdFv), Single-Chain FV (scFV) and conjugates thereof. The antibody is not limited to an antibody of a particular species, and may be a mouse, rat, rabbit, goat, or human antibody.

As used herein, the term "isolated" means that a biological molecule (eg, antibody or polynucleotide) is substantially separated from other components in its natural environment.

The immunoglobulin class of an antibody is determined based on its heavy chain constant region. Immunoglobulin classes include IgA, IgD, IgE, IgG, and IgM, and the corresponding heavy chains are called α chain, δ chain, ε chain, γ chain, and μ chain, respectively. The immunoglobulin class can be further classified into subclasses (isotypes) such as IgG1, IgG2, IgG3, IgG4, IgA1 and IgA2. The immunoglobulin class and subclass of the antibody of the present specification are not limited to any specific class and subclass. In an embodiment, the immunoglobulin class is IgG. The light chain of an antibody can be divided into κ chain and λ chain based on its constant region, and the antibody of the present specification may have either κ chain or λ chain.

The variable region of an antibody is usually composed of three complementarity determining regions (also referred to as CDRs) sandwiched between four framework regions (also referred to as FRs). FRs and CDRs generally exist in the order of FR1-CDR1-FR2-CDR2-FR3-CDR3-FR4 for both light and heavy chains. Several methods have been reported for defining variable regions and CDRs of antibodies and examples of such methods include definitions of Kabat (Sequences of Proteins of Immunological Interest, 5th ed., Public Health Service, National Institutes of Health, Bethesda, MD. 1991), Chothia (Chothia et al., J. Mol. Biol., 1987; 196: 901-917), AbM (Martin et al., Proc. Natl. Acad. Sci. USA, 1989; 86: 9268-9272), Contact (MacCallum et al., J. Mol. Biol. 1996; 262: 732-745) and IMGT (Lefranc et al., Dev Comp Immunol. 2003; 27(1): 55-77). In the present specification, the definition of Kabat is used unless otherwise stated.

As used herein, an anti-hGDF15 antibody means an antibody that binds to hGDF15 with sufficient affinity to exert a desired effect. The anti-hGDF15 antibody of the present disclosure can be obtained by a general method using hGDF15 or a part thereof as an immunogen. The immunogen can be prepared by conventional methods for peptide synthesis, for example by genetic engineering techniques or chemical synthesis. Alternatively, the antibody of the present disclosure can be obtained by preparing an expression vector comprising the gene of the antibody using genetic engineering techniques and expressing the antibody in cells.

A polyclonal antibody can be prepared by general methods such as methods described in "Antibodies: A Laboratory Manual, Lane, H. D. et al. eds., Cold Spring Harbor Laboratory Press, New York, 1989". Specifically, a polyclonal antibody can be prepared by immunizing a mammal such as a rat, mouse, rabbit, goat, or horse with the above-mentioned immunogen.

A monoclonal antibody can be obtained by methods known in the art, for example by preparing a hybridoma that produces the antibody, or by preparing an expression vector comprising the gene of the antibody using genetic engineering techniques and expressing the antibody in cells.

A hybridoma that secretes a monoclonal antibody can be prepared according to the method described in Kohler et al., Nature 256: 495, 1975. First, an immunogen is mixed with a suitable substance for enhancing antigenicity of the immunogen (eg, keyhole limpet hemocyanin or bovine serum albumin) and, if necessary, with an immunostimulant (eg, Freund's complete or incomplete adjuvant), and used to immunize a non-human mammal such as rat, mouse, rabbit, goat or horse. Usually, the animal is immunized multiple times at intervals of 3 to 10 days, and 1 to 100 μg of the immunogen peptide is administered. Immune cells (cells capable of producing antibodies in the immunized animal) are then recovered from the immunized animal after multiple immunizations, and fused with myeloma cells that are not capable of producing their own antibodies (for example, cells derived from a mammal such as mouse, rat, guinea pig, hamster, rabbit, or human). The cell fusion can be carried out using polyethylene glycol, or by electric fusion, for example. Then, cells that are successfully provided by cell fusion are selected based on the selection marker possessed by the fused cells, and the reactivity of the antibody produced by the selected cells to the immunogen is confirmed, for example by the immunoassay as described below, and finally a hybridoma that produces a monoclonal antibody of interest is obtained. The monoclonal antibody can be isolated from culture supernatant prepared by culturing the hybridoma thus obtained in vitro. Alternatively, the hybridoma can be cultured in vivo in ascites of an animal such as mouse, rat, guinea pig, hamster or rabbit, and the monoclonal antibody can be isolated from the ascites.

A monoclonal antibody can also be obtained by preparing an expression vector comprising the gene of the antibody and expressing the antibody in host cells (P. J. Delves., ANTIBODY PRODUCTION ESSENTIAL TECHNIQUES., 1997 WILEY; P. Shepherd and C. Dean., Monoclonal Antibodies., 2000 OXFORD UNIVERSITY PRESS; J. W. Goding., Monoclonal Antibodies: principles and practice., 1993 ACADEMIC PRESS). Alternatively, a monoclonal antibody can be obtained by using techniques for producing transgenic animals to produce a transgenic animal (eg, cow, goat, sheep or pig) in which the gene of the antibody of interest is introduced into endogenous genes. The monoclonal antibody derived from the antibody gene can be obtained from milk of the transgenic animal.

The monoclonal antibody thus obtained can be purified by appropriately combining methods well known in the art, such as chromatography using protein A columns, ion exchange chromatography, hydrophobic chromatography, salting-out method, gel filtration, and affinity chromatography.

A chimeric antibody is an antibody that contains sequences derived from different origins, and can be an antibody in which a variable region derived from one origin is linked to a constant region derived from another origin. In an embodiment, a chimeric antibody is composed of a variable region of an antibody derived from a non-human mammal and a constant region derived from a human antibody. A chimeric antibody can be obtained, for example, by connecting a polynucleotide encoding a variable region of an antibody of a non-human mammal and a polynucleotide encoding a constant region of a human antibody, incorporating the polynucleotide thus obtained into an expression vector, introducing the expression vector into a host, and expressing the antibody in the host.

The CDR is a region that substantially determines the binding specificity of an antibody, and amino acid sequences of CDRs show a great diversity. In contrast, amino acid sequences constituting FRs show a high homology even among antibodies having different binding specificities. Therefore, the binding specificity of one antibody can be transplanted to another antibody by transplanting CDRs.

Various methods for CDR transplantation are known and are described, for example, in the following documents: U.S. Pat. Nos. 7,022,500, 6,982,321, 6,180,370, 6,054,297. Specification, U.S. Pat. Nos. 5,693,762, 5,859,205, 5,693,761, 5,565,332; 5,585,089, 5,530,101, 5,225,539; Jones et al. (1986) Nature 321:522-525; Riechmann et al. (1988) Nature 332: 323-327; Queen, et al. (1989) Proc. Natl. Acad. U.S.A. 86:10029-10033; Verhoeyen et al. (1988) Science 239:1534-1536; Winter (1998) FEBS lett 430:92-94.

A humanized antibody is generally composed of CDRs of an antibody derived from a non-human animal, FRs derived from a human antibody, and constant regions derived from a human antibody. A humanized antibody can be obtained by transplanting CDRs of an antibody derived from a non-human animal into a human antibody. A humanized antibody can be prepared by various methods, one example of which is Overlap Extension PCR (Almagro and Fransson, Front. Biosci. 13:1619-1633(2008)). In this method, an oligonucleotide having a portion that overlaps the end of a CDR of a non-human animal antibody (for example, a mouse antibody) and a FR of a human antibody is used as a primer for PCR to synthesize a polynucleotide in which the CDR of the non-human animal antibody and the FR of the human antibody are linked. Next, the polynucleotide thus obtained is ligated with a polynucleotide encoding a constant region of a human antibody and incorporated into an expression vector, and the expression vector is introduced into a host for expression to obtain a humanized antibody.

The sequences of FRs can be determined based on a database (eg, VBase, mrc-lmb.cam.ac.uk/vbase/), which discloses germline antibody gene sequences, or references (eg, Kabat et al., Sequences of Proteins of Immunological Interest, 5th ed., Public Health Service, National Institutes of Health, Bethesda, MD. 1991); Tomlinson, I. M. et al. (1992) J. Mol. Biol. 227:776-798; Cox, J. P. L. et al. (1994) Eur. J Immunol. 24:827-836). FRs may contain one or more amino acid mutations as compared to germline sequences. How to select suitable FRs has been known and FRs may be those selected by Best fit method (Sims et al. J. Immunol. 151: 2296 (1993)) or those derived from the consensus sequences of a specific subgroup of the light or heavy chain variable region of human antibodies (Carter et al. Proc. Natl. Acad. Sci. USA 89:4285 (1992); Presta et al. J. Immunol. 151:2623 (1993)).

A human antibody can be obtained, for example, by sensitizing human lymphocytes in vitro with a desired antigen and then fusing the sensitized lymphocytes with human myeloma cells (Japanese Patent Publication No. Heil-59878). For human myeloma cells, which are fusion partners, U266 can be used for example. A human antibody can also be obtained by immunizing a transgenic animal having the entire repertoire of human antibody genes with a desired antigen (Lonberg, Nat. Biotech. 23:1117-1125, 2005). It is also known that a human antibody can be obtained by panning using a human antibody library (Antibody Phage Display: Methods and Protocols, Methods in Molecular Biology 178, 2001). For example, variable regions of human antibodies are expressed as a single-chain antibody (scFv) on the surface of phages by phage display method to select a phage that binds to the antigen, and the gene of the selected phage is analyzed to determine the DNA sequence encoding the variable region of a human antibody that binds to the antigen. The human antibody can then be obtained by ligating this variable region sequence with a constant region sequence of a human antibody in-frame, inserting the sequence into an appropriate expression vector, introducing this expression vector into a host, and expressing the antibody.

A multispecific antibody is an antibody that binds to at least two different sites. Examples of multispecific antibodies include bispecific antibodies and trispecific antibodies. In an embodiment, the multispecific antibody binds hGDF15 and one or more different antigens. A multispecific antibody can be prepared, for example, by genetic engineering techniques or by binding two or more antibodies that recognize different antigens.

An antibody fragment can be obtained, for example, by digesting an antibody with a protease such as papain or pepsin. Alternatively, an antibody fragment can be obtained by introducing an expression vector comprising a polynucleotide encoding the antibody fragment into host cells and expressing the fragment (for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137; Hudson et al., Nat. Med., (2003) 9, 129-134).

As described above, an antibody can be obtained by introducing an expression vector comprising a polynucleotide encoding the antibody into cells and expressing the antibody. Specifically, an expression vector is constructed so that a sequence encoding an antibody is expressed under an expression control region such as enhancer or promoter, and this expression vector is used to transform host cells to express the antibody.

That is, the present disclosure also provides a polynucleotide encoding an anti-hGDF15 antibody, an expression vector comprising the polynucleotide, and a transformed cell comprising a polynucleotide capable of expressing the antibody as described herein.

As the host cells, eukaryotic cells such as animal cells, plant cells, and fungal cells can be used, for example. Examples of animal cells include mammalian cells (eg, CHO, COS, NIH3T3, myeloma, Baby Hamster Kidney (BHK), HeLa, Vero), amphibian cells (eg, Xenopus oocytes), and insect cells (eg, Sf9, Sf21, Tn5). Fungal cells include yeast (eg, Saccharomyces genus such as Saccharomyces cerevisiae) and filamentous fungi (eg, Aspergillus genus such as Aspergillus niger). Also, prokaryotic cells such as E. coli (eg, JM109, DH5α, HB101) and Bacillus subtilis can also be used as host cells. The vector can be introduced into the host cells by a method using calcium phosphate or DEAE-dextran, electroporation, or lipofection, for example.

Binding of the obtained antibody to the antigen can be confirmed by immunoassays such as enzyme immunoassay (EIA) (including ELISA), radioimmunoassay (RIA), chemoluminescence immunoassay (CIA), and fluorescence immunoassay (FIA), or BIACORE® surface plasmon resonance assay. Binding of the antibody to the antigen can also be confirmed by a competitive assay. For example, it can be confirmed by examining whether the obtained antibody competes with an anti-hGDF15 antibody that has been confirmed to bind to hGDF15.

As used herein, an antibody that competes with a given anti-hGDF15 antibody (i.e., a reference antibody) means an antibody that significantly reduces the binding of the reference antibody to hGDF15 when measured under the conditions described in the Examples. In an embodiment, the antibody of the present disclosure reduces the binding of the reference antibody to hGDF15 by 10%, 20%, 30%, 40%, 50%, 60%, 70%, 80%, 90%, or 95% or more.

In an embodiment, the anti-hGDF15 antibody of the present disclosure binds to an epitope of hGDF15 comprising the amino acid sequence of DHCPLGPGRCCRLH (SEQ ID NO: 3). The amino acid sequence of SEQ ID NO: 3 corresponds to the amino acid residues at positions 5 to 18 of SEQ ID NO: 2. Whether an antibody binds to the epitope comprising the amino acid sequence of DHCPLGPGRC-CRLH (SEQ ID NO: 3) can be confirmed by examining whether the antibody competes for binding to hGDF15 with an antibody comprising a heavy chain variable region comprising the amino acid sequence of SEQ ID NO: 8 and a light chain variable region comprising the amino acid sequence of SEQ ID NO: 9.

In a further embodiment, the anti-hGDF15 antibody of the present disclosure competes with a given anti-hGDF15 antibody for binding to hGDF15. In an embodiment, the antibody of the present disclosure competes for binding to hGDF15 with an antibody comprising a heavy chain variable region comprising the amino acid sequence of SEQ ID NO: 8 and a light chain variable region comprising the amino acid sequence of SEQ ID NO: 9.

In a further embodiment, the anti-hGDF15 antibody of the present disclosure comprises a heavy chain variable region that contains
    CDR1 contained in a heavy chain variable region comprising the amino acid sequence of SEQ ID NO: 4, or CDR1 consisting of an amino acid sequence that differs from the amino acid sequence of the CDR1 contained in the heavy chain variable region comprising the amino acid sequence of SEQ ID NO: 4 by having amino acid modification of one to three amino acid residues, CDR2 contained in a heavy chain variable region comprising the amino acid sequence of SEQ ID NO: 4, or CDR2 consisting of an amino acid sequence that differs from the amino acid sequence of the CDR2 contained in the heavy chain variable region comprising the amino acid sequence of SEQ ID NO: 4 by having amino acid modification of one to three amino acid residues, and CDR3 contained in a heavy chain variable region comprising the amino acid sequence of SEQ ID NO: 4, or CDR3 consisting of an amino acid sequence that differs from the amino acid sequence of the CDR3 contained in the heavy chain variable region comprising the amino acid sequence of SEQ ID NO: 4 by having amino acid modification of one to three amino acid residues; and a light chain variable region that contains CDR1 contained in a light chain variable region comprising the amino acid sequence of SEQ ID NO: 5, or CDR1 consisting of an amino acid sequence that differs from the amino acid sequence of the CDR1 contained in the light chain variable region comprising the amino acid sequence of SEQ ID NO: 5 by having amino acid modification of one to three amino acid residues, CDR2 contained in a light chain variable region comprising the amino acid sequence of SEQ ID NO: 5, or CDR2 consisting of an amino acid sequence that differs from the amino acid sequence of the CDR2 contained in the light chain variable region comprising the amino acid sequence of SEQ ID NO: 5 by having amino acid modification of one to three amino acid residues, and CDR3 contained in a light chain variable region comprising the amino acid sequence of SEQ ID NO: 5, or CDR3 consisting of an amino acid sequence that differs from the amino acid sequence of the CDR3 contained in the light chain variable region comprising the amino acid sequence of SEQ ID NO: 5 by having amino acid modification of one to three amino acid residues;

a heavy chain variable region that contains

CDR1 contained in a heavy chain variable region comprising the amino acid sequence of SEQ ID NO: 133, or CDR1 consisting of an amino acid sequence that differs from the amino acid sequence of the CDR1 contained in the heavy chain variable region comprising the amino acid sequence of SEQ ID NO: 133 by having amino acid modification of one to three amino acid residues, CDR2 contained in a heavy chain variable region comprising the amino acid sequence of SEQ ID NO: 133, or CDR2 consisting of an amino acid sequence that differs from the amino acid sequence of the CDR2 contained in the heavy chain variable region comprising the amino acid sequence of SEQ ID NO: 133 by having amino acid modification of one to three amino acid residues, and CDR3 contained in a heavy chain variable region comprising the amino acid sequence of SEQ ID NO: 133, or CDR3 consisting of an amino acid sequence that differs from the amino acid sequence of the CDR3 contained in the heavy chain variable region comprising the amino acid sequence of SEQ ID NO: 133 by having amino acid modification of one to three amino acid residues; and a light chain variable region that contains CDR1 contained in a light chain variable region comprising the amino acid sequence of SEQ ID NO: 134, or CDR1 consisting of an amino acid sequence that differs from the amino acid sequence of the CDR1 contained in the light chain variable region comprising the amino acid sequence of SEQ ID NO: 134 by having amino acid modification of one to three amino acid residues, CDR2 contained in a light chain variable region comprising the amino acid sequence of SEQ ID NO: 134, or CDR2 consisting of an amino acid sequence that differs from the amino acid sequence of the CDR2 contained in the light chain variable region comprising the amino acid sequence of SEQ ID NO: 134 by having amino acid modification of one to three amino acid residues, and CDR3 contained in a light chain variable region comprising the amino acid sequence of SEQ ID NO: 134, or CDR3 consisting of an amino acid sequence that differs from the amino acid sequence of the CDR3 contained in the light chain variable region comprising the amino acid sequence of SEQ ID NO: 134 by having amino acid modification of one to three amino acid residues; or a heavy chain variable region that contains CDR1 contained in a heavy chain variable region comprising the amino acid sequence of SEQ ID NO: 135, or CDR1 consisting of an amino acid sequence that differs from the amino acid sequence of the CDR1 contained in the heavy chain variable region comprising the amino acid sequence of SEQ ID NO: 135 by having amino acid modification of one to three amino acid residues, CDR2 contained in a heavy chain variable region comprising the amino acid sequence of SEQ ID NO: 135, or CDR2 consisting of an amino acid sequence that differs from the amino acid sequence of the CDR2 contained in the heavy chain variable region comprising the amino acid sequence of SEQ ID NO: 135 by having amino acid modification of one to three amino acid residues, and CDR3 contained in a heavy chain variable region comprising the amino acid sequence of SEQ ID NO: 135, or CDR3 consisting of an amino acid sequence that differs from the amino acid sequence of the CDR3 contained in the heavy chain variable region comprising the amino acid sequence of SEQ ID NO: 135 by having amino acid modification of one to three amino acid residues; and a light chain variable region that contains CDR1 contained in a light chain variable region comprising the amino acid sequence of SEQ ID NO: 136, or CDR1 consisting of an amino acid sequence that differs from the amino acid sequence of the CDR1 contained in the light chain variable region comprising the amino acid sequence of SEQ ID NO: 136 by having amino acid modification of one to three amino acid residues, CDR2 contained in a light chain variable region comprising the amino acid sequence of SEQ ID NO: 136, or CDR2 consisting of an amino acid sequence that differs from the amino acid sequence of the CDR2 contained in the light chain variable region comprising the amino acid sequence of SEQ ID NO: 136 by having amino acid modification of one to three amino acid residues, and CDR3 contained in a light chain variable region comprising the amino acid sequence of SEQ ID NO: 136, or CDR3 consisting of an amino acid sequence that differs from the amino acid sequence of the CDR3 contained in the light chain variable region comprising the amino acid sequence of SEQ ID NO: 136 by having amino acid modification of one to three amino acid residues.

In this embodiment, the CDRs may be identified by any method. The CDR contained in the given heavy or light chain variable region means CDR consisting of an amino acid sequence identified by a certain method from the given heavy or light chain variable region, and the heavy or light chain variable region that contains such CDRs may differ from the given heavy or light chain variable region in a sequence other than the CDRs. One of ordinary skill in the art can identify the CDRs by a suitable method in consideration of various conditions. In an embodiment, the CDRs are identified by any definition selected from Kabat, Chothia, AbM, Contact, and IMGT.

In a further embodiment, the anti-hGDF15 antibody of the present disclosure comprises a heavy chain variable region that contains CDR1 comprising the amino acid sequence of SEQ ID NO: 18 or an amino acid sequence that differs from the amino acid sequence of SEQ ID NO: 18 by having amino acid modification of one to three amino acid residues, CDR2 comprising the amino acid sequence of SEQ ID NO: 19 or an amino acid sequence that differs from the amino acid sequence of SEQ ID NO: 19 by having amino acid modification of one to three amino acid residues, and CDR3 comprising the amino acid sequence of SEQ ID NO: 20 or an amino acid sequence that differs from the amino acid sequence of SEQ ID NO: 20 by having amino acid modification of one to three amino acid residues; and a light chain variable region that contains CDR1 comprising the amino acid sequence of SEQ ID NO: 21 or an amino acid sequence that differs from the amino acid sequence of SEQ ID NO: 21 by having amino acid modification of one to three amino acid residues, CDR2 comprising the amino acid sequence of SEQ ID NO: 22 or an amino acid sequence that differs from the amino acid sequence of SEQ ID NO: 22 by having amino acid modification of one to three amino acid residues, and CDR3 comprising the amino acid sequence of SEQ ID NO: 23 or an amino acid sequence that differs from the amino acid sequence of SEQ ID NO: 23 by having amino acid modification of one to three amino acid residues.

In a further embodiment, the anti-hGDF15 antibody of the present disclosure comprises a heavy chain variable region that contains CDR1 comprising an amino acid sequence selected from SEQ ID NOS: 18, 38-44 and 149-150, CDR2 comprising an amino acid sequence selected from SEQ ID NOS: 19, 45-48, 52-66, and 151-153, and CDR3 comprising an amino acid sequence selected from SEQ ID NOS: 20, 49, 50 and 67-80; and a light chain variable region that contains CDR1 comprising an amino acid sequence selected from SEQ ID NOS: 21, 81-89, 100-104, and 154, CDR2 comprising an amino acid sequence selected from SEQ ID NOS: 22, 90, 106-115, and 155-157, and CDR3 comprising an amino acid sequence selected from SEQ ID NOS: 23, 91-99, and 118-132.

In a further embodiment, the anti-hGDF15 antibody of the present disclosure comprises a heavy chain variable region that contains CDR1 comprising an amino acid sequence selected from SEQ ID NOS: 18, 38-42 and 149-150, CDR2 comprising an amino acid sequence selected from SEQ ID NOS: 19, 46-48, 52-66, and 151-152, and CDR3 comprising an amino acid sequence selected from SEQ ID NOS: 20, 71, 73, 77, and 79; and a light chain variable region that contains CDR1 comprising an amino acid sequence selected from SEQ ID NOS: 21, 81-83, 85-89, 100-104, and 154, CDR2 comprising an amino acid sequence selected from SEQ ID NOS: 22, 90, 106, 108-111, 113-115, and 155-157, and CDR3 comprising an amino acid sequence selected from SEQ ID NOS: 23, 93, 95-99, 121, 122, 124, 125, 131, and 132.

In a further embodiment, the anti-hGDF15 antibody of the present disclosure comprises a heavy chain variable region selected from (1)-(3) and a light chain variable region selected from (4)-(6):

(1) a heavy chain variable region that contains

CDR1 comprising an amino acid sequence selected from SEQ ID NOS: 18, 38-44 and 149-150, CDR2 comprising the amino acid sequence of SEQ ID NO: 19, and CDR3 comprising the amino acid sequence of SEQ ID NO: 20; (2) a heavy chain variable region that contains CDR1 comprising the amino acid sequence of SEQ ID NO: 18, CDR2 comprising an amino acid sequence selected from SEQ ID NOS: 19, 45-48, 52-66, and 151-153, and CDR3 comprising the amino acid sequence of SEQ ID NO: 20; (3) a heavy chain variable region that contains CDR1 comprising the amino acid sequence of SEQ ID NO: 18, CDR2 comprising the amino acid sequence of SEQ ID NO: 19, and CDR3 comprising an amino acid sequence selected from SEQ ID NOS: 20, 49, 50 and 67-80;

(4) a light chain variable region that contains

CDR1 comprising an amino acid sequence selected from SEQ ID NOS: 21, 81-89, 100-104, and 154, CDR2 comprising the amino acid sequence of SEQ ID NO: 22, and CDR3 comprising the amino acid sequence of SEQ ID NO: 23; (5) a light chain variable region that contains CDR1 comprising the amino acid sequence of SEQ ID NO: 21, CDR2 comprising an amino acid sequence selected from SEQ ID NOS: 22, 90, 106-115, and 155-157, and CDR3 comprising the amino acid sequence of SEQ ID NO: 23; and (6) a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 91-99, and 118-132.

In a further embodiment, the anti-hGDF15 antibody of the present disclosure comprises a heavy chain variable region selected from (1)-(3) and a light chain variable region selected from (4)-(6):

(1) a heavy chain variable region that contains

CDR1 comprising an amino acid sequence selected from SEQ ID NOS: 18, 38-42 and 149-150, CDR2 comprising the amino acid sequence of SEQ ID NO: 19, and CDR3 comprising the amino acid sequence of SEQ ID NO: 20; (2) a heavy chain variable region that contains CDR1 comprising the amino acid sequence of SEQ ID NO: 18, CDR2 comprising an amino acid sequence selected from SEQ ID NOS: 19, 46-48, 52-66, and 151-152, and CDR3 comprising the amino acid sequence of SEQ ID NO: 20; (3) a heavy chain variable region that contains CDR1 comprising the amino acid sequence of SEQ ID NO: 18, CDR2 comprising the amino acid sequence of SEQ ID NO: 19, and CDR3 comprising an amino acid sequence selected from SEQ ID NOS: 20, 71, 73, 77, and 79;

(4) a light chain variable region that contains

CDR1 comprising an amino acid sequence selected from SEQ ID NOS: 21, 81-83, 85-89, 100-104, and 154, CDR2 comprising the amino acid sequence of SEQ ID NO: 22, and CDR3 comprising the amino acid sequence of SEQ ID NOS: 23; (5) a light chain variable region that contains CDR1 comprising the amino acid sequence of SEQ ID NO: 21, CDR2 comprising an amino acid sequence selected from SEQ ID NOS: 22, 90, 106, 108-111, 113-115, and 155-157, and CDR3 comprising the amino acid sequence of SEQ ID NOS: 23; and (6) a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 93, 95-99, 121, 122, 124, 125, 131, and 132.

In a further embodiment, the anti-hGDF15 antibody of the present disclosure comprises a heavy chain variable region selected from (1)-(3) and a light chain variable region selected from (4)-(6):

(1) a heavy chain variable region that contains

CDR1 comprising an amino acid sequence selected from SEQ ID NOS: 18, 38, and 39

CDR2 comprising the amino acid sequence of SEQ ID NO: 19, and

CDR3 comprising the amino acid sequence of SEQ ID NO: 20;

(2) a heavy chain variable region that contains

CDR1 comprising the amino acid sequence of SEQ ID NO: 18,

CDR2 comprising an amino acid sequence selected from SEQ ID NOS: 19, 52, and 66, and CDR3 comprising the amino acid sequence of SEQ ID NO: 20;

(3) a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from SEQ ID NOS: 20 and 77;

(4) a light chain variable region that contains

CDR1 comprising an amino acid sequence selected from SEQ ID NOS: 21 and 85,

CDR2 comprising the amino acid sequence of SEQ ID NO: 22, and

CDR3 comprising the amino acid sequence of SEQ ID NOS: 23;

(5) a light chain variable region that contains

CDR1 comprising the amino acid sequence of SEQ ID NO: 21,

CDR2 comprising an amino acid sequence selected from SEQ ID NOS: 22, 155, and 157, and CDR3 comprising the amino acid sequence of SEQ ID NOS: 23; and (6) a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23 and 95.

In a further embodiment, the anti-hGDF15 antibody of the present disclosure comprises (i) a heavy chain variable region that contains CDR1 comprising an amino acid sequence selected from SEQ ID NOS: 18, 38-44, and 149-150, CDR2 comprising the amino acid sequence of SEQ ID NO: 19, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(ii) a heavy chain variable region that contains

CDR1 comprising the amino acid sequence of SEQ ID NO: 18,

CDR2 comprising an amino acid sequence selected from SEQ ID NOS: 19, 45-48, 52-66, and 151-153, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(iii) a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from SEQ ID NOS: 20, 49, 50 and 67-80, and a light chain variable region that contains CDR1 comprising the amino acid sequence of SEQ ID NO: 21, CDR2 comprising the amino acid sequence of SEQ ID NO: 22, and

CDR3 comprising the amino acid sequence of SEQ ID NO: 23;

(iv) a heavy chain variable region that contains
CDR1 comprising the amino acid sequence of SEQ ID NO: 18,
CDR2 comprising the amino acid sequence of SEQ ID NO: 19, and
CDR3 comprising the amino acid sequence of SEQ ID NO: 20; and
a light chain variable region that contains
CDR1 comprising an amino acid sequence selected from SEQ ID NOS: 21, 81-89, 100-104, and 154,
CDR2 comprising the amino acid sequence of SEQ ID NO: 22, and
CDR3 comprising the amino acid sequence of SEQ ID NO: 23;

(v) a heavy chain variable region that contains
CDR1 comprising the amino acid sequence of SEQ ID NO: 18,
CDR2 comprising the amino acid sequence of SEQ ID NO: 19, and
CDR3 comprising the amino acid sequence of SEQ ID NO: 20; and
a light chain variable region that contains
CDR1 comprising the amino acid sequence of SEQ ID NO: 21,
CDR2 comprising an amino acid sequence selected from SEQ ID NOS: 22, 90, 106-115, and 155-157, and
CDR3 comprising the amino acid sequence of SEQ ID NO: 23; or (vi) a heavy chain variable region that contains
CDR1 comprising the amino acid sequence of SEQ ID NO: 18,
CDR2 comprising the amino acid sequence of SEQ ID NO: 19, and
CDR3 comprising the amino acid sequence of SEQ ID NO: 20; and
a light chain variable region that contains
CDR1 comprising the amino acid sequence of SEQ ID NO: 21,
CDR2 comprising the amino acid sequence of SEQ ID NO: 22, and
CDR3 comprising an amino acid sequence selected from SEQ ID NOS: 23, 91-99, and 118-132.

In a further embodiment, the anti-hGDF15 antibody of the present disclosure comprises (i) a heavy chain variable region that contains
CDR1 comprising an amino acid sequence selected from SEQ ID NOS: 18, 38-42, and 149-150,
CDR2 comprising the amino acid sequence of SEQ ID NO: 19, and
CDR3 comprising the amino acid sequence of SEQ ID NO: 20, and
a light chain variable region that contains
CDR1 comprising the amino acid sequence of SEQ ID NO: 21,
CDR2 comprising the amino acid sequence of SEQ ID NO: 22, and
CDR3 comprising the amino acid sequence of SEQ ID NO: 23;

(ii) a heavy chain variable region that contains
CDR1 comprising the amino acid sequence of SEQ ID NO: 18,
CDR2 comprising an amino acid sequence selected from SEQ ID NOS: 19, 45-48, 52-66, and 151-152, and
CDR3 comprising the amino acid sequence of SEQ ID NO: 20, and
a light chain variable region that contains

CDR1 comprising the amino acid sequence of SEQ ID NO: 21,
CDR2 comprising the amino acid sequence of SEQ ID NO: 22, and
CDR3 comprising the amino acid sequence of SEQ ID NO: 23;

(iii) a heavy chain variable region that contains
CDR1 comprising the amino acid sequence of SEQ ID NO: 18,
CDR2 comprising the amino acid sequence of SEQ ID NO: 19, and
CDR3 comprising an amino acid sequence selected from SEQ ID NOS: 20, 71, 73, 77, and 79, and
a light chain variable region that contains
CDR1 comprising the amino acid sequence of SEQ ID NO: 21,
CDR2 comprising the amino acid sequence of SEQ ID NO: 22, and
CDR3 comprising the amino acid sequence of SEQ ID NO: 23;

(iv) a heavy chain variable region that contains
CDR1 comprising the amino acid sequence of SEQ ID NO: 18,
CDR2 comprising the amino acid sequence of SEQ ID NO: 19, and
CDR3 comprising the amino acid sequence of SEQ ID NO: 20; and
a light chain variable region that contains
CDR1 comprising an amino acid sequence selected from SEQ ID NOS: 21, 81-83, 85-89, 100-104, and 154,
CDR2 comprising the amino acid sequence of SEQ ID NO: 22, and
CDR3 comprising the amino acid sequence of SEQ ID NO: 23;

(v) a heavy chain variable region that contains
CDR1 comprising the amino acid sequence of SEQ ID NO: 18,
CDR2 comprising the amino acid sequence of SEQ ID NO: 19, and
CDR3 comprising the amino acid sequence of SEQ ID NO: 20; and
a light chain variable region that contains
CDR1 comprising the amino acid sequence of SEQ ID NO: 21,
CDR2 comprising an amino acid sequence selected from SEQ ID NOS: 22, 90, 106, 108-111, 113-115, and 155-157, and
CDR3 comprising the amino acid sequence of SEQ ID NO: 23; or (vi) a heavy chain variable region that contains
CDR1 comprising the amino acid sequence of SEQ ID NO: 18,
CDR2 comprising the amino acid sequence of SEQ ID NO: 19, and
CDR3 comprising the amino acid sequence of SEQ ID NO: 20; and
a light chain variable region that contains
CDR1 comprising the amino acid sequence of SEQ ID NO: 21,
CDR2 comprising the amino acid sequence of SEQ ID NO: 22, and
CDR3 comprising an amino acid sequence selected from SEQ ID NOS: 23, 93, 95-99, 121, 122, 124, 125, 131, and 132.

In a further embodiment, the anti-hGDF15 antibody of the present disclosure comprises a heavy chain variable region that contains CDR1 comprising the amino acid sequence of SEQ ID NO: 137 or an amino acid sequence that differs from the amino acid sequence of SEQ ID NO: 137 by having amino acid modification of one to three amino acid residues, CDR2 comprising the amino acid sequence of SEQ ID NO: 138 or an amino acid sequence that differs from the amino acid sequence of SEQ ID NO: 138 by having amino acid modification of one to three amino acid residues, and CDR3 comprising the amino acid sequence of SEQ ID NO: 139 or an amino acid sequence that differs from the amino acid sequence of SEQ ID NO: 139 by having amino acid modification of one to three amino acid residues; and a light chain variable region that contains CDR1 comprising the amino acid sequence of SEQ ID NO: 140 or an amino acid sequence that differs from the amino acid sequence of SEQ ID NO: 140 by having amino acid modification of one to three amino acid residues, CDR2 comprising the amino acid sequence of SEQ ID NO: 141 or an amino acid sequence that differs from the amino acid sequence of SEQ ID NO: 141 by having amino acid modification of one to three amino acid residues, and CDR3 comprising the amino acid sequence of SEQ ID NO: 142 or an amino acid sequence that differs from the amino acid sequence of SEQ ID NO: 142 by having amino acid modification of one to three amino acid residues.

In a further embodiment, the anti-hGDF15 antibody of the present disclosure comprises a heavy chain variable region that contains CDR1 comprising the amino acid sequence of SEQ ID NO: 143 or an amino acid sequence that differs from the amino acid sequence of SEQ ID NO: 143 by having amino acid modification of one to three amino acid residues, CDR2 comprising the amino acid sequence of SEQ ID NO: 144 or an amino acid sequence that differs from the amino acid sequence of SEQ ID NO: 144 by having amino acid modification of one to three amino acid residues, and CDR3 comprising the amino acid sequence of SEQ ID NO: 145 or an amino acid sequence that differs from the amino acid sequence of SEQ ID NO: 145 by having amino acid modification of one to three amino acid residues; and a light chain variable region that contains CDR1 comprising the amino acid sequence of SEQ ID NO: 146 or an amino acid sequence that differs from the amino acid sequence of SEQ ID NO: 146 by having amino acid modification of one to three amino acid residues, CDR2 comprising the amino acid sequence of SEQ ID NO: 147 or an amino acid sequence that differs from the amino acid sequence of SEQ ID NO: 147 by having amino acid modification of one to three amino acid residues, and CDR3 comprising the amino acid sequence of SEQ ID NO: 148 or an amino acid sequence that differs from the amino acid sequence of SEQ ID NO: 148 by having amino acid modification of one to three amino acid residues.

In a further embodiment, the anti-hGDF15 antibody of the present disclosure comprises a heavy chain variable region comprising an amino acid sequence having 80%, 85%, 90%, 95%, or more sequence identity to the amino acid sequence of SEQ ID NO: 8, or the amino acid sequence of SEQ ID NO: 8 or an amino acid sequence that differs from the amino acid sequence of SEQ ID NO: 8 by having amino acid modification of 1 to 20, 1 to 15, 1 to 10, 1 to 5, or 1 to 3 amino acid residues; and a light chain variable region comprising an amino acid sequence having 80%, 85%, 90%, 95%, or more sequence identity to the amino acid sequence of SEQ ID NO: 9, or the amino acid sequence of SEQ ID NO: 9 or an amino acid sequence that differs from the amino acid sequence of SEQ ID NO: 9 by having amino acid modification of 1 to 20, 1 to 15, 1 to 10, 1 to 5, or 1 to 3 amino acid residues.

In a further embodiment, the anti-hGDF15 antibody of the present disclosure comprises a heavy chain variable region comprising the amino acid sequence of SEQ ID NO: 8 or an amino acid sequence that differs from the amino acid sequence of SEQ ID NO: 8 by having amino acid substitution selected from H48R, H49R, H49D, H50R, H50S, H50F, H52R, H52Q, H72R, H73D, H73R, H73Y, H119R, H119F, H48S, H71Y, H72A, H72L, H72N, H72T, H72W, H75H, H75L, H75N, H75Q, H79H, H79K, H79Q, H79R, H83R, H117Q, H119E, H119H, H119K, H119N, H119Q, H119S, H119T, H120A, H120D, H120F, H120N, H120Q, H122F, H54T, H54N, H71R, H71H, and H71I, and a light chain variable region comprising the amino acid sequence of SEQ ID NO: 9 or an amino acid sequence that differs from the amino acid sequence of SEQ ID NO: 9 by having amino acid substitution selected from L47R, L48E, L48R, L48S, L48K, L50D, L50R, L50F, L50Y, L73R, L111F, L111Y, L112E, L112R, L112D, L112F, L113D, L113R, L113F, L48H, L48Y, L50Q, L50W, L51Q, L69Y, L70F, L70H, L72D, L72E, L72R, L72Y, L73K, L73N, L73Y, L75Q, L87K, L87N, L111A, L111N, L111S, L112H, L112Q, L112T, L112Y, L113S, L114F, L114H, L114I, L114N, L114Y, L116H, L116Y, L51Y, L72F, L73Q, and L74H.

In a further embodiment, the anti-hGDF15 antibody of the present disclosure comprises a heavy chain variable region comprising the amino acid sequence of SEQ ID NO: 8 or an amino acid sequence that differs from the amino acid sequence of SEQ ID NO: 8 by having amino acid substitution selected from H49R, H49D, H50R, H50S, H50F, H73D, H73R, H73Y, H48S, H71Y, H72A, H72L, H72N, H72T, H72W, H75H, H75L, H75N, H75Q, H79H, H79K, H79Q, H79R, H83R, H119N, H119S, H120F, H120Q, H54T, H54N, H71R, and H71H, and a light chain variable region comprising the amino acid sequence of SEQ ID NO: 9 or an amino acid sequence that differs from the amino acid sequence of SEQ ID NO: 9 by having amino acid substitution selected from L47R, L48E, L48R, L48K, L50D, L50R, L50F, L50Y, L73R, L112E, L112D, L112F, L113D, L113R, L113F, L48H, L48Y, L50Q, L50W, L51Q, L70F, L72D, L72E, L72R, L72Y, L73N, L73Y, L75Q, L112H, L112Q, L112Y, L113S, L116H, L116Y, L51Y, L72F, L73Q, and L74H.

In a further embodiment, the anti-hGDF15 antibody of the present disclosure comprises a heavy chain variable region comprising the amino acid sequence of SEQ ID NO: 8 or an amino acid sequence that differs from the amino acid sequence of SEQ ID NO: 8 by having amino acid substitution selected from H49R, H49D, H48S, H71Y, H83R, and H120F, and a light chain variable region comprising the amino acid sequence of SEQ ID NO: 9 or an amino acid sequence that differs from the amino acid sequence of SEQ ID NO: 9 by having amino acid substitution selected from L48K, L112D, L72F, and L74H.

In the above embodiments, the amino acid substitution is indicated by an abbreviation representing heavy (H) or light (L) chain, the number representing its position, and an abbreviation representing the amino acid residue after substitution. For example, "H48R" means substitution to an arginine residue at position 48 of the heavy chain.

In a further embodiment, the anti-hGDF15 antibody of the present disclosure comprises a heavy chain variable region comprising the amino acid sequence of SEQ ID NO: 8 and a light chain variable region comprising the amino acid sequence of SEQ ID NO: 9.

In a further embodiment, the anti-hGDF15 antibody of the present disclosure comprises a heavy chain variable region comprising an amino acid sequence having 80%, 85%, 90%, 95%, or more sequence identity to the amino acid sequence of SEQ ID NO: 4, or the amino acid sequence of SEQ ID NO: 4 or an amino acid sequence that differs from the amino acid sequence of SEQ ID NO: 4 by having amino acid modification of 1 to 20, 1 to 15, 1 to 10, 1 to 5, or 1 to 3 amino acid residues;

and a light chain variable region comprising an amino acid sequence having 80%, 85%, 90%, 95%, or more sequence identity to the amino acid sequence of SEQ ID NO: 5, or the amino acid sequence of SEQ ID NO: 5 or an amino acid sequence that differs from the amino acid sequence of SEQ ID NO: 5 by having amino acid modification of 1 to 20, 1 to 15, 1 to 10, 1 to 5, or 1 to 3 amino acid residues;

a heavy chain variable region comprising an amino acid sequence having 80%, 85%, 90%, 95%, or more sequence identity to the amino acid sequence of SEQ ID NO: 6, or the amino acid sequence of SEQ ID NO: 6 or an amino acid sequence that differs from the amino acid sequence of SEQ ID NO: 6 by having amino acid modification of 1 to 20, 1 to 15, 1 to 10, 1 to 5, or 1 to 3 amino acid residues;

and a light chain variable region comprising an amino acid sequence having 80%, 85%, 90%, 95%, or more sequence identity to the amino acid sequence of SEQ ID NO: 7, or the amino acid sequence of SEQ ID NO: 7 or an amino acid sequence that differs from the amino acid sequence of SEQ ID NO: 7 by having amino acid modification of 1 to 20, 1 to 15, 1 to 10, 1 to 5, or 1 to 3 amino acid residues;

a heavy chain variable region comprising an amino acid sequence having 80%, 85%, 90%, 95%, or more sequence identity to the amino acid sequence of SEQ ID NO: 133, or the amino acid sequence of SEQ ID NO: 133 or an amino acid sequence that differs from the amino acid sequence of SEQ ID NO: 133 by having amino acid modification of 1 to 20, 1 to 15, 1 to 10, 1 to 5, or 1 to 3 amino acid residues;

and a light chain variable region comprising an amino acid sequence having 80%, 85%, 90%, 95%, or more sequence identity to the amino acid sequence of SEQ ID NO: 134, or the amino acid sequence of SEQ ID NO: 134 or an amino acid sequence that differs from the amino acid sequence of SEQ ID NO: 134 by having amino acid modification of 1 to 20, 1 to 15, 1 to 10, 1 to 5, or 1 to 3 amino acid residues; or a heavy chain variable region comprising an amino acid sequence having 80%, 85%, 90%, 95%, or more sequence identity to the amino acid sequence of SEQ ID NO: 135, or the amino acid sequence of SEQ ID NO: 135 or an amino acid sequence that differs from the amino acid sequence of SEQ ID NO: 135 by having amino acid modification of 1 to 20, 1 to 15, 1 to 10, 1 to 5, or 1 to 3 amino acid residues;

and a light chain variable region comprising an amino acid sequence having 80%, 85%, 90%, 95%, or more sequence identity to the amino acid sequence of SEQ ID NO: 136, or the amino acid sequence of SEQ ID NO: 136 or an amino acid sequence that differs from the amino acid sequence of SEQ ID NO: 136 by having amino acid modification of 1 to 20, 1 to 15, 1 to 10, 1 to 5, or 1 to 3 amino acid residues.

As used herein, the amino acid modification includes amino acid deletion, substitution, insertion, and addition. The modification may be any one of, or a combination of two or more of, deletion, substitution, insertion, and addition. The number of modifications can be, but not limited to, 1 to 20, 1 to 15, 1 to 10, 1 to 5, or 1 to 3. In an embodiment, the amino acid modification is amino acid substitution. In a further embodiment, the amino acid modification is modification of one to three amino acid residues. In a further embodiment, the amino acid modification is amino acid substitution of one amino acid.

As used herein, an amino acid sequence that "comprises" a given amino acid sequence includes an amino acid sequence comprising the given amino acid sequence and one or more amino acid residues added to the given amino acid sequence, and an amino acid sequence consisting of the given amino acid sequence.

As used herein, a heavy or light chain variable region comprising an amino acid sequence having 80%, 85%, 90%, 95%, or more sequence identity to the amino acid sequence of a given heavy or light chain variable region, and a heavy or light chain variable region comprising an amino acid sequence that differs from the amino acid sequence of a given heavy or light chain variable region by having amino acid modification of 1 to 20, 1 to 15, 1 to 10, 1 to 5, or 1 to 3 amino acid residues includes a heavy or light chain variable region in which the CDRs in the amino acid sequence of the given heavy or light chain variable are not modified.

As used herein, "sequence identity" with respect to an amino acid sequence refers to a proportion of amino acid residues that match between the sequence and a sequence to be compared that are optimally aligned (i.e., alighted such that the two sequences are maximally matched) over the entire region of the sequences. The sequences may have an addition or deletion (eg, gap) in the optimal alignment of the two sequences. The sequence identity can be calculated using programs such as FASTA, BLAST, and CLUSTAL W provided in public databases (eg, DDBJ (ddbj.nig.ac.jp)). Alternatively, the sequence identity can also be obtained using a commercially available sequence analysis software (eg, Vector NTI® software, GENETYX® ver. 12).

Various methods are known to obtain an antibody having a desired property by modifying its amino acid sequence. For example, variants with improved binding affinity can be obtained by a method based on phage display. In this method, the site to which mutation is introduced is determined by identifying amino acid residues that affect the interaction between the antibody and the antigen by the alanine scanning mutagenesis method, or by identifying the contact point between the antibody and the antigen by analyzing the crystal structure of the antigen-antibody complex. A variant having a desired property can be obtained by preparing variants in which the amino acid of the site thus identified is modified, by error-prone PCR or site-specific mutagenesis for example, and screening the library of the obtained variants.

The antibody of the present disclosure has an effect of lowering blood GDF15 concentration. Whether an antibody has such an effect can be confirmed by evaluating whether the antibody significantly reduces blood GDF15 concentration in an animal to which GDF15-expressing cancer cells are transplanted as compared with a control antibody, as described in Examples. Without being bound by any theory, the antibody of the present disclosure is considered to reduce blood GDF15 concentration by suppressing cleavage of pro GDF15. The antibody of the present disclosure may also bind to mature GDF15 and has an effect of inhibiting signal transduction from GDF15.

The antibody of the present disclosure can have an effect of improving a symptom such as weight loss, loss of appetite, or circadian rhythm disorder by lowering blood GDF15 concentration (in some cases, further by inhibiting signal transduction of GDF15).

For the antibody, a subclass of immunoglobulin may be selected, or the amino acid sequence or sugar chain in the Fc region may be modified, for the regulation of antibody-dependent cellular cytotoxicity (ADCC) activity, complement-dependent cytotoxicity (CDC) activity or pharmacokinetics, o. For example, IgG4 may be selected for the purpose of reducing capacity of complement activation. In addition, modification that reduces or enhances the binding to an Fc receptor or C1q, or modification that increases the binding affinity to FcRn to prolong half-life in blood may be made.

The antibody also may be bound to a polymer such as polyethylene glycol (PEG), polypropylene glycol, polyoxyalkylene, or a copolymer of polyethylene glycol and polypropylene glycol, for the purpose of prolonging half-life in blood or improving stability of the antibody, for example.

The antibody may also be bound to a substance such as a chemotherapeutic agent, toxic peptide, or radioisotope. Examples of chemotherapeutic agents include alkylating agents such as cisplatin, carboplatin, oxaliplatin, mechloretamine, cyclophosphamide, chlorambusyl, and iphosphamide; metabolic antagonists such as azathiopurine and mercaptopurine; vincaalkaloids (eg, vincristine, vinblastine, vinorelbine and vindesine), alkaloids such as taxan (eg, paclitaxel, docetaxel), etoposide and teniposide; topoisomerase inhibitors such as camptothecin (eg, irinotecan and topotecan); and cytotoxic antibiotics such as actinomycin, anthracycline, doxorubicin, daunorubicin, valrubicin, idarubicin, epirubicin, bleomycin, plicamycin and mitomycin.

The antibody of the present disclosure can be used as an active ingredient of a pharmaceutical composition. The antibody of the present disclosure has an effect of lowering blood GDF15 concentration (in some cases, further has an effect of inhibiting signal transduction of GDF15), and are useful for treating a disease or symptom associated with GDF15. Examples of diseases or symptoms associated with GDF15 include weight loss, loss of appetite, muscle loss, decreased activity, circadian rhythm disorder, abnormal pituitary hormone secretion, thermoregulatory dysfunction, cachexia, cancer, diabetes, kidney failure, heart failure, AIDS, COPD, multiple sclerosis, rheumatoid arthritis, sepsis, tuberculosis, sarcopenia, cancer bone metastasis, anticancer drug-induced nausea and vomiting, hyperemesis gravidarum, chronic myeloproliferative disorders (eg, myelofibrosis, polycythemia vera, essential plateletemia), anorexia nervosa, bipolar disorder, mitochondrial disease, and ICU-related muscle weakness.

In an embodiment, the cachexia is cachexia associated with cancer, diabetes, kidney failure, heart failure, AIDS, COPD, multiple sclerosis, rheumatoid arthritis, sepsis, or tuberculosis. In a further embodiment, the cachexia is cancer cachexia. The treatment of cachexia includes amelioration of one or more symptoms selected from weight loss, loss of appetite, muscle loss, decreased activity, circadian rhythm disorder, abnormal pituitary hormone secretion, and thermoregulatory dysfunction.

Examples of cancers include, but are not limited to, gastric cancer, esophageal cancer, colon cancer, lung cancer, pancreatic cancer, kidney cancer, prostate cancer, ovarian cancer, breast cancer, cervical cancer, uterine body cancer, testicular cancer, bladder cancer, thyroid cancer, hepatocellular carcinoma, intrahepatic bile duct cancer, head and neck cancer, leukemia, multiple myeloma, lymphoma, brain tumor, glioma, and melanoma.

The antibody of the present disclosure is administered to a subject in an amount capable of exerting a desired effect (eg, treatment of a disease or symptom associated with GDF15) (referred to herein as an effective amount). The dose of the antibody is appropriately selected depending on factors such as its administration method and age, body weight, and health condition of the subject. For example, the antibody may be administered at 10 µg/kg to 100 mg/kg, 100 µg/kg to 10 mg/kg, or 1 mg/kg to 10 mg/kg per day for an adult daily, once every few days, once a week, once every few weeks, once a month, or once every few months, although the antibody may be administered differently. The method of administering the antibody is also appropriately selected depending on factors such as age, weight, and health condition of the subject. The administration method may be oral administration or parenteral administration, and parenteral administration is preferred. Examples of parenteral administration include subcutaneous administration, intradermal administration, intramuscular administration, and intravenous administration, and intravenous administration is preferred.

As used herein, the "subject" is a mammal. Examples of mammals include, but are not limited to, mice, rats, rabbits, cats, dogs, sheep, pigs, horses, cows, monkeys, and humans. In an embodiment, the subject is a human.

The pharmaceutical composition can be formulated by conventional methods. In addition to the antibody, the pharmaceutical composition may comprise a pharmaceutically acceptable carrier or additive, such as sterile water, saline, stabilizer, excipient, antioxidant, buffering agent, preservative, surfactant, chelating agent, or binder.

The antibody of the present disclosure may be used in combination with a different therapeutic agent. In the present specification, when two or more of active ingredients are used in combination, all or part of the active ingredients may be contained in a single composition, or all the agents may be separately contained in different compositions. The administration schedules of the two or more active ingredients may be the same or different.

In an embodiment, the antibody of the present disclosure is used in combination with a cancer therapeutic agent.

Examples of cancer therapeutic agents include, but are not limited to, alkylating agents such as cisplatin, carboplatin, oxaliplatin, mechloretamine, cyclophosphamide, chlorambusyl, and ifosfamide; metabolic antagonists such as azathiopurine and mercaptopurine; vincaalkaloids (eg, vincristine, vinblastine, vinorelbine and vindesine), alkaloids such as taxan (eg, paclitaxel, docetaxel), etoposide and teniposide; topoisomerase inhibitors such as camptothecin (eg, irinotecan and topotecan); and cytotoxic antibiotics such as actinomycin, anthracycline, doxorubicin, daunorubicin, valrubicin, idarubicin, epirubicin, bleomycin, plicamycin and mitomycin; molecular targeting agents such as EGFR inhibitors, HER2 inhibitors, ALK inhibitors, and VEGFR inhibitors; immune checkpoint inhibitors such as anti-PD-1 antibodies, anti-PD-L1 antibodies.

Exemplary embodiments of the present disclosure are described below.

[1] An anti-hGDF15 antibody, wherein the antibody binds to an epitope of hGDF15 comprising the amino acid sequence of DHCPLGPGRCCRLH (SEQ ID NO: 3).

[2] The antibody of item 1, wherein the antibody comprises a heavy chain variable region that contains CDR1 contained in a heavy chain variable region comprising the amino acid sequence of SEQ ID NO: 4, or CDR1 consisting of an amino acid sequence that differs from the amino acid sequence of the CDR1 contained in the heavy chain variable region comprising the amino acid sequence of SEQ ID NO: 4 by having amino acid modification of one to three amino acid residues, CDR2 contained in a heavy chain variable region comprising the amino acid sequence of SEQ ID NO: 4, or CDR2 consisting of an amino acid sequence that differs from the amino acid sequence of the CDR2 contained in the heavy chain variable region comprising the amino acid sequence of SEQ ID NO: 4 by having amino acid modification of one to three amino acid residues, and CDR3 contained in a heavy chain variable region comprising the amino acid sequence of SEQ ID NO: 4, or CDR3 consisting of an amino acid sequence that differs from the amino acid sequence of the CDR3 contained in the heavy chain variable region comprising the amino acid sequence of SEQ ID NO: 4 by having amino acid modification of one to three amino acid residues; and a light chain variable region that contains CDR1 contained in a light chain variable region comprising the amino acid sequence of SEQ ID NO: 5, or CDR1 consisting of an amino acid sequence that differs from the amino acid sequence of the CDR1 contained in the light chain variable region comprising the amino acid sequence of SEQ ID NO: 5 by having amino acid modification of one to three amino acid residues, CDR2 contained in a light chain variable region comprising the amino acid sequence of SEQ ID NO: 5, or CDR2 consisting of an amino acid sequence that differs from the amino acid sequence of the CDR2 contained in the light chain variable region comprising the amino acid sequence of SEQ ID NO: 5 by having amino acid modification of one to three amino acid residues, and CDR3 contained in a light chain variable region comprising the amino acid sequence of SEQ ID NO: 5, or CDR3 consisting of an amino acid sequence that differs from the amino acid sequence of the CDR3 contained in the light chain variable region comprising the amino acid sequence of SEQ ID NO: 5 by having amino acid modification of one to three amino acid residues.

[3] The antibody of item 1 or 2, wherein the antibody comprises a heavy chain variable region that contains CDR1 comprising the amino acid sequence of SEQ ID NO: 18 or an amino acid sequence that differs from the amino acid sequence of SEQ ID NO: 18 by having amino acid modification of one to three amino acid residues, CDR2 comprising the amino acid sequence of SEQ ID NO: 19 or an amino acid sequence that differs from the amino acid sequence of SEQ ID NO: 19 by having amino acid modification of one to three amino acid residues, and CDR3 comprising the amino acid sequence of SEQ ID NO: 20 or an amino acid sequence that differs from the amino acid sequence of SEQ ID NO: 20 by having amino acid modification of one to three amino acid residues; and a light chain variable region that contains CDR1 comprising the amino acid sequence of SEQ ID NO: 21 or an amino acid sequence that differs from the amino acid sequence of SEQ ID NO: 21 by having amino acid modification of one to three amino acid residues, CDR2 comprising the amino acid sequence of SEQ ID NO: 22 or an amino acid sequence that differs from the amino acid sequence of SEQ ID NO: 22 by having amino acid modification of one to three amino acid residues, and CDR3 comprising the amino acid sequence of SEQ ID NO: 23 or an amino acid sequence that differs from the amino acid sequence of SEQ ID NO: 23 by having amino acid modification of one to three amino acid residues.

[4] An anti-hGDF15 antibody, wherein the antibody comprises a heavy chain variable region that contains CDR1 contained in a heavy chain variable region comprising the amino acid sequence of SEQ ID NO: 4, or CDR1 consisting of an amino acid sequence that differs from the amino acid sequence of the CDR1 contained in the heavy chain variable region comprising the amino acid sequence of SEQ ID NO: 4 by having amino acid modification of one to three amino acid residues, CDR2 contained in a heavy chain variable region comprising the amino acid sequence of SEQ ID NO: 4, or CDR2 consisting of an amino acid sequence that differs from the amino acid sequence of the CDR2 contained in the heavy chain variable region comprising the amino acid sequence of SEQ ID NO: 4 by having amino acid modification of one to three amino acid residues, and CDR3 contained in a heavy chain variable region comprising the amino acid sequence of SEQ ID NO: 4, or CDR3 consisting of an amino acid sequence that differs from the amino acid sequence of the CDR3 contained in the heavy chain variable region comprising the amino acid sequence of SEQ ID NO: 4 by having amino acid modification of one to three amino acid residues; and a light chain variable region that contains CDR1 contained in a light chain variable region comprising the amino acid sequence of SEQ ID NO: 5, or CDR1 consisting of an amino acid sequence that differs from the amino acid sequence of the CDR1 contained in the light chain variable region comprising the amino acid sequence of SEQ ID NO: 5 by having amino acid modification of one to three amino acid residues, CDR2 contained in a light chain variable region comprising the amino acid sequence of SEQ ID NO: 5, or CDR2 consisting of an amino acid sequence that differs from the amino acid sequence of the CDR2 contained in the light chain variable region comprising the amino acid sequence of SEQ ID NO: 5 by having amino acid modification of one to three amino acid residues, and CDR3 contained in a light chain variable region comprising the amino acid sequence of SEQ ID NO: 5, or CDR3 consisting of an amino acid sequence that differs from the amino acid sequence of the CDR3 contained in the light chain variable region comprising the amino acid sequence of SEQ ID NO: 5 by having amino acid modification of one to three amino acid residues.

[5] An anti-hGDF15 antibody, wherein the antibody comprises a heavy chain variable region that contains CDR1 comprising the amino acid sequence of SEQ ID NO: 18 or an amino acid sequence that differs from the amino acid sequence of SEQ ID NO: 18 by having amino acid modification of one to three amino acid residues, CDR2 comprising the amino acid sequence of SEQ ID NO: 19 or an amino acid sequence that differs from the amino acid sequence of SEQ ID NO: 19 by having amino acid modification of one to three amino acid residues, and CDR3 comprising the amino acid sequence of SEQ ID NO: 20 or an amino acid sequence that differs from the amino acid sequence of SEQ ID NO: 20 by having amino acid modification of one to three amino acid residues; and a light chain variable region that contains CDR1 comprising the amino acid sequence of SEQ ID NO: 21 or an amino acid sequence that differs from the amino acid sequence of SEQ ID NO: 21 by having amino acid modification of one to three amino acid residues, CDR2 comprising the amino acid sequence of SEQ ID NO: 22 or an amino acid sequence that differs from the amino acid sequence of SEQ ID NO: 22 by having amino acid modification of one to three amino acid residues, and CDR3 comprising the amino acid sequence of SEQ ID NO: 23 or an amino acid sequence that differs from the amino acid sequence of SEQ ID NO: 23 by having amino acid modification of one to three amino acid residues.

[6] The antibody of any one of items 2 to 5, wherein the amino acid modification of one to three amino acid residues is amino acid modification of one amino acid residue.

[7] The antibody of any one of items 2 to 6, wherein the amino acid modification is amino acid substitution.

[8] The antibody of any one of items 2 to 7, wherein the amino acid modification of one to three amino acid residues is amino acid substitution of one amino acid residue.

[9] The antibody of any one of items 1 to 8, wherein the antibody comprises a heavy chain variable region that contains CDR3 comprising the amino acid sequence of SEQ ID NO: 20.

[10] The antibody of any one of items 1 to 9, wherein the antibody comprises a light chain variable region that contains CDR3 comprising the amino acid sequence of SEQ ID NO: 23.

[11] The antibody of any one of items 1 to 10, wherein the antibody comprises a heavy chain variable region that contains CDR1 comprising an amino acid sequence selected from SEQ ID NOS: 18, 38-44, and 149-150, CDR2 comprising an amino acid sequence selected from SEQ ID NOS: 19, 45-48, 52-66, and 151-153, and CDR3 comprising an amino acid sequence selected from SEQ ID NOS: 20, 49, 50 and 67-80; and a light chain variable region that contains CDR1 comprising an amino acid sequence selected from SEQ ID NOS: 21, 81-89, 100-104, and 154, CDR2 comprising an amino acid sequence selected from SEQ ID NOS: 22, 90, 106-115, and 155-157, and CDR3 comprising an amino acid sequence selected from SEQ ID NOS: 23, 91-99, and 118-132.

[12] The antibody of any one of items 1 to 11, wherein the antibody comprises a heavy chain variable region that contains CDR1 comprising an amino acid sequence selected from SEQ ID NOS: 18, 38-42, and 149-150, CDR2 comprising an amino acid sequence selected from SEQ ID NOS: 19, 46-48, 52-66, and 151-152, and CDR3 comprising an amino acid sequence selected from SEQ ID NOS: 20, 71, 73, 77, and 79; and a light chain variable region that contains CDR1 comprising an amino acid sequence selected from SEQ ID NOS: 21, 81-83, 85-89, 100-104, and 154, CDR2 comprising an amino acid sequence selected from SEQ ID NOS: 22, 90, 106, 108-111, 113-115, and 155-157, and CDR3 comprising an amino acid sequence selected from SEQ ID NOS: 23, 93, 95-99, 121, 122, 124, 125, 131, and 132.

[13] The antibody of any one of items 1 to 12, wherein the antibody comprises a heavy chain variable region that contains CDR1 comprising an amino acid sequence selected from SEQ ID NOS: 18 and 38-44, CDR2 comprising an amino acid sequence selected from SEQ ID NOS: 19, 45-48, and 52-66, and CDR3 comprising an amino acid sequence selected from SEQ ID NOS: 20, 49, 50 and 67-80; and a light chain variable region that contains CDR1 comprising an amino acid sequence selected from SEQ ID NOS: 21, 81-89, and 100-104, CDR2 comprising an amino acid sequence selected from SEQ ID NOS: 22, 90, and 106-115, and CDR3 comprising an amino acid sequence selected from SEQ ID NOS: 23, 91-99, and 118-132.

[14] The antibody of any one of items 1 to 13, wherein the antibody comprises a heavy chain variable region that contains CDR1 comprising an amino acid sequence selected from SEQ ID NOS: 18 and 38-42, CDR2 comprising an amino acid sequence selected from SEQ ID NOS: 19, 46-48, and 52-66, and CDR3 comprising an amino acid sequence selected from SEQ ID NOS: 20, 71, 73, 77, and 79; and a light chain variable region that contains CDR1 comprising an amino acid sequence selected from SEQ ID NOS: 21, 81-83, 85-89, and 100-104, CDR2 comprising an amino acid sequence selected from SEQ ID NOS: 22, 90, 106, 108-111, and 113-115, and CDR3 comprising an amino acid sequence selected from SEQ ID NOS: 23, 93, 95-99, 121, 122, 124, 125, 131 and 132.

[15] The antibody of any one of items 1 to 14, wherein the antibody comprises a heavy chain variable region selected from (1)-(3) and a light chain variable region selected from (4)-(6):

(1) a heavy chain variable region that contains

CDR1 comprising an amino acid sequence selected from SEQ ID NOS: 18, 38-44 and 149-150, CDR2 comprising the amino acid sequence of SEQ ID NO: 19, and CDR3 comprising the amino acid sequence of SEQ ID NO: 20; (2) a heavy chain variable region that contains CDR1 comprising the amino acid sequence of SEQ ID NO: 18, CDR2 comprising an amino acid sequence selected from SEQ ID NOS: 19, 45-48, 52-66, and 151-153, and CDR3 comprising the amino acid sequence of SEQ ID NO: 20; (3) a heavy chain variable region that contains CDR1 comprising the amino acid sequence of SEQ ID NO: 18, CDR2 comprising the amino acid sequence of SEQ ID NO: 19, and CDR3 comprising an amino acid sequence selected from SEQ ID NOS: 20, 49, 50 and 67-80;

(4) a light chain variable region that contains

CDR1 comprising an amino acid sequence selected from SEQ ID NOS: 21, 81-89, 100-104, and 154, CDR2 comprising the amino acid sequence of SEQ ID NO: 22, and CDR3 comprising the amino acid sequence of SEQ ID NOS: 23;

(5) a light chain variable region that contains

CDR1 comprising the amino acid sequence of SEQ ID NO: 21,

CDR2 comprising an amino acid sequence selected from SEQ ID NOS: 22, 90, 106-115, and 155-157, and CDR3 comprising the amino acid sequence of SEQ ID NOS: 23; and (6) a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 91-99, and 118-132.

[16] The antibody of any one of items 1 to 15, wherein the antibody comprises a heavy chain variable region selected from (1)-(3) and a light chain variable region selected from (4)-(6):

(1) a heavy chain variable region that contains

CDR1 comprising an amino acid sequence selected from SEQ ID NOS: 18, 38-42 and 149-150, CDR2 comprising the amino acid sequence of SEQ ID NO: 19, and CDR3 comprising the amino acid sequence of SEQ ID NO: 20;

(2) a heavy chain variable region that contains

CDR1 comprising the amino acid sequence of SEQ ID NO: 18,

CDR2 comprising an amino acid sequence selected from SEQ ID NOS: 19, 46-48, 52-66, and 151-152, and CDR3 comprising the amino acid sequence of SEQ ID NO: 20;

(3) a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from SEQ ID NOS: 20, 71, 73, 77, and 79;

(4) a light chain variable region that contains

CDR1 comprising an amino acid sequence selected from SEQ ID NOS: 21, 81-83, 85-89, 100-104, and 154, CDR2 comprising the amino acid sequence of SEQ ID NO: 22, and CDR3 comprising the amino acid sequence of SEQ ID NOS: 23;

(5) a light chain variable region that contains

CDR1 comprising the amino acid sequence of SEQ ID NO: 21,

CDR2 comprising an amino acid sequence selected from SEQ ID NOS: 22, 90, 106, 108-111, 113-115, and 155-157, and CDR3 comprising the amino acid sequence of SEQ ID NOS: 23; and (6) a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 93, 95-99, 121, 122, 124, 125, 131, and 132.

[17] The antibody of any one of items 1 to 16, wherein the antibody comprises a heavy chain variable region selected from (1)-(3) and a light chain variable region selected from (4)-(6):

(1) a heavy chain variable region that contains

CDR1 comprising an amino acid sequence selected from SEQ ID NOS: 18, 38, and 39

CDR2 comprising the amino acid sequence of SEQ ID NO: 19, and

CDR3 comprising the amino acid sequence of SEQ ID NO: 20; (2) a heavy chain variable region that contains CDR1 comprising the amino acid sequence of SEQ ID NO: 18, CDR2 comprising an amino acid sequence selected from SEQ ID NOS: 19, 52, and 66, and CDR3 comprising the amino acid sequence of SEQ ID NO: 20;

(3) a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from SEQ ID NOS: 20 and 77;

(4) a light chain variable region that contains

CDR1 comprising an amino acid sequence selected from SEQ ID NOS: 21 and 85,

CDR2 comprising the amino acid sequence of SEQ ID NO: 22, and

CDR3 comprising the amino acid sequence of SEQ ID NO: 23;

(5) a light chain variable region that contains

CDR1 comprising the amino acid sequence of SEQ ID NO: 21,

CDR2 comprising an amino acid sequence selected from SEQ ID NOS: 22, 155, and 157, and CDR3 comprising the amino acid sequence of SEQ ID
NO: 23; and
(6) a light chain variable region that contains
CDR1 comprising the amino acid sequence of SEQ ID
NO: 21,
CDR2 comprising the amino acid sequence of SEQ ID
NO: 22, and
CDR3 comprising an amino acid sequence selected from
SEQ ID NOS: 23 and 95.
[18] The antibody of any one of items 1 to 17, wherein the
antibody comprises
(i) a heavy chain variable region that contains
CDR1 comprising an amino acid sequence selected from
SEQ ID NOS: 18, 38-44, and 149-150,
CDR2 comprising the amino acid sequence of SEQ ID
NO: 19, and
CDR3 comprising the amino acid sequence of SEQ ID
NO: 20, and
a light chain variable region that contains
CDR1 comprising the amino acid sequence of SEQ ID
NO: 21,
CDR2 comprising the amino acid sequence of SEQ ID
NO: 22, and
CDR3 comprising the amino acid sequence of SEQ ID
NO: 23;
(ii) a heavy chain variable region that contains
CDR1 comprising the amino acid sequence of SEQ ID
NO: 18,
CDR2 comprising an amino acid sequence selected from
SEQ ID NOS: 19, 45-48, 52-66, and 151-153, and
CDR3 comprising the amino acid sequence of SEQ ID
NO: 20, and
a light chain variable region that contains
CDR1 comprising the amino acid sequence of SEQ ID
NO: 21,
CDR2 comprising the amino acid sequence of SEQ ID
NO: 22, and
CDR3 comprising the amino acid sequence of SEQ ID
NO: 23;
(iii) a heavy chain variable region that contains
CDR1 comprising the amino acid sequence of SEQ ID
NO: 18,
CDR2 comprising the amino acid sequence of SEQ ID
NO: 19, and
CDR3 comprising an amino acid sequence selected from
SEQ ID NOS: 20, 49, 50 and 67-80, and
a light chain variable region that contains
CDR1 comprising the amino acid sequence of SEQ ID
NO: 21,
CDR2 comprising the amino acid sequence of SEQ ID
NO: 22, and
CDR3 comprising the amino acid sequence of SEQ ID
NO: 23;
(iv) a heavy chain variable region that contains
CDR1 comprising the amino acid sequence of SEQ ID
NO: 18,
CDR2 comprising the amino acid sequence of SEQ ID
NO: 19, and
CDR3 comprising the amino acid sequence of SEQ ID
NO: 20; and
a light chain variable region that contains
CDR1 comprising an amino acid sequence selected from
SEQ ID NOS: 21, 81-89, 100-104, and 154,
CDR2 comprising the amino acid sequence of SEQ ID
NO: 22, and
CDR3 comprising the amino acid sequence of SEQ ID
NO: 23;

(v) a heavy chain variable region that contains
CDR1 comprising the amino acid sequence of SEQ ID
NO: 18,
CDR2 comprising the amino acid sequence of SEQ ID
NO: 19, and
CDR3 comprising the amino acid sequence of SEQ ID
NO: 20; and
a light chain variable region that contains
CDR1 comprising the amino acid sequence of SEQ ID
NO: 21,
CDR2 comprising an amino acid sequence selected from
SEQ ID NOS: 22, 90, 106-115, and 155-157, and
CDR3 comprising the amino acid sequence of SEQ ID
NO: 23; or
(vi) a heavy chain variable region that contains
CDR1 comprising the amino acid sequence of SEQ ID
NO: 18,
CDR2 comprising the amino acid sequence of SEQ ID
NO: 19, and
CDR3 comprising the amino acid sequence of SEQ ID
NO: 20; and
a light chain variable region that contains
CDR1 comprising the amino acid sequence of SEQ ID
NO: 21,
CDR2 comprising the amino acid sequence of SEQ ID
NO: 22, and
CDR3 comprising an amino acid sequence selected from
SEQ ID NOS: 23, 91-99, and 118-132.
[19] The antibody of any one of items 1 to 18, wherein the
antibody comprises
(i) a heavy chain variable region that contains
CDR1 comprising an amino acid sequence selected from
SEQ ID NOS: 18, 38-42, and 149-150,
CDR2 comprising the amino acid sequence of SEQ ID
NO: 19, and
CDR3 comprising the amino acid sequence of SEQ ID
NO: 20, and
a light chain variable region that contains
CDR1 comprising the amino acid sequence of SEQ ID
NO: 21,
CDR2 comprising the amino acid sequence of SEQ ID
NO: 22, and
CDR3 comprising the amino acid sequence of SEQ ID
NO: 23;
(ii) a heavy chain variable region that contains
CDR1 comprising the amino acid sequence of SEQ ID
NO: 18,
CDR2 comprising an amino acid sequence selected from
SEQ ID NOS: 19, 45-48, 52-66, and 151-152, and
CDR3 comprising the amino acid sequence of SEQ ID
NO: 20, and
a light chain variable region that contains
CDR1 comprising the amino acid sequence of SEQ ID
NO: 21,
CDR2 comprising the amino acid sequence of SEQ ID
NO: 22, and
CDR3 comprising the amino acid sequence of SEQ ID
NO: 23;
(iii) a heavy chain variable region that contains
CDR1 comprising the amino acid sequence of SEQ ID
NO: 18,
CDR2 comprising the amino acid sequence of SEQ ID
NO: 19, and
CDR3 comprising an amino acid sequence selected from
SEQ ID NOS: 20, 71, 73, 77, and 79, and
a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(iv) a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising an amino acid sequence selected from SEQ ID NOS: 21, 81-83, 85-89, 100-104, and 154, CDR2 comprising the amino acid sequence of SEQ ID NO: 22, and CDR3 comprising the amino acid sequence of SEQ ID NO: 23;

(v) a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising the amino acid sequence of SEQ ID NO: 21, CDR2 comprising an amino acid sequence selected from SEQ ID NOS: 22, 90, 106, 108-111, 113-115, and 155-157, and CDR3 comprising the amino acid sequence of SEQ ID NO: 23; or (vi) a heavy chain variable region that contains CDR1 comprising the amino acid sequence of SEQ ID NO: 18, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 93, 95-99, 121, 122, 124, 125, 131, and 132.

[20] The antibody of any one of items 1 to 19, wherein the antibody comprises (i) a heavy chain variable region that contains CDR1 comprising an amino acid sequence selected from SEQ ID NOS: 18 and 38-44, CDR2 comprising the amino acid sequence of SEQ ID NO: 19, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(ii) a heavy chain variable region that contains

CDR1 comprising the amino acid sequence of SEQ ID NO: 18,

CDR2 comprising an amino acid sequence selected from SEQ ID NOS: 19, 45-48, and 52-66, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(iii) a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from SEQ ID NOS: 20, 49, 50 and 67-80, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(iv) a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising an amino acid sequence selected from SEQ ID NOS: 21, 81-89, and 100-104, CDR2 comprising the amino acid sequence of SEQ ID NO: 22, and CDR3 comprising the amino acid sequence of SEQ ID NO: 23;

(v) a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising the amino acid sequence of SEQ ID NO: 21, CDR2 comprising an amino acid sequence selected from SEQ ID NOS: 22, 90, and 106-115, and CDR3 comprising the amino acid sequence of SEQ ID NO: 23; or (vi) a heavy chain variable region that contains CDR1 comprising the amino acid sequence of SEQ ID NO: 18, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 91-99, and 118-132.

[21] The antibody of any one of items 1 to 20, wherein the antibody comprises (i) a heavy chain variable region that contains CDR1 comprising an amino acid sequence selected from SEQ ID NOS: 18 and 38-42, CDR2 comprising the amino acid sequence of SEQ ID NO: 19, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(ii) a heavy chain variable region that contains

CDR1 comprising the amino acid sequence of SEQ ID NO: 18,

CDR2 comprising an amino acid sequence selected from SEQ ID NOS: 19, 46-48, and 52-66, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(iii) a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from SEQ ID NOS: 20, 71, 73, 77, and 79, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(iv) a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising an amino acid sequence selected from SEQ ID NOS: 21, 81-83, 85-89, and 100-104, CDR2 comprising the amino acid sequence of SEQ ID NO: 22, and CDR3 comprising the amino acid sequence of SEQ ID NO: 23;

(v) a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising the amino acid sequence of SEQ ID NO: 21, CDR2 comprising an amino acid sequence selected from SEQ ID NOS: 22, 90, 106, 108-111, and 113-115, and CDR3 comprising the amino acid sequence of SEQ ID NO: 23; or (vi) a heavy chain variable region that contains CDR1 comprising the amino acid sequence of SEQ ID NO: 18, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising an amino acid sequence selected from SEQ ID NOS: 23, 93, 95-99, 121, 122, 124, 125, 131 and 132.

[22] The antibody of any one of items 1 to 21, wherein the antibody comprises a heavy chain variable region that contains CDR1 comprising the amino acid sequence of SEQ ID NO: 18, CDR2 comprising the amino acid sequence of SEQ ID NO: 19, and CDR3 comprising the amino acid sequence of SEQ ID NO: 20, and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23.

[23] The antibody of any one of items 1 to 22, wherein the antibody comprises CDR1, CDR2, and CDR3 contained in a heavy chain variable region comprising the amino acid sequence of SEQ ID NO: 4, and CDR1, CDR2, and CDR3 contained in a light chain variable region comprising the amino acid sequence of SEQ ID NO: 5.

[24] The antibody of item 1, wherein the antibody comprises a heavy chain variable region that contains CDR1 contained in a heavy chain variable region comprising the amino acid sequence of SEQ ID NO: 133, or CDR1 consisting of an amino acid sequence that differs from the amino acid sequence of the CDR1 contained in the heavy chain variable region comprising the amino acid sequence of SEQ ID NO: 133 by having amino acid modification of one to three amino acid residues, CDR2 contained in a heavy chain variable region comprising the amino acid sequence of SEQ ID NO: 133, or CDR2 consisting of an amino acid sequence that differs from the amino acid sequence of the CDR2 contained in the heavy chain variable region comprising the amino acid sequence of SEQ ID NO: 133 by having amino acid modification of one to three amino acid residues, and CDR3 contained in a heavy chain variable region comprising the amino acid sequence of SEQ ID NO: 133, or CDR3 consisting of an amino acid sequence that differs from the amino acid sequence of the CDR3 contained in the heavy chain variable region comprising the amino acid sequence of SEQ ID NO: 133 by having amino acid modification of one to three amino acid residues; and a light chain variable region that contains CDR1 contained in a light chain variable region comprising the amino acid sequence of SEQ ID NO: 134, or CDR1 consisting of an amino acid sequence that differs from the amino acid sequence of the CDR1 contained in the light chain variable region comprising the amino acid sequence of SEQ ID NO: 134 by having amino acid modification of one to three amino acid residues, CDR2 contained in a light chain variable region comprising the amino acid sequence of SEQ ID NO: 134, or CDR2 consisting of an amino acid sequence that differs from the amino acid sequence of the CDR2 contained in the light chain variable region comprising the amino acid sequence of SEQ ID NO: 134 by having amino acid modification of one to three amino acid residues, and CDR3 contained in a light chain variable region comprising the amino acid sequence of SEQ ID NO: 134, or CDR3 consisting of an amino acid sequence that differs from the amino acid sequence of the CDR3 contained in the light chain variable region comprising the amino acid sequence of SEQ ID NO: 134 by having amino acid modification of one to three amino acid residues.

[25] The antibody of item 1 or 24, wherein the antibody comprises a heavy chain variable region that contains CDR1 comprising the amino acid sequence of SEQ ID NO: 137 or an amino acid sequence that differs from the amino acid sequence of SEQ ID NO: 137 by having amino acid modification of one to three amino acid residues, CDR2 comprising the amino acid sequence of SEQ ID NO: 138 or an amino acid sequence that differs from the amino acid sequence of SEQ ID NO: 138 by having amino acid modification of one to three amino acid residues, and CDR3 comprising the amino acid sequence of SEQ ID NO: 139 or an amino acid sequence that differs from the amino acid sequence of SEQ ID NO: 139 by having amino acid modification of one to three amino acid residues; and a light chain variable region that contains CDR1 comprising the amino acid sequence of SEQ ID NO: 140 or an amino acid sequence that differs from the amino acid sequence of SEQ ID NO: 140 by having amino acid modification of one to three amino acid residues, CDR2 comprising the amino acid sequence of SEQ ID NO: 141 or an amino acid sequence that differs from the amino acid sequence of SEQ ID NO: 141 by having amino acid modification of one to three amino acid residues, and CDR3 comprising the amino acid sequence of SEQ ID NO: 142 or an amino acid sequence that differs from the amino acid sequence of SEQ ID NO: 142 by having amino acid modification of one to three amino acid residues.

[26] An anti-hGDF15 antibody, wherein the antibody comprises a heavy chain variable region that contains CDR1 contained in a heavy chain variable region comprising the amino acid sequence of SEQ ID NO: 133, or CDR1 consisting of an amino acid sequence that differs from the amino acid sequence of the CDR1 contained in the heavy chain variable region comprising the amino acid sequence of SEQ ID NO: 133 by having amino acid modification of one to three amino acid residues, CDR2 contained in a heavy chain variable region comprising the amino acid sequence of SEQ ID NO: 133, or CDR2 consisting of an amino acid sequence that differs from the amino acid sequence of the CDR2 contained in the heavy chain variable region comprising the amino acid sequence of SEQ ID NO: 133 by having amino acid modification of one to three amino acid residues, and CDR3 contained in a heavy chain variable region comprising the amino acid sequence of SEQ ID NO: 133, or CDR3 consisting of an amino acid sequence that differs from the amino acid sequence of the CDR3 contained in the heavy chain variable region comprising the amino acid sequence of SEQ ID NO: 133 by having amino acid modification of one to three amino acid residues; and a light chain variable region that contains CDR1 contained in a light chain variable region comprising the amino acid sequence of SEQ ID NO: 134, or CDR1 consisting of an amino acid sequence that differs from the amino acid sequence of the CDR1 contained in the light chain variable region comprising the amino acid sequence of SEQ ID NO: 134 by having amino acid modification of one to three amino acid residues, CDR2 contained in a light chain variable region comprising the amino acid sequence of SEQ ID NO: 134, or CDR2 consisting of an amino acid sequence that differs from the amino acid sequence of the CDR2 contained in the light chain variable region comprising the amino acid sequence of SEQ ID NO: 134 by having amino acid modification of one to three amino acid residues, and CDR3 contained in a light chain variable region comprising the amino acid sequence of SEQ ID NO: 134, or CDR3 consisting of an amino acid sequence that differs from the amino acid sequence of the CDR3 contained in the light chain variable region comprising the amino acid sequence of SEQ ID NO: 134 by having amino acid modification of one to three amino acid residues.

[27] An anti-hGDF15 antibody, wherein the antibody comprises a heavy chain variable region that contains CDR1 comprising the amino acid sequence of SEQ ID NO: 137 or an amino acid sequence that differs from the amino acid sequence of SEQ ID NO: 137 by having amino acid modification of one to three amino acid residues, CDR2 comprising the amino acid sequence of SEQ ID NO: 138 or an amino acid sequence that differs from the amino acid sequence of SEQ ID NO: 138 by having amino acid modification of one to three amino acid residues, and CDR3 comprising the amino acid sequence of SEQ ID NO: 139 or an amino acid sequence that differs from the amino acid sequence of SEQ ID NO: 139 by having amino acid modification of one to three amino acid residues; and a light chain variable region that contains CDR1 comprising the amino acid sequence of SEQ ID NO: 140 or an amino acid sequence that differs from the amino acid sequence of SEQ ID NO: 140 by having amino acid modification of one to three amino acid residues, CDR2 comprising the amino acid sequence of SEQ ID NO: 141 or an amino acid sequence that differs from the amino acid sequence of SEQ ID NO: 141 by having amino acid modification of one to three amino acid residues, and CDR3 comprising the amino acid sequence of SEQ ID NO: 142 or an amino acid sequence that differs from the amino acid sequence of SEQ ID NO: 142 by having amino acid modification of one to three amino acid residues.

[28] The antibody of any one of items 24 to 27, wherein the amino acid modification of one to three amino acid residues is amino acid modification of one amino acid residue.

[29] The antibody of item 28, wherein the amino acid modification is amino acid substitution.

[30] The antibody of item 28 or 29, wherein the amino acid modification of one to three amino acid residues is amino acid substitution of one amino acid residue.

[31] The antibody of any one of items 1 and 24 to 30, wherein the antibody comprises a heavy chain variable region that contains CDR3 comprising the amino acid sequence of SEQ ID NO: 139.

[32] The antibody of any one of items 1 and 24 to 31, wherein the antibody comprises a light chain variable region that contains CDR3 comprising the amino acid sequence of SEQ ID NO: 142.

[33] The antibody of any one of items 1 and 24 to 32, wherein the antibody comprises a heavy chain variable region that contains CDR1 comprising the amino acid sequence of SEQ ID NO: 137, CDR2 comprising the amino acid sequence of SEQ ID NO: 138, and CDR3 comprising the amino acid sequence of SEQ ID NO: 139, and a light chain variable region that contains CDR1 comprising the amino acid sequence of SEQ ID NO: 140, CDR2 comprising the amino acid sequence of SEQ ID NO: 141, and CDR3 comprising the amino acid sequence of SEQ ID NO: 142.

[34] The antibody of any one of items 1 and 24 to 33, wherein the antibody comprises CDR1, CDR2, and CDR3 contained in a heavy chain variable region comprising the amino acid sequence of SEQ ID NO: 133, and CDR1, CDR2, and CDR3 contained in a light chain variable region comprising the amino acid sequence of SEQ ID NO: 134.

[35] The antibody of item 1, wherein the antibody comprises a heavy chain variable region that contains CDR1 contained in a heavy chain variable region comprising the amino acid sequence of SEQ ID NO: 135, or CDR1 consisting of an amino acid sequence that differs from the amino acid sequence of the CDR1 contained in the heavy chain variable region comprising the amino acid sequence of SEQ ID NO: 135 by having amino acid modification of one to three amino acid residues, CDR2 contained in a heavy chain variable region comprising the amino acid sequence of SEQ ID NO: 135, or CDR2 consisting of an amino acid sequence that differs from the amino acid sequence of the CDR2 contained in the heavy chain variable region comprising the amino acid sequence of SEQ ID NO: 135 by having amino acid modification of one to three amino acid residues, and CDR3 contained in a heavy chain variable region comprising the amino acid sequence of SEQ ID NO: 135, or CDR3 consisting of an amino acid sequence that differs from the amino acid sequence of the CDR3 contained in the heavy chain variable region comprising the amino acid sequence of SEQ ID NO: 135 by having amino acid modification of one to three amino acid residues; and a light chain variable region that contains CDR1 contained in a light chain variable region comprising the amino acid sequence of SEQ ID NO: 136, or CDR1 consisting of an amino acid sequence that differs from the amino acid sequence of the CDR1 contained in the light chain variable region comprising the amino acid sequence of SEQ ID NO: 136 by having amino acid modification of one to three amino acid residues, CDR2 contained in a light chain variable region comprising the amino acid sequence of SEQ ID NO: 136, or CDR2 consisting of an amino acid sequence that differs from the amino acid sequence of the CDR2 contained in the light chain variable region comprising the amino acid sequence of SEQ ID NO: 136 by having amino acid modification of one to three amino acid residues, and CDR3 contained in a light chain variable region comprising the amino acid sequence of SEQ ID NO: 136, or CDR3 consisting of an amino acid sequence that differs from the amino acid sequence of the CDR3 contained in the light chain variable region comprising the amino acid sequence of SEQ ID NO: 136 by having amino acid modification of one to three amino acid residues.

[36] The antibody of item 1 or 35, wherein the antibody comprises a heavy chain variable region that contains CDR1 comprising the amino acid sequence of SEQ ID NO: 143 or an amino acid sequence that differs from the amino acid sequence of SEQ ID NO: 143 by having amino acid modification of one to three amino acid residues, CDR2 comprising the amino acid sequence of SEQ ID NO: 144 or an amino acid sequence that differs from the amino acid sequence of SEQ ID NO: 144 by having amino acid modification of one to three amino acid residues, and CDR3 comprising the amino acid sequence of SEQ ID NO: 145 or an amino acid sequence that differs from the amino acid sequence of SEQ ID NO: 145 by having amino acid modification of one to three amino acid residues; and a light chain variable region that contains CDR1 comprising the amino acid sequence of SEQ ID NO: 146 or an amino acid sequence that differs from the amino acid sequence of SEQ ID NO: 146 by having amino acid modification of one to three amino acid residues, CDR2 comprising the amino acid sequence of SEQ ID NO: 147 or an amino acid sequence that differs from the amino acid sequence of SEQ ID NO: 147 by having amino acid modification of one to three amino acid residues, and CDR3 comprising the amino acid sequence of SEQ ID NO: 148 or an amino acid sequence that differs from the amino acid sequence of SEQ ID NO: 148 by having amino acid modification of one to three amino acid residues.

[37] An anti-hGDF15 antibody, wherein the antibody comprises a heavy chain variable region that contains CDR1 contained in a heavy chain variable region comprising the amino acid sequence of SEQ ID NO: 135, or CDR1 consisting of an amino acid sequence that differs from the amino acid sequence of the CDR1 contained in the heavy chain variable region comprising the amino acid sequence of SEQ ID NO: 135 by having amino acid modification of one to three amino acid residues, CDR2 contained in a heavy chain variable region comprising the amino acid sequence of SEQ ID NO: 135, or CDR2 consisting of an amino acid sequence that differs from the amino acid sequence of the CDR2 contained in the heavy chain variable region comprising the amino acid sequence of SEQ ID NO: 135 by having amino acid modification of one to three amino acid residues, and CDR3 contained in a heavy chain variable region comprising the amino acid sequence of SEQ ID NO: 135, or CDR3 consisting of an amino acid sequence that differs from the amino acid sequence of the CDR3 contained in the heavy chain variable region comprising the amino acid sequence of SEQ ID NO: 135 by having amino acid modification of one to three amino acid residues; and a light chain variable region that contains CDR1 contained in a light chain variable region comprising the amino acid sequence of SEQ ID NO: 136, or CDR1 consisting of an amino acid sequence that differs from the amino acid sequence of the CDR1 contained in the light chain variable region comprising the amino acid sequence of SEQ ID NO: 136 by having amino acid modification of one to three amino acid residues, CDR2 contained in a light chain variable region comprising the amino acid sequence of SEQ ID NO: 136, or CDR2 consisting of an amino acid sequence that differs from the amino acid sequence of the CDR2 contained in the light chain variable region comprising the amino acid sequence of SEQ ID NO: 136 by having amino acid modification of one to three amino acid residues, and CDR3 contained in a light chain variable region comprising the amino acid sequence of SEQ ID NO: 136, or CDR3 consisting of an amino acid sequence that differs from the amino acid sequence of the CDR3 contained in the light chain variable region comprising the amino acid sequence of SEQ ID NO: 136 by having amino acid modification of one to three amino acid residues.

[38] An anti-hGDF15 antibody, wherein the antibody comprises a heavy chain variable region that contains CDR1 comprising the amino acid sequence of SEQ ID NO: 143 or an amino acid sequence that differs from the amino acid sequence of SEQ ID NO: 143 by having amino acid modification of one to three amino acid residues, CDR2 comprising the amino acid sequence of SEQ ID NO: 144 or an amino acid sequence that differs from the amino acid sequence of SEQ ID NO: 144 by having amino acid modification of one to three amino acid residues, and CDR3 comprising the amino acid sequence of SEQ ID NO: 145 or an amino acid sequence that differs from the amino acid sequence of SEQ ID NO: 145 by having amino acid modification of one to three amino acid residues; and a light chain variable region that contains CDR1 comprising the amino acid sequence of SEQ ID NO: 146 or an amino acid sequence that differs from the amino acid sequence of SEQ ID NO: 146 by having amino acid modification of one to three amino acid residues, CDR2 comprising the amino acid sequence of SEQ ID NO: 147 or an amino acid sequence that differs from the amino acid sequence of SEQ ID NO: 147 by having amino acid modification of one to three amino acid residues, and CDR3 comprising the amino acid sequence of SEQ ID NO: 148 or an amino acid sequence that differs from the amino acid sequence of SEQ ID NO: 148 by having amino acid modification of one to three amino acid residues.

[39] The antibody of any one of items 35 to 38, wherein the amino acid modification of one to three amino acid residues is amino acid modification of one amino acid residue.

[40] The antibody of item 39, wherein the amino acid modification is amino acid substitution.

[41] The antibody of item 39 or 40, wherein the amino acid modification of one to three amino acid residues is amino acid substitution of one amino acid residue.

[42] The antibody of any one of items 1 and 35 to 41, wherein the antibody comprises a heavy chain variable region that contains CDR3 comprising the amino acid sequence of SEQ ID NO: 145.

[43] The antibody of any one of items 1 and 35 to 42, wherein the antibody comprises a light chain variable region that contains CDR3 comprising the amino acid sequence of SEQ ID NO: 148.

[44] The antibody of any one of items 1 and 35 to 43, wherein the antibody comprises a heavy chain variable region that contains CDR1 comprising the amino acid sequence of SEQ ID NO: 143, CDR2 comprising the amino acid sequence of SEQ ID NO: 144, and CDR3 comprising the amino acid sequence of SEQ ID NO: 145, and a light chain variable region that contains CDR1 comprising the amino acid sequence of SEQ ID NO: 146, CDR2 comprising the amino acid sequence of SEQ ID NO: 147, and CDR3 comprising the amino acid sequence of SEQ ID NO: 148.

[45] The antibody of any one of items 1 and 35 to 44, wherein the antibody comprises CDR1, CDR2, and CDR3 contained in a heavy chain variable region comprising the amino acid sequence of SEQ ID NO: 135, and CDR1, CDR2, and CDR3 contained in a light chain variable region comprising the amino acid sequence of SEQ ID NO: 136.

[46] The antibody of any one of items 1 to 45, wherein the antibody comprises a heavy chain variable region comprising an amino acid sequence having 80%, 85%, 90%, 95%, or more sequence identity to the amino acid sequence of SEQ ID NO: 8, or the amino acid sequence of SEQ ID NO: 8 or an amino acid sequence that differs from the amino acid sequence of SEQ ID NO: 8 by having amino acid modification of 1 to 20, 1 to 15, 1 to 10, 1 to 5, or 1 to 3 amino acid residues; and a light chain variable region comprising an amino acid sequence having 80%, 85%, 90%, 95%, or more sequence identity to the amino acid sequence of SEQ ID NO: 9, or the amino acid sequence of SEQ ID NO: 9 or an amino acid sequence that differs from the amino acid sequence of SEQ ID NO: 9 by having amino acid modification of 1 to 20, 1 to 15, 1 to 10, 1 to 5, or 1 to 3 amino acid residues.

[47] An anti-hGDF15 antibody, wherein the antibody comprises a heavy chain variable region comprising an amino acid sequence having 80%, 85%, 90%, 95%, or more sequence identity to the amino acid sequence of SEQ ID NO: 8, or the amino acid sequence of SEQ ID NO: 8 or an amino acid sequence that differs from the amino acid sequence of SEQ ID NO: 8 by having amino acid modification of 1 to 20, 1 to 15, 1 to 10, 1 to 5, or 1 to 3 amino acid residues; and a light chain variable region comprising an amino acid sequence having 80%, 85%, 90%, 95%, or more sequence identity to the amino acid sequence of SEQ ID NO: 9, or the amino acid sequence of SEQ ID NO: 9 or an amino acid sequence that differs from the amino acid sequence of SEQ ID NO: 9 by having amino acid modification of 1 to 20, 1 to 15, 1 to 10, 1 to 5, or 1 to 3 amino acid residues.

[48] The antibody of any one of items 1 to 47, wherein the antibody comprises a heavy chain variable region comprising the amino acid sequence of SEQ ID NO: 8 and a light chain variable region comprising the amino acid sequence of SEQ ID NO: 9.

[49] The antibody of any one of items 1 to 48, wherein the antibody comprises a heavy chain variable region comprising the amino acid sequence of SEQ ID NO: 8 or an amino acid sequence that differs from the amino acid sequence of SEQ ID NO: 8 by having amino acid substitution selected from H48R, H49R, H49D, H50R, H50S, H50F, H52R, H52Q, H72R, H73D, H73R, H73Y, H119R, H119F, H48S, H71Y, H72A, H72L, H72N, H72T, H72W, H75H, H75L, H75N, H75Q, H79H, H79K, H79Q, H79R, H83R, H117Q, H119E, H119H, H119K, H119N, H119Q, H119S, H119T, H120A, H120D, H120F, H120N, H120Q, H122F, H54T, H54N, H71R, H71H, and H71I, and a light chain variable region comprising the amino acid sequence of SEQ ID NO: 9 or an amino acid sequence that differs from the amino acid sequence of SEQ ID NO: 9 by having amino acid substitution selected from L47R, L48E, L48R, L48S, L48K, L50D, L50R, L50F, L50Y, L73R, L111F, L111Y, L112E, L112R, L112D, L112F, L113D, L113R, L113F, L48H, L48Y, L50Q, L50W, L51Q, L69Y, L70F, L70H, L72D, L72E, L72R, L72Y, L73K, L73N, L73Y, L75Q, L87K, L87N, L111A, L111N, L111S, L112H, L112Q, L112T, L112Y, L113S, L114F, L114H, L114I, L114N, L114Y, L116H, L116Y, L51Y, L72F, L73Q, and L74H.

[50] The antibody of any one of items 1 to 49, wherein the antibody comprises a heavy chain variable region comprising the amino acid sequence of SEQ ID NO: 8 or an amino acid sequence that differs from the amino acid sequence of SEQ ID NO: 8 by having amino acid substitution selected from H49R, H49D, H50R, H50S, H50F, H73D, H73R, H73Y, H48S, H71Y, H72A, H72L, H72N, H72T, H72W, H75H, H75L, H75N, H75Q, H79H, H79K, H79Q, H79R, H83R, H119N, H119S, H120F, H120Q, H54T, H54N, H71R, and H71H, and a light chain variable region comprising the amino acid sequence of SEQ ID NO: 9 or an amino acid sequence that differs from the amino acid sequence of SEQ ID NO: 9 by having amino acid substitution selected from L47R, L48E, L48R, L48K, L50D, L50R, L50F, L50Y, L73R, L112E, L112D, L112F, L113D, L113R, L113F, L48H, L48Y, L50Q, L50W, L51Q, L70F, L72D, L72E, L72R, L72Y, L73N, L73Y, L75Q, L112H, L112Q, L112Y, L113S, L116H, L116Y, L51Y, L72F, L73Q, and L74H.

[51] The antibody of any one of items 1 to 50, wherein the antibody comprises a heavy chain variable region comprising the amino acid sequence of SEQ ID NO: 8 or an amino acid sequence that differs from the amino acid sequence of SEQ ID NO: 8 by having amino acid substitution selected from H49R, H49D, H48S, H71Y, H83R, and H120F, and a light chain variable region comprising the amino acid sequence of SEQ ID NO: 9 or an amino acid sequence that differs from the amino acid sequence of SEQ ID NO: 9 by having amino acid substitution selected from L48K, L112D, L72F, and L74H.

[52] The antibody of any one of items 1 to 51, wherein the antibody competes for binding to hGDF15 with an anti-hGDF15 antibody comprising a heavy chain variable region comprising the amino acid sequence of SEQ ID NO: 8 and a light chain variable region comprising the amino acid sequence of SEQ ID NO: 9.

[53] The antibody of any one of items 1 to 52, wherein the antibody is a monoclonal antibody.

[54] An anti-hGDF15 antibody, wherein the antibody competes for binding to hGDF15 with the antibody of any one of items 1 to 53.

[55] The antibody of item 54, wherein the antibody competes with an anti-hGDF15 antibody comprising a heavy chain variable region comprising the amino acid sequence of SEQ ID NO: 8 and a light chain variable region comprising the amino acid sequence of SEQ ID NO: 9.

[56] The antibody of item 54 or 55, wherein the antibody decreases blood GDF15 concentration.

[57] The antibody of any one of items 54 to 56, wherein the antibody suppresses cleavage of pro GDF15.

[58] The antibody of any one of items 54 to 56, wherein the antibody is a monoclonal antibody.

[59] A polynucleotide encoding the antibody of any one of items 1 to 58.

[60] The polynucleotide of item 59, wherein the polynucleotide comprises the nucleic acid sequence of SEQ ID NO: 24 and/or the nucleic acid sequence of SEQ ID NO: 25.

[61] An expression vector comprising the polynucleotide of item 59 or 60.

[62] A transformed cell comprising the polynucleotide of item 59 or 60.

[63] A pharmaceutical composition comprising the antibody of any one of items 1 to 58.

[64] The pharmaceutical composition of item 63, wherein the pharmaceutical composition is for treating a disease or symptom associated with GDF15.

[65] The pharmaceutical composition of item 64, wherein the disease or symptom associated with GDF15 is cancer.

[66] The pharmaceutical composition of item 64, wherein the disease or symptom associated with GDF15 is cachexia.

[67] The pharmaceutical composition of item 66, wherein the cachexia is cancer cachexia.

[68] The pharmaceutical composition of item 63, wherein the pharmaceutical composition is for decreasing blood GDF15 concentration.

[69] The antibody of any one of items 1 to 58 for use in treating a disease or symptom associated with GDF15.

[70] The antibody of any one of items 1 to 58 for use in decreasing blood GDF15 concentration.

[71] A method of treating a disease or symptom associated with GDF15, comprising administering an effective amount of the antibody of any one of items 1 to 58 to a subject in need thereof.

[72] A method of decreasing blood GDF15 concentration, comprising administering an effective amount of the antibody of any one of items 1 to 58 to a subject in need thereof.

[73] Use of the antibody of any one of items 1 to 58 for the manufacture of a medicament for treating a disease or symptom associated with GDF15.

[74] Use of the antibody of any one of items 1 to 58 for the manufacture of a medicament for decreasing blood GDF15 concentration.

The present invention will be further described with reference to the following examples, but is not limited to the examples in any sense.

EXAMPLES

I. Antibody production (1)
A. Preparation of Anti-hGDF15 Antibody
1 Immunization to Animals
Schedule
Day 1; Initial immunization (25 µg/shot/body, AbISCO-100®, ip)
Day 10; Second immunization (25 µg/shot/body, AbISCO-100®, ip)
Day 17; Third immunization (25 µg/shot/body, AbISCO-100®, ip)
Day 21; Titer check
Day 24; Final boost (25 µg/shot/body, AbISCO-100®, ip)
Day 27; Splenectomy, cell fusion
Reagents
Recombinant Human GDF15 (rhGDF15), R&D, 957-GD-025/CF, 25 µg
AbISCO-100® (ISCONOVA)
Animals
3H/HeJ Jms Slc-lpr/lpr (5W, Japan SLC, female)
Procedures
1. Fifty µL of hGDF15 (0.5 mg/mL), 25 µL of AbISCO-100®, and 175 µL of PBS were mixed and administered intraperitoneally to a mouse (initial immunization).
2. Ten and seventeen days after the initial immunization, a hGDF15 solution prepared in the same manner as in the initial immunization was intraperitoneally administered.
3. Twenty-one days after the initial immunization, blood was collected from the tail of the mouse using a capillary blood collection tube, and plasma was obtained by centrifugation.
4. The plasma was diluted 100-fold, 1000-fold, and 10000-fold, and ELISA was performed using a 96-well plate on which hGDF15 was immobilized. It was confirmed that the antibody titer to hGDF15 was increased.

5. Twenty-four days after the initial immunization, a hGDF15 solution prepared in the same manner as in the initial immunization was intraperitoneally administered.
6. Twenty-seven days after the initial immunization, the spleen was removed under anesthesia and cell fusion was performed.

2 Cell Fusion and HAT Selection
Cells
Sp2/0-Ag14 (referred to as Sp2/0 cells herein after, ATCC #CRL-1581)
Subculture not to exceed $3 \times 10^5$ cells/mL
Reagents
DMEM (GIBCO, 10313-021)
FBS (deactivated at 56° C. for 30 minutes)
Penicillin-Streptomycin-Glutamine (Invitrogen, 10378-016)
Insulin (Funakoshi, BT-243), prepared at 10 mg/mL
55 mM 2-Mercaptoethanol(1000×) (Invitrogen, 21985-023)
rIL-6
PBS
Turk's solution
Trypan blue
Red blood cell lysing buffer (SIGMA, R7757)
PEG1500 (Roche, 108014)
HAT Media Supplement (50×) Hybri-Max (SIGMA, H0262)
HT Media Supplement (50×) Hybri-Max (SIGMA, H0137)
Equipment
6-well plate (BD, 353046)
Large flask for floating cell culture
Surgical tweezers (3)
Surgical scissors (3)
50 mL FALCON® tube
1 mL syringe
23G injection needle
Cell strainer 40 µm (BD, 352340)
Medium Composition

| Sp2/o culture medium | |
| --- | --- |
| DMEM | 500 mL |
| FBS | 55 mL (final 10%) |
| Penicillin-Streptomycin-Glutamine (100×) | 5 mL (final 1×) |
| Cell fusion medium | |
| DMEM | |
| Hybridoma medium | |
| DMEM | 500 mL |
| FBS | 55 mL (final 10%) |
| Penicillin-Streptomycin-Glutamine (100×) | 5 mL (final 1×) |
| 2ME | 500 µL (final 0.1%) |
| Insulin (10 mg/mL) | 250 µL (final 5 µg/mL) |
| rIL-6 | as appropriate (final 5 ng/mL) |
| HAT selection medium | |
| Hybridoma medium | |
| 50× HAT | as appropriate (final 1×) |

Procedures
Preparation of Myeloma (1 Week Before Cell Fusion)
1. Cryopreserved Sp2/0 cells (approximately $1 \times 10^6$ cells/vial) were thawed and suspended in 10 mL of Sp2/0 medium previously dispensed into a 15 mL FALCON® tube. The suspension was centrifuged at 1500 rpm for 3 minutes for washing and the supernatant was removed.

2. The pellet (Sp2/0 cells) was suspended in 4 ml of Sp2/0 medium.

3. A 6-well plate containing 4 mL of Sp2/0 medium in each well was prepared and the suspension of Sp2/0 cells prepared in step 2 above was diluted in 2-fold series.

4. The cells were cultured at 37° C. under 5.5% $CO_2$ for 1 to 2 days.

5. Cells in good condition according to microscopic observation were collected, and cultured and expanded in a large flask (or medium flask) for floating cell culture. The cells were passaged 2 days before cell fusion. (The cell density was adjusted to around $5 \times 10^5$ cells/mL on the day of cell fusion.)

Excision of Spleen from Mouse

1. The mouse was anesthetized, thoroughly sprayed with 70% ethanol, and then laparotomized in a safety cabinet. In order to aseptically remove the spleen, tweezers and scissors for exterior skin and those for intraperitoneal operation were sterilized.

2. After total blood sampling from the abdominal aorta under anesthesia, the spleen was removed.

3. The spleen was placed in a 50 mL FALCON® tube pre-filled with PBS and placed on ice until cell fusion.

Cell Fusion (Production of Hybridoma)

DMEM (serum-free) and PEG were preheated in a 37° C. incubator and the followings were performed.

1. Sp2/0 cells were collected and the number of the cells was counted. Only cells in flasks of $1 \times 10^6$ cells/mL or less were used.

2. About 10 mL of PBS was added to one well of a 6-well FALCON® plate, the excised spleen was placed therein, and the remaining adipose tissue was removed.

3. A fresh 10 mL of PBS was placed in one of the remaining wells and the spleen was transferred to the well. The spleen was cut in half with sterile tweezers and scissors.

4. A 23G needle was attached to a 1 mL syringe to aspirate PBS, and the PBS was injected into the spleen cut in half so that the splenocytes were extruded into the PBS. The extrusion was repeated until the spleen turned white.

5. A sterilized mesh was placed on top of a 50 mL FALCON® tube, and the PBS containing splenocytes was passed through the mesh so that tissues other than splenocytes were removed. The cell fusion medium was added so that the total volume was 40 mL.

6. The resulting mixture was centrifuged at 1500 rpm for 3 minutes and the supernatant was removed.

7. The spleen cells were suspended in 20 mL of cell fusion medium and stained with Turk's solution (Turk's solution: suspension=10:1), and leukocytes were counted. (Generally, it is about $1 \times 10^8$ cells, or $5 \times 10^6$ cells/mL.)

8. The resulting solution was centrifuged at 1500 rpm for 3 minutes and the supernatant was removed.

9. The cells were suspended in 3 mL of Red blood cell lysing buffer and left on ice for 3 minutes.

10. To the suspension, 17 mL of cell fusion medium was added, and the resulting solution was centrifuged at 1500 rpm for 3 minutes to collect splenocytes.

11. A medium containing Sp2/0 cells was added to the splenocytes in an amount that splenocytes: Sp2/0 cells was 5:1 in cell number to prepare a suspension.

12. The suspension was centrifuged at 1500 rpm for 3 minutes and its supernatant was removed.

13. The precipitated cells were resuspended by tapping.

14. One mL of PEG1500 was added over 1 minute with gentle stirring.

15. The stirring was continued for another 1 minute.

16. In the same manner as in step 14, 1 mL of cell fusion medium was added dropwise.

17. Further, 3 mL of cell fusion medium was added over 3 minutes.

18. Further, 10 mL of cell fusion medium was added over 1 minute.

19. The resulting mixture was left at 37° C. for 10 minutes.

20. The cell fusion medium was added so that the total volume was 40 mL.

21. The resulting mixture was centrifuged at 1500 rpm for 3 minutes and the supernatant was removed.

22. The precipitated cells were suspended in the hybridoma medium so that the number of splenocytes was $1 \times 10^6$ cells per mL, and the hybridoma was seeded on a 96-well flat bottom plate at 100 µL per well.

23. The hybridoma was cultured overnight at 37° C. under 5.5% $Co_2$.

24. 2×HAT selection medium was added at 100 µL/well, and the cell culture was continued.

25. The medium was exchanged by removing 100 µL of the supernatant every other day and adding 100 µL of 1×HAT selection medium.

3 Antibody Screening

Hybridomas producing anti-hGDF15 antibodies were selected as follows based on the binding strength to hGDF15 measured by ELISA using the supernatant of hybridomas 5 days after the start of culturing in a 96-well plate.

To a 96-well plate on which hGDF15 (R&D Systems, 957-GD-025/CF) was immobilized, 100 µL/well of the culture supernatant was added and reacted at room temperature for 2 hours. After washing of the wells, a secondary detection antibody (HRP-labeled anti-mouse IgG antibody (Promega, W402B)) was added and reacted at room temperature for 1 hour. After washing of the wells, TMB solution (Sigma, T2885) was added for color development, and the absorbance at 450 nm was measured with a plate reader.

Hybridomas in wells showing the absorbance at 450 nm of 1.0 or higher were further monoclonalized by limiting dilution. Finally, 16 clones were obtained. Of the 16 clones obtained, 13 clones were cultured, excluding one clone that was IgM and two clones that showed non-specific binding to multiple proteins.

Antibodies were purified from the culture supernatant using HITRAP™ rProtein A FF (GE Healthcare Life Sciences, 17508001). The concentration of the purified antibody was measured using NANODROP™ (Thermo Scientific) with an absorbance at 280 nm.

The binding affinity of each purified antibody with hGDF15 was measured by ELISA as follows. hGDF15 at a concentration of 200 ng/mL was added to the wells at 100 µL/well. A 96-well plate on which hGDF15 was immobilized was reacted with the purified antibody serially diluted at 0.39 ng/mL to 25 ng/mL at 100 µL/well, and then the hGDF15-anti-hGDF15 antibody complex was detected with an HRP-conjugated secondary antibody. For detecting color development, the absorbance at 450 nm was measured, and the value at the antibody amount of 5 ng/mL was calculated using a 4-parameter logistics curve. The binding value of each antibody was a relative value calculated by setting the value of clone MAB17 to 100.

Table 1 shows the results of affinity between hGDF15 and the obtained anti-hGDF15 antibody. MAB2, which showed a much stronger binding than MAB17, was humanized.

TABLE 1

| Clone | Relative value with the value of MAB17 as 100 |
|---|---|
| MAB3 | 72.3 |
| MAB4 | 44.2 |
| MAB5 | 36.4 |
| MAB6 | 68.1 |
| MAB1 | 33.6 |
| MAB11 | 12.0 |
| MAB12 | 36.2 |
| MAB13 | 50.1 |
| MAB7 | 3.1 |
| MAB15 | 25.1 |
| MAB14 | 26.4 |
| MAB17 | 100.0 |
| MAB2 | 350.9 |

4 Preparation of Humanized Antibody

Cells

Cell line name: ExpiCHO™

Origin: Chinese hamster

Cell source: Thermo Fisher Scientific (A29127)

Culture solution: ExpiCHO™ expression medium

Culture solution source: Thermo Fisher Scientific (A2910001)

Expression Vector

Vector name: pcDNA-3.1 cDNA origin: Total synthesis

Source: Thermo Fisher Scientific

Recombinant Protein

Protein name: Human GDF15

Origin: CHO cells

Source: R&D systems (957-GD-025/CF)

Design of Chimeric Antibody Sequence

The variable region containing the CDR sequences of MAB2, which is derived from a mouse, and the constant region of bevacizumab were joined to form a chimeric antibody sequence.

Design of Humanized Antibody Sequence

A human antibody with high similarity to MAB2 was searched by Blast search. The CDR sequences of the human antibody were replaced with those of MAB2 to prepare a variable region, and the variable region was joined with the constant region of bevacizumab to prepare a full-length humanized antibody. The amino acids of the mouse antibody that were considered to be important for maintaining its structure according to the structure prediction were maintained and used as a part of the humanized antibody.

Preparation and Purification of Antibody

The heavy and light chain genes were totally synthesized and incorporated into expression vectors, respectively. ExpiCHO™ cells were seeded on a 24-well plate, and the next day, the heavy and light chain expression vectors were co-transfected with TransIT®-CHO kit (Takara, V2170) to co-express the heavy and light chains. After 5 days, the whole culture supernatant containing the antibody produced was collected and the antibody was purified using HITRA™ rProteinA FF column (GE healthcare, 17-5080-01).

Measurement of Antibody Concentration

The antibody concentration in the supernatant was measured with Human IgG EIA kit (Takara, MK136) according to the protocol attached to the kit. The concentration of the purified antibody was determined by measuring the absorbance at 280 nm with NANODROP™ (Thermo Fisher Scientific)

Measurement of Amount of Binding to hGDF15 (ELISA)

A 100 μL human GDF15 solution (0.4 μg/mL) was added to a 96-well plate and left until the next morning to prepare a plate for ELISA. Blocking of the plate was performed with 1% BSA for 1 hour. A dilution series having a common ratio of 3 was prepared for the culture supernatant containing the antibody, and 100 μL each was added to the ELISA plate and left for 2 hours. For the reaction with a secondary antibody, 100 μL of a diluted solution of an HRP conjugated anti-human IgG antibody (Gene Tex, GTX26759) (20000-fold) was added and reacted for 1 hour. TMB (Sigma, T-0440) was used for color development reaction, and 2N sulfuric acid was used as a reaction terminator. The absorbance was measured at 450 nm.

Measurement of Binding Affinity Using BLITZ™

The binding affinity of the antibody was measured using BLITZ™ (Pall ForteBio), which is an biomolecular interaction analysis system. Anti-HIS (Pall ForteBio, 18-5114) was used as a sensor chip, and ForteBio Sample Diluent (Pall ForteBio, 18-1048) was used as a washing solution. The measurement program was set as 60 seconds for adsorption of hGDF15 to the sensor chip, 120 seconds for antibody binding, and 120 seconds for dissociation.

B. Sequencing

1 Test Methods

Total RNA was prepared from a hybridoma cultured in a 10 cm petri dish, and cDNA was synthesized using SMARTer® RACE 5'/3'Kit (Takara, 634858). The synthesized cDNA was incorporated into a pCR4Blunt-TOPO vector and amplified using *Escherichia coli*, and the plasmid DNA was purified. DNA sequencing was performed using BigDye™ Terminator v3.1 Cycle Sequencing Kit (Thermo Fisher Scientific, 43-37454) and M13 primer with ABI 3130xl Genetic Analyzer (Applied Biosystems).

2 Results

The amino acid sequences of MAB17, MAB2, and HuMAB2 are shown in Table 2, the CDR sequences of these antibodies are shown in Table 3, and the cDNA sequences of HuMAB2 are shown in Table 4. The CDRs were identified based on the Kabat's definition.

TABLE 2

| Antibody name | Sequence name (vector name) | Amino acid sequence (CDR sequence is underlined) | SEQ ID NO: |
|---|---|---|---|
| MAB2 | H chain variable region | MRMLSVLYLLSALPGILSDVQLQESGPSL VRPSQTLSLTCTVTGFSINSDCYWIWIRQ FPGNKLEYIGYTFYSGITYYNPSLASRTY ITRDTSKNQFSLKLNSVTTEDTATYYCAR DCDYAMDYWGQGTSVTVS | 4 |
| | L chain variable region | MGYSAQFLGLLLLCFQGTRCDIQMTQTTS SLSASLGDRVTISCRASQDISNYLNWYQQ FKDGTVKLLIHYTSTLHSGVPSRFSGSGS GTDYSLTISNLEQEDIATYFCQQGNTLPW TFGGGTKLEIKRADA | 5 |
| MAB17 | H chain variable region | MDRLTFSFLLLIVPAYVLSQVTLKESGPG ILQPSQTLSLTCSFSGFSLNTHGMGVGWI PQPSGKGLEWLANIWWNDDKYYNSALKSR LTLSKDTSNNQVFLKISSVDTADTATYFC AQVAWDWFAYWGQGTLVTIS | 6 |
| | L chain variable region | MDSQVQIFSFLLISASVILSRGQIVLTQS PAIMSASLGEEITLTCSASSSVRYMNWYQ QKSGTSPKVLIYSTSNLASGVPSRFSGSG | 7 |

53

TABLE 2-continued

| Antibody name | Sequence name (vector name) | Amino acid sequence (CDR sequence is underlined) | SEQ ID NO: |
|---|---|---|---|
| | | SGTFYSLTISSVEAEDAADYYCHQWSSYP WTFGGGTKLEIKRADA | |
| HuMAB2 | H chain variable region | MKHLWFLLLLAAPRWVLSQVQLQESGPGL VKPSETLSLTCTVSGFSINSDCYWIWIRQ PPGKGLEYIGYTFYSGITYYNPSLASRTT ISRDTSKNQFSLKLSSVTAADTAVYYCAR DCDYAMDYWGQGTLVTVSSASTKGPSVFP LAPSSKSTSG | 8 |
| | L chain variable region | MRVPAQLLGLLLLWLPGARCDIQMTQSPS SLSASVGDRVTITCRASQDISNYLNWYQQ KPGKAVKLLIGYTSTLHSGVPSRFSGSGS GTDYTLTISSLQPEDFATYFCQQGNTLPW TFGQGTKLEIKRTVAAPSVFIFPP | 9 |
| | H chain, full length (H3delK) | MKHLWFLLLLAAPRWVLSQVQLQESGPGL VKPSETLSLTCTVSGFSINSDCYWIWIRQ PPGKGLEYIGYTFYSGITYYNPSLASRTT ISRDTSKNQFSLKLSSVTAADTAVYYCAR DCDYAMDYWGQGTLVTVSSASTKGPSVFP LAPSSKSTSGGTAALGCLVKDYFPEPVTV SWNSGALTSGVHTFPAVLQSSGLYSLSSV VTVPSSSLGTQTYICNVNHKPSNTKVDKK VEPKSCDKTHTCPPCPAPELLGGPSVFLF PPKPKDTLMISRTPEVTCVVVDVSHEDPE VKFNWYVDGVEVHNAKTKPREEQYNSTYR VVSVLTVLHQDWLNGKEYKCKVSNKALPA PIEKTISKAKGQPREPQVYTLPPSREEMT KNQVSLTCLVK GFYPSDIAVEWESNGQP ENNYKTTPPVLDSDGSFFLYSKLTVDKSR WQQGNVFSCSVMHEALHNHYTQKSLSLSP G | 10 |

54

TABLE 2-continued

| Antibody name | Sequence name (vector name) | Amino acid sequence (CDR sequence is underlined) | SEQ ID NO: |
|---|---|---|---|
| L chain, full length (L7) | | MRVPAQLLGLLLLWLPGARCDIQMTQSPS SLSASVGDRVTITCRASQDISNYLNWYQQ KPGKAVKLLIHYTSTLHSGVPSRFSGSGS GTDYTLTISSLQPEDFATYVCQQGNTLPW TFGQGTKLEIKRTVAAPSVFIFPPSDEQL KSGTASVVCLLNNFYPREAKVQWKVDNAL QSGNSQESVTEQDSKDSTYSLSSTLTLSK ADYEKHKVYACEVTHQGLSSPVTKSFNRG EC | 11 |

TABLE 3

| Antibody name | Chain | CDR number | Sequence | SEQ ID NO: |
|---|---|---|---|---|
| MAB17 | H | CDR-H1 | THGMGVG | 12 |
| | H | CDR-H2 | NIWWNDDKYYNSALKS | 13 |
| | L | CDR-H3 | VAWDWFAY | 14 |
| | L | CDR-L1 | SASSSVRYMH | 15 |
| | L | CDR-L2 | STSNLAS | 16 |
| | L | CDR-L3 | HQWSSYPWT | 17 |
| MAB2 HuMAB2 | H | CDR-H1 | SDCYWI | 18 |
| | H | CDR-H2 | YTFYSGITYYNPSLAS | 19 |
| | H | CDR-H3 | DCDYAMDY | 20 |
| | L | CDR-L1 | RASQDISNYLN | 21 |
| | L | CDR-L2 | YTSTLHS | 22 |
| | L | CDR-L3 | QQGNTLPWT | 23 |

TABLE 4

| Antibody name | Sequence name (vector name) | cDNA sequence | SEQ ID NO: |
|---|---|---|---|
| HuMAB2 | H chain variable region | ATGAAGCACCTGTGGTTTCTGCTGCTGCTGGCCGC TCCCAGATGGGTGCTGTCTCAGGTGCAGCTGCAGG AATCTGGCCCTGGCCTCGTGAAGCCCAGCGAGACA CTGAGCCTGACCTGTACCGTGTCCGGCTTCAGCAT CAACAGCGACTGCTACTGGATCTGGATCAGACAGC CCCCTGGCAAGGGCCTGGAGTACATCGGCTACACC TTCTACAGCGGCATCACCTACTACAACCCCAGCCT GGCCAGCCGGACCACCATCAGCAGAGACACCAGCA AGAACCAGTTCAGCCTGAAGCTGAGCAGCGTGACA GCCGCCGATACCGCCGTGTACTACTGCGCCAGAGA CTGCGACTACGCCATGGACTATTGGGGCCAGGGCA CCCTCGTGACCGTGTCTAGCGCCTCTACAAAGGGC CCCAGCGTGTTCCCTCTGGCCCCTAGCAGCAAGAG CACATCTGGC | 24 |
| | L chain variable region | ATGAGAGTGCCTGCTCAGCTGCTGGGACTGCTGCT GCTGTGGCTGCCTGGCGCTAGATGCGACATCCAGA TGACCCAGAGCCCCAGCAGCCTGTCTGCCAGCGTG GGCGACAGAGTGACCATCACCTGTAGAGCCAGCCA GGACATCAGCAACTACCTGAACTGGTATCAGCAGA AACCCGGCAAGGCCGTGAAGCTGCTGATCCACTAC ACCAGCACCCTGCACAGCGGCGTGCCCAGCAGATT TTCTGGCAGCGGCTCCGGCACCGACTACACCCTGA CAATCAGCTCCCTGCAGCCCGAGGACTTCGCTACC TACTTCTGTCAGCAAGGCAACACCCTGCCCTGGAC CTTTGGCCAGGGCACCAAGCTGGAAATCAAGCGGA CAGTGGCCGCTCCCAGCGTGTTCATCTTCCCACCT | 25 |
| HuMAB2 | H chain, full length (H3delK) | ATGAAGCACCTGTGGTTTCTGCTGCTGCTGGCCGC TCCCAGATGGGTGCTGTCTCAGGTGCAGCTGCAGG AATCTGGCCCTGGCCTCGTGAAGCCCAGCGAGACA CTGAGCCTGACCTGTACCGTGTCCGGCTTCAGCAT CAACAGCGACTGCTACTGGATCTGGATCAGACAGC CCCCTGGCAAGGGCCTGGAGTACATCGGCTACACC TTCTACAGCGGCATCACCTACTACAACCCCAGCCT | 26 |

TABLE 4-continued

| Antibody name | Sequence name (vector name) | cDNA sequence | SEQ ID NO: |
|---|---|---|---|
| | | GGCCAGCCGGACCACCATCAGCAGAGACACCAGCA AGAACCAGTTCAGCCTGAAGCTGAGCAGCGTGACA GCCGCCGATACCGCCGTGTACTACTGCGCCAGAGA CTGCGACTACGCCATGGACTATTGGGGCCAGGGCA CCCTCGTGACCGTGTCTAGCGCCTCTACAAAGGGC CCCAGCGTGTTCCCTCTGGCCCCTAGCAGCAAGAG CACATCTGGCGGAACAGCCGCCCTGGGCTGCCTCG TGAAAGACTACTTCCCCGAGCCCGTGACAGTGTCC TGGAACTCTGGCGCCCTGACAAGCGGCGTGCACAC CTTTCCAGCCGTGCTGCAGAGCAGCGGCCTGTACT CTCTGTCCAGCGTCGTGACTGTGCCCAGCAGCTCT CTGGGCACCCAGACCTACATCTGCAACGTGAACCA CAAGCCCAGCAACACCAAGGTGGACAAGAAGGTGG AACCCAAGAGCTGCGACAAGACCCACACCTGTCCC CCTTGTCCTGCCCCCGAACTGCTGGGAGGCCCTTC CGTGTTCCTGTTCCCCCCAAAGCCCAAGGACACCC TGATGATCAGCAGAACCCCCGAAGTGACCTGCGTG GTGGTGGACGTGTCCCACGAGGACCCTGAAGTGAA GTTCAATTGGTACGTGGACGGCGTGGAAGTGCACA ACGCCAAGACCAAGCCTAGAGAGGAACAGTACAAC AGCACCTACCGGGTGGTGTCCGTGCTGACAGTGCT GCACCAGGACTGGCTGAACGGCAAGAGTACAAGT GCAAGGTGTCCAACAAGGCCCTGCCTGCCCCCATC GAGAAAACCATCTCCAAGGCCAAGGGACAGCCCCG CGAGCCCCAGGTGTACACACTGCCTCCAAGCCGGG AAGAGATGACCAAGAATCAGGTGTCCCTGACATGC CTCGTGAAGGGCTTCTACCCCTCCGATATTGCCGT GGAATGGGAGAGCAACGGCCAGCCCGAGAACAACT ACAAGACCACCCCCCCTGTGCTGGACAGCGACGGC TCATTCTTCCTGTACAGCAAGCTGACCGTGGACAA GTCCCGGTGGCAGCAGGGCAACGTGTTCAGCTGCA GCGTGATGCACGAGGCCCTGCACAACCACTACACC CAGAAGTCCCTGTCCCTGAGCCCCGGCTAA | |
| HuMAB2 | L chain, full length (L7) | ATGAGAGTGCCTGCTCAGCTGCTGGGACTGCTGCT GCTGTGGCTGCCTGGCGCTAGATGCGACATCCAGA TGACCCAGAGCCCCAGCAGCCTGTCTGCCAGCGTG GGCGACAGAGTGACCATCACCTGTAGAGCCAGCCA GGACATCAGCAACTACCTGAACTGGTATCAGCAGA AACCCGGCAAGGCCGTGAAGCTGCTGATCCACTAC ACCAGCACCCTGCACAGCGGCGTGCCCAGCAGATT TTCTGGCAGCGGCTCCGGCACCGACTACACCCTGA CAATCAGCTCCCTGCAGCCCGAGGACTTCGCTACC TACTTCTGTCAGCAAGGCAACACCCTGCCCTGGAC CTTTGGCCAGGGCACCAAGCTGGAAATCAAGCGGA CAGTGGCCGCTCCCAGCGTGTTCATCTTCCCACCT AGCGACGAGCAGCTGAAGTCTGGCACCGCCTCTGT CGTGTGCCTGCTGAACAACTTCTACCCCCGCGAGG CCAAGGTGCAGTGGAAGGTGGACAATGCCCTGCAG TCCGGCAACAGCCAGGAAAGCGTGACCGAGCAGGA CAGCAAGGACTCCACCTACAGCCTGTCCTCCACCC TGACCCTGAGCAAGGCCGACTACGAGAAGCACAAG GTGTACGCCTGCGAAGTGACCCACCAGGGCCTGAG CAGCCCTGTGACCAAGAGCTTCAACCGGGGCGAGT GCTGA | 27 |

C. Comparison with Existing Anti-hGDF15 Antibodies

1 Test Materials and Methods

Anti-hGDF15 Antibody

Table 5 shows the antibodies used for comparison of reactivity with HuMAB2.

TABLE 5

| Antibody name | Type |
|---|---|
| MAB17 | mouse, monoclonal |
| MAB3 | mouse, monoclonal |
| MAB4 | mouse, monoclonal |
| MAB5 | mouse, monoclonal |
| MAB6 | mouse, monoclonal |

TABLE 5-continued

| Antibody name | Type |
|---|---|
| MAB1 | mouse, monoclonal |
| MAB11 | mouse, monoclonal |
| MAB12 | mouse, monoclonal |
| MAB13 | mouse, monoclonal |
| Hu01G06-127[1] | humanized, monoclonal |
| MAB957[2] | mouse, monoclonal |
| Biotinylated Goat Anti-Human GDF-15 Detection Antibody[3] | goat, polyclonal |

[1] Humanized anti-hGDF15 antibody (WO2014/100689)
[2] R&D Systems, MAB957, Lot No: UDC1014011
[3] R&D Systems, DY957

Test Methods

HuMAB2 and the anti-GDF15 monoclonal antibodies shown in Table 5 (2 µg/mL) were added to 96-well plates at 100 µL/well to be immobilized on the plates, and reacted with 100 µL/well of hGDF15 (R&D Systems, 957-GD-025/CF) serially diluted from a concentration of 1 ng/ml. HuMAB2 biotinylated using EZ-Link™ Micro NHS-PEG4-Biotinylation Kit (Thermo Fisher Scientific, 21955) was used as the detection antibody (1 µg/mL as 100 µL/well). Whether or not sandwich ELISA was established was determined using Streptavidin-HRP conjugate in Human GDF15 ELISA Kit (R&D Systems, DY957). The detection antibody in Human GDF15 ELISA Kit (R&D Systems, DY957) (Table 5), which can establish sandwich ELISA with any monoclonal antibody, was used as a positive control antibody (PC) for sandwich ELISA.

2 Results

It was expected that competitive inhibition would occur when the immobilized antibody and the biotinylated antibody recognize similar epitopes, but no competitive inhibition would occur when these antibodies recognize different epitopes. As shown in FIG. 1, HuMAB2 was able to recognize hGDF15 at the same time as other antibodies. This result suggests that HuMAB2 recognizes an epitope different from epitopes of other antibodies.

As shown above, it was demonstrated that HuMAB2 does not compete with any existing antibody. Then, other antibodies obtained this time were tested to see whether each of these antibodies competes with HuMAB2 by the same method as described above. The results are shown in Table 6 as % inhibition. Of the 8 clones tested, 4 clones (MAB1, MAB11, MAB12 and MAB13) were found to inhibit the binding of HuMAB2 and hGDF15 by more than 70%.

TABLE 6

Results of competitive tests with individual hGDF15 monoclonal antibodies

| Clone | Inhibition % |
|---|---|
| MAB3 | 11 |
| MAB4 | 46 |
| MAB5 | 45 |
| MAB6 | 22 |
| MAB1 | 82 |
| MAB11 | 73 |
| MAB12 | 73 |
| MAB13 | 79 |
| MAB17 | 0 |
| HuMAB2 | 80 |

D. Crystallization of Complex of hGDF15 and HuMAB2 Fab

1 Test Materials and Methods hGDF15 (R&D Systems, 9279-GD-050) was mixed with HuMAB2 Fab (comprising a polypeptide consisting of the amino acid sequence of SEQ ID NO: 8 and a polypeptide consisting of the amino acid sequence of SEQ ID NO: 9) (20 ml Tris-HCl, 200 mM NaCl, pH7.2) at a molar ratio 1:1 to prepare a protein solution at a concentration of 5 mg/mL. HuMAB2 crystallization was performed by the Sitting drop vapor diffusion method. The mixing ratio of the protein solution and the reservoir solution was 1:1. Using the crystals obtained with the screening kit Crystal Screen 2 (Hampton Research, HR2-112), the crystal structure of the complex was determined with a resolution of 2.8i. The phase was determined by the molecular substitution method.

2 Results

Figure 2A:
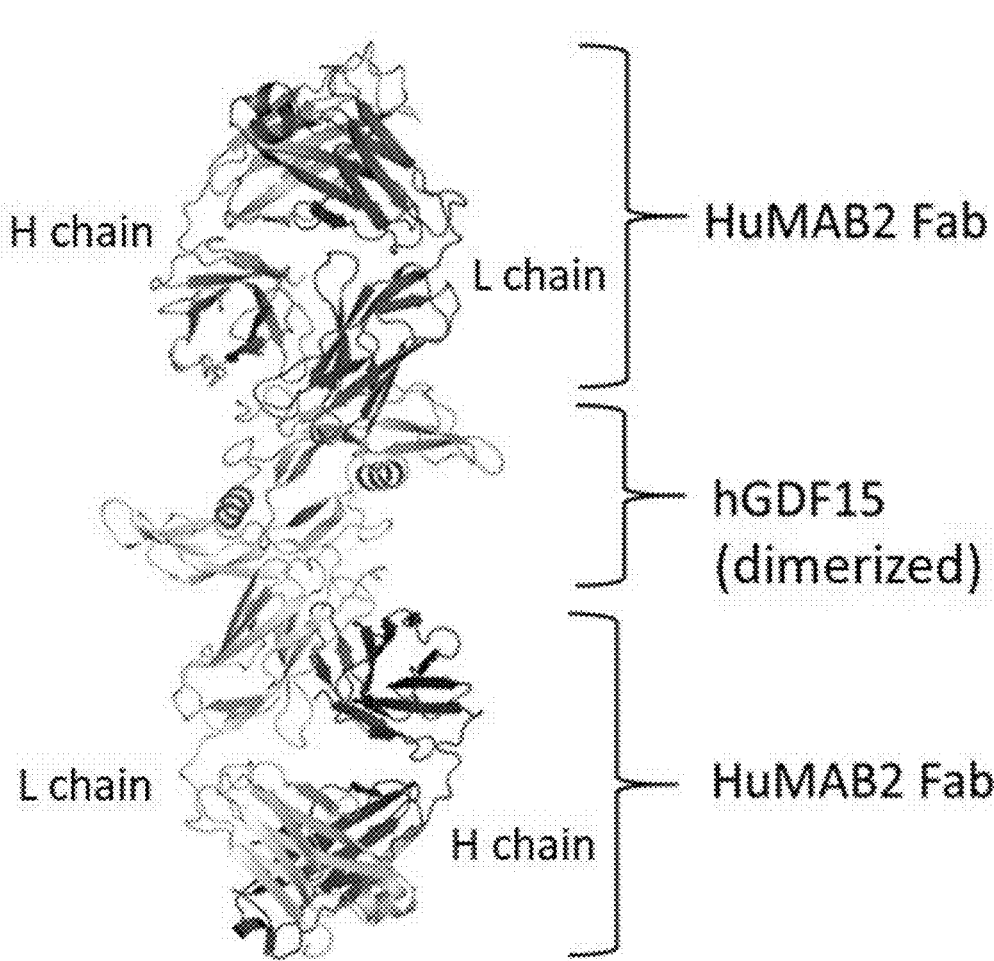
FIG. 2A shows the results of three-dimensional structure analysis of the cocrystal of HuMAB2 Fab and hGDF15.

Three-dimensional structural analysis revealed that hGDF15 formed a homodimer, and that two molecules of HuMAB2 Fab were bound to the hGDF15 dimer (FIG. 2A). The amino acids lined up at the binding interface between HuMAB2 and hGDF15 were identified as making up a paratope and an epitope, respectively (FIG. 2B). The identified epitope of hGDF15 and the amino acids on HuMAB2 that are important for binding are underlined in Table 7.

TABLE 7

| | Amino acid sequence | SEQ ID NO: |
|---|---|---|
| HuMAB2 H chain variable region | MKHLWFLLLLAAPRWVLSQVQLQESGPGLVKPS ETLSLTCTVSGFSINSDCYWIWIRQPPGKGLEY IGYTFYSGITYYNPSLASRTTISRDTSKNQFSL KLSSVTAADTAVYYCARDCDYAMDYWGQGTLVT VSSASTKGPSVFPLAPSSKSTSG | 8 |
| L chain variable region | MRVPAQLLGLLLLWLPGARCDIQMTQSPSSLSA SVGDRVTITCRASQDISNYLNWYQQKPGKAVKL LIHYTSTLHSGVPSRFSGSGSGTDYTLTISSLQ PEDFATYFCQQGNTLPWTFGQGTKLEIERTVAA PSVFIFPP | 9 |
| hGDF15 | ARNGDHCPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 10 |

Figure 3:
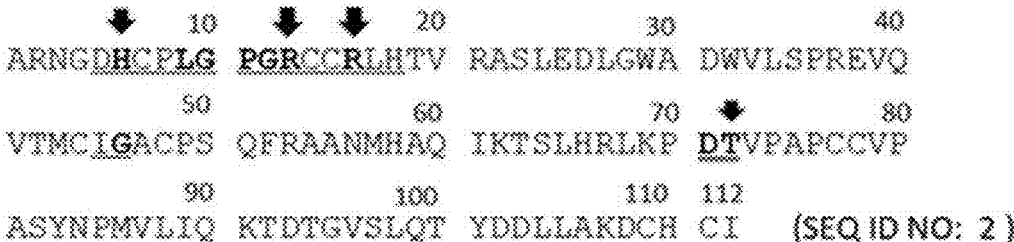
FIG. 3 shows the results of three-dimensional structure analysis of the binding between HuMAB2 Fab and hGDF15. hGDF15 forms a homodimer, and among the amino acids to which HuMAB2 binds, the amino acids present in one of the hGDF15 monomers (Monomer 1) are underlined, and the amino acids present in another monomer (Monomer 2) (71D72T) are double underlined. The amino acids that are important for binding are shown in bold, and the amino acids to which HuMAB2 particularly strongly binds are shown by arrows.

The epitope of hGDF15 analyzed using Molecular Operating Environment (MOE) is shown in FIG. 3. It was revealed that HuMAB2 binds to the 14 amino acids from aspartic acid at position 5 to histidine at position 18 at the N-terminus and isoleucine at position 45 (45I) and glycine at position 46 (46G) on one of the hGDF15 monomers (Monomer 1), and to aspartic acid at position 71 (71D) and threonine at position 72 (72T) on another monomer (Monomer 2).

Amino acid residues presumed to be particularly strongly involved in HuMAB2 interaction within the epitope were calculated using MOE Protein Contacts (Table 8). Then, the amino acids shown in FIG. 3 were shown to particularly strongly bind to HuMAB2.

TABLE 8

| Antibody | hGDF15 | E (kcal/mol) |
|---|---|---|
| L Asn112 | Arg13 | −6.5 |
| H Asp119 | Arg16 | −3.4 |
| H Phe71 | His6 | −1.6 |
| H Tyr69 | His6 | −1.4 |
| L Asn51 | Thr72 | −1.2 |
| L Tyr70 | Thr72 | −1.1 |
| H Ile75 | His6 | −1.1 |
| H Tyr120 | Leu17 | −0.91 |
| L Trp116 | Gly10 | −0.76 |
| H Tyr52 | Cys 7 | −0.72 |

* Top 10 are shown.

E. Reactivity of Anti-hGDF15 Antibody to hGDF15 and Mutant hGDF15

1 Test Materials and Methods

Test Materials

The antibodies used for comparison of reactivity with HuMAB2 antibody are shown in Table 9.

TABLE 9

| Antibody name | Type |
|---|---|
| MAB17 | mouse, monoclonal |
| Hu01G06-127[1] | humanized, monoclonal |
| MAB957[2] | mouse, monoclonal |
| Biotinylated Goat Anti-Human GDF-15 Detection Antibody[3] | goat, polyclonal |

[1] Humanized anti-hGDF15 antibody (WO2014/100689)
[2] R&D Systems, MAB957, Lot No: UDC1014011
[3] R&D Systems, DY957

Test Methods

Test Outline

An expression construct of a mutant hGDF15 was transfected into ExpiCHO-S™ cells. The transfected cells were cultured and the culture supernatant was collected. Once the expression of each mutant hGDF15 in the collected culture supernatant was confirmed with a commercially available ELISA kit for measuring GDF15, the reactivity of HuMAB2 to the mutant hGDF15 was evaluated by ELISA. Amino acid residues being particularly important in the epitope were identified by evaluating the reactivity of HuMAB2 to the mutated GDF15 by two methods, ELISA and a biomolecular interaction analysis system. Verification of differentiation by epitope differences between HuMAB2 and other anti-hGDF15 antibodies was performed by comparing the reactivity to a mutant hGDF15 of each of the other anti-hGDF15 antibodies with that of HuMAB2 by sandwich ELISA.

Preparation of Mutant hGDF15 pcDNA-3.1 vector (Thermo Fisher Scientific) into which each mutant hGDF15 gene was introduced was transfected using ExpiCHO™ Expression System Kit (Thermo Fisher Scientific, A29133) to ExpiCHO-S™ (Thermo Fisher Scientific) cells included in the kit. The culture supernatant 10 days after transfection was centrifuged at 8000 rpm for 30 minutes at 4° C., and the culture supernatant was collected. The collected culture supernatant was stored frozen (set temperature −20° C.).

Confirmation of Expression of Mutant hGDF15

The mutant hGDF15 in the collected culture supernatant was measured with Human GDF15 ELISA Kit (R&D System, DY957) according to the instructions of the kit to confirm expression and determine the concentration of the protein.

Evaluation of Reactivity of GDF15 Antibody to Mutant hGDF15

Recombinant Human GDF15 (R&D Systems, 957-GD-025/CF) was used as a wild-type (Wt) hGDF15. The Wt and mutant hGDF15 were serially diluted and reacted with a plate on which each hGDF15 antibody was immobilized and the bound Wt and mutant hGDF15 were detected with the detection antibody in Human GDF15 ELISA Kit (R&D Systems, DY957) (Table 9).

Evaluation of HuMAB2 Reactivity to Mutated GDF15 by Biomolecular Interaction Analysis System Each mutant hGDF15 was purified using an affinity column in which MAB17 was immobilized on Sepharose (GE Healthcare, 17-0906-01). The evaluation by the biomolecular interaction analysis system was performed using OCTET QKe (ForteBio). Recombinant Human GDF15 (R&D Systems, 957-GD-025/CF) was used as a Wt GDF15. The Wt and mutant hGDF15 were bound to the biosensor Ni-NTA (ForteBio, 18-5101) and then reacted with serially diluted HuMAB2 to evaluate the interaction between the mutant hGDF15 and HuMAB2. The analysis was performed using the Kinetics Method.

2 Results

The amino acid sequences of wild-type (WT) and mutant hGDF15 are shown in Table 10. The position where the amino acid of the wild-type hGDF15 was replaced with alanine is underlined.

TABLE 10

| | Sequence | SEQ ID NO: |
|---|---|---|
| hGDF15 (WT) | ARNGDHCPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 2 |
| H6A | ARNGDACPLG PGRCCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 28 |
| R13A | ARNGDHCPLG PGACCRLHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 29 |
| R16A | ARNGDHCPLG PGRCCALHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 30 |
| R13A, R16A | ARNGDHCPLG PGACCALHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 31 |
| 3A | ARNGDHCPLG PAACCALHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 32 |
| 4A | ARNGDHCPLG PAACCAAHTV RASLEDLGWA DWVLSPREVQ VTMCIGACPS QFRAANMHAQ IKTSLHRLKP DTVPAPCCVP ASYNPMVLIQ KTDTGVSLQT YDDLLAKDCH CI | 33 |

TABLE 10-continued

| | Sequence | | | SEQ ID NO: |
|---|---|---|---|---|
| 6A | ARNGDHCPLA AAACCAAHTV VTMCIGAC<u>PS</u> <u>QFRAANM</u>HAQ ASYNPMVLIQ KTDTGVSLQT | RASLEDLGWA IKTSLHRLKP YDDLLAKDCH | DWVLSPREVQ DTVPAPCCVP CI | 34 |
| 8A | ARNGDHC<u>AAA</u> AAACCAAHTV VTMCIGA<u>CPS</u> <u>QFRAANM</u>HAQ ASYNPMVLIQ KTDTGVSLQT | RASLEDLGWA IKTSLHRLKP YDDLLAKDCH | DWVLSPREVQ DTVPAPCCVP CI | 35 |
| T72A | ARNGDHCPLG PGRCCRLHTV VTMCIGACPS QFRAANMHAQ ASYNPMVLIQ KTDTGVSLQT | RASLEDLGWA IKTSLHRLKP YDDLLAKDCH | DWVLSPREVQ D<u>A</u>VPAPCCVP C<u>I</u> | 36 |

Table 11 shows the binding of the four anti-hGDF15 antibodies to hGDF15 and the mutant hGDF15. HuMAB2 did not bind to the mutant hGDF15, or bound but at a weaker level than to the wild-type hGDF15. In contrast, binding of other anti-hGDF15 antibodies to hGDF15 was not affected by the mutations. According to the results, it was revealed that, within the epitope of hGDF15 for HuMAB2, 5DHCPLGPGRCCRLH18 (SEQ ID NO: 3) on the N-terminus is important for the binding, and 13R and 16R are particularly important for binding of HuMAB2. The results also confirmed that MAB17, Hu01G06-127, and MAB957 have different epitopes from HuMAB2.

TABLE 11

| | Anti-GDF15 antibody | | | |
|---|---|---|---|---|
| | HuMAB2 | MAB17 | Hu01G06-127 | MAB957 |
| hGDF15 (WT) | 100 | 100 | 100 | 100 |
| H6A | 136.1 ± 1.4 | 87.7 ± 5.0 | 90.5 ± 2.3 | 88.3 ± 2.6 |
| R13A | 17.8 ± 1.4 | 97.2 ± 0.6 | 91.4 ± 3.5 | 89.9 ± 0.5 |
| R16A | 24.0 ± 0.9 | 101.2 ± 4.1 | 102.0 ± 4.3 | 93.9 ± 0.8 |
| R13A, R16A | 4.9 ± 0.9 | 83.0 ± 1.0 | 87.6 ± 3.0 | 80.6 ± 1.9 |
| 3A | 0.4 ± 0.2 | 109.8 ± 1.3 | 96.2 ± 0.2 | 99.0 ± 1.6 |
| 4A | 0.0 ± 0.1 | 95.0 ± 1.2 | 83.5 ± 1.3 | 84.1 ± 0.6 |
| 6A | 0.0 ± 0.0 | 83.9 ± 1.9 | 61.6 ± 0.5 | 74.3 ± 4.1 |
| 8A | −0.1 ± 0.1 | 78.8 ± 0.2 | 57.1 ± 0.6 | 69.2 ± 1.9 |
| T72A | 100.9 ± 2.7 | 104.4 ± 4.4 | 107.7 ± 6.9 | 101.2 ± 3.7 |

The binding to each mutant hGDF15 was expressed as a relative valve when the amount of the anti-GDF15 antibody bound to 500 pg/mL hGDF15 was 100. N=3. The value represents mean±SD.

F. Evaluation of HuMAB2 Antibody Reactivity to Epitope Region Peptide

1 Test Methods

Since the 14 residues from the asparagine residue at position 5 to the histidine residue at position 18 of hGDF15 (DHCPLGPGRCCRLH, SEQ ID NO: 3) were revealed to be important for the binding of HuMAB2, a peptide of this sequence was synthesized by GenScript™ (Table 12). Peptide 1 was unmodified at both ends, and Peptide 2 was synthesized by acetylating the amino terminus and amidating the carboxyl terminus for the purpose of mimicking the natural state because this region is an internal region within hGDF15. HuMAB2 antibody (10 µg/mL) was added at 100 µL/well to a 96-well plate on which a 10 µg/mL peptide solution had been added at 100 µL/well and the peptide had been immobilized, and thereby reacted with the peptide (25° C. for 3 hours). The bound HuMAB2 antibody was detected by adding a 5000-fold diluted anti-human IgG-HRP (Jackson ImmunoResearch, 109-035-008) at 100 µL/well and reacted at 25° C. for 1 hour. A plate on which hGDF15 (R&D Systems, 957-GD-025/CF) was immobilized was used as a control plate. The detection antibody in Human GDF15 ELISA Kit (R&D Systems, DY957) (Table 9) was used as a positive control antibody that reacts with the peptide, and Human IgG1 Isotype control (Abcam, ab206198) was used as a negative control antibody.

TABLE 12

| Synthesized peptides | | |
|---|---|---|
| Peptide name | Sequence | Modification |
| Peptide 1 | DHCPLGPGRCCRLH(SEQ ID NO: 3) | None |
| Peptide 2 | DHCPLGPGRCCRLH(SEQ ID NO: 3) | N-terminal acetylation and C-terminal amidation |

2 Results

Figure 4:
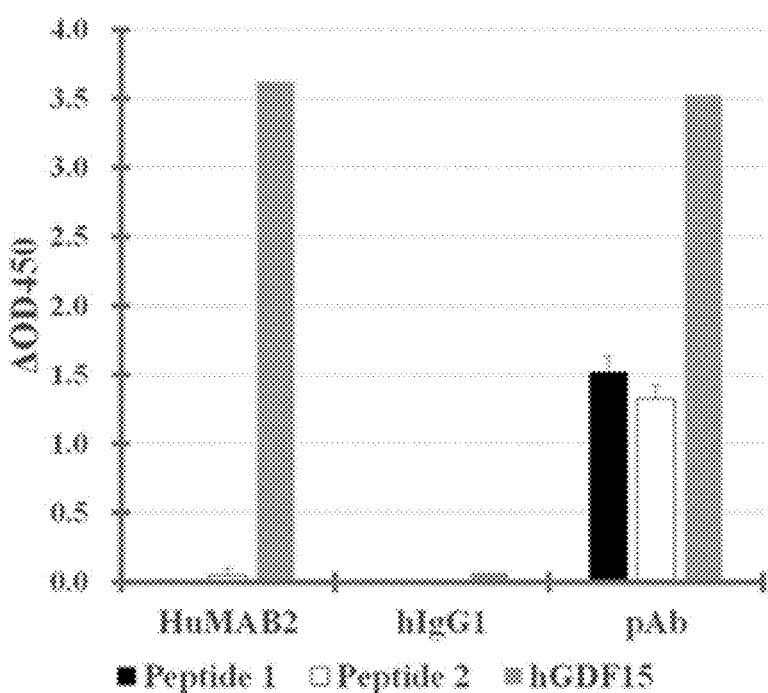
FIG. 4 shows the results of the binding assay between HuMAB2 and hGDF15 or a synthetic peptide of DHCPLGPGRCCRLH (SEQ ID NO: 3).
Figure 5A:
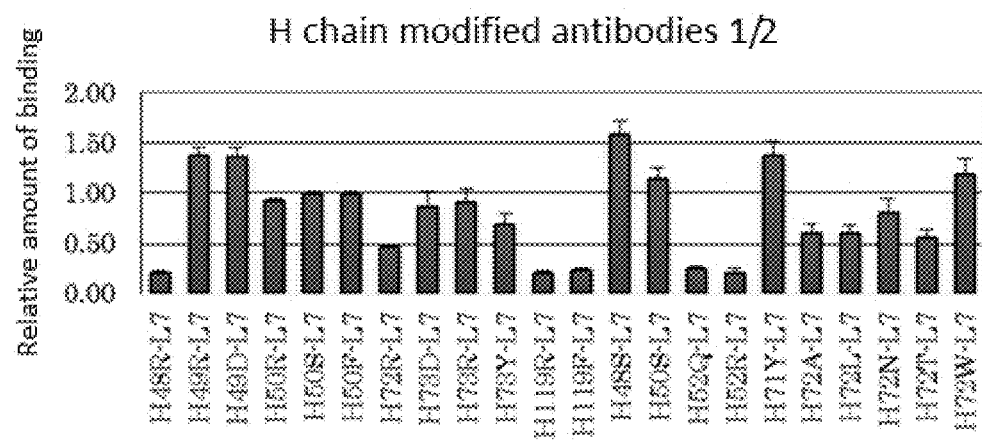
FIG. 5A shows the binding of HuMAB2 variants to hGDF15 (H chain modified antibodies 1/2).
Figure 5B:
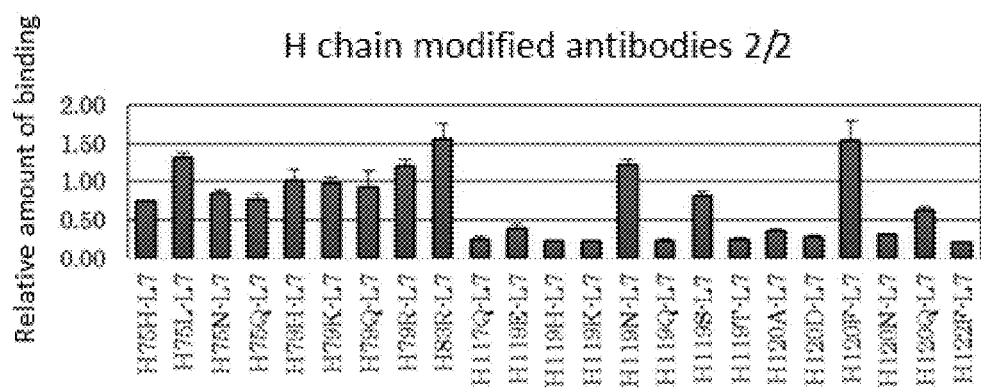
FIG. 5B shows the binding of HuMAB2 variants to hGDF15 (H chain modified antibodies 2/2).
Figure 5C:
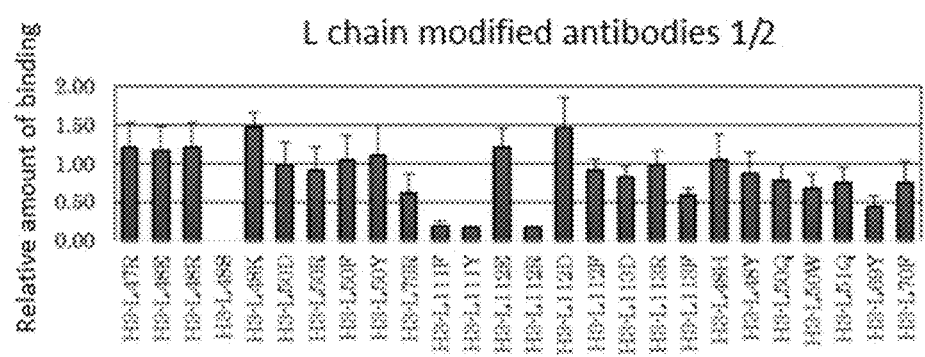
FIG. 5C shows the binding of HuMAB2 variants to hGDF15 (L chain modified antibodies 1/2).
Figure 5D:
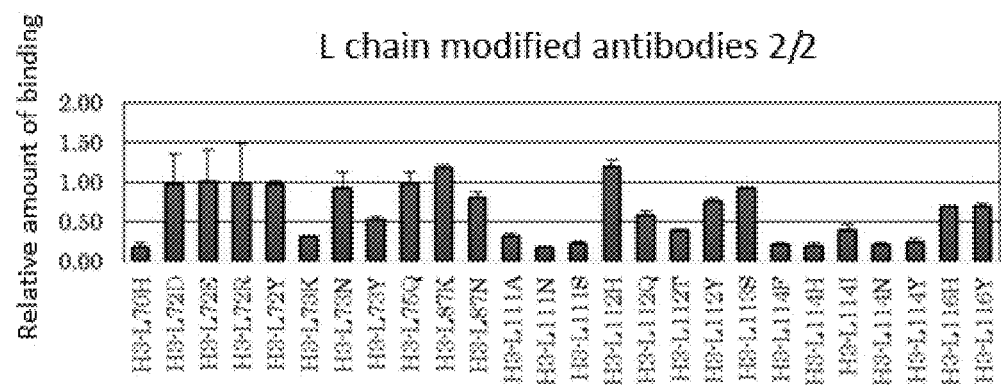
FIG. 5D shows the binding of HuMAB2 variants to hGDF15 (L chain modified antibodies 2/2).

As shown in FIG. 4, the anti-hGDF15 polyclonal antibody, which was a positive control antibody, reacted with both the two peptides and hGDF15. In contrast, HuMAB2 reacted only with hGDF15, and did not react with the two synthetic peptides as the negative control antibody Human IgG1 Isotype control (hIgG1). These results suggested that the sequence around the epitope or conformation is important for the binding of HuMAB2 to the epitope of hGDF15.

G. Binding to hGDF15 of HuMAB2 Variant Prepared by Amino Acid Substitution in CDR 1 Test Materials and Methods Test System Cells 1) Cell line name: ExpiCHO™

2) Origin: Chinese hamster

3) Cell source: Thermo Fisher Scientific (A29127)

4) Culture solution: ExpiCHO™ expression medium

5) Culture solution source: Thermo Fisher Scientific (A2910001)

Antibody Expression Vector

1) Vector name: pcDNA-3.1

2) cDNA origin: Total synthesis

3) Source: Thermo Fisher Scientific

Recombinant Protein

1) Protein name: Human GDF15 (hGDF15)

2) Origin: CHO cells

3) Source: R&D systems (957-GD-025/CF)

Test Methods

Design of Expression Vector

Based on the information obtained from the crystal structure analysis of HuMAB2 and hGDF15, the amino acids at the binding interface between the antibody and the antigen were determined as making up a paratope and an epitope, and expression vectors in which amino acid mutation was introduced into the heavy or light chain of HuMAB2 were designed. Table 13 shows a list of the variant antibodies (the modified amino acids are underlined). The regions in both heavy and light chains are arranged in the order of FR1-CDR1-FR2-CDR2-FR3-CDR3-FR4 from the N-terminus.

Cell Transfer of Expression Vector

CHO cells were seeded on a 24-well plate, and the next day, the expression vectors of the heavy and light chains of the variant antibody shown in Table 13 were introduced in combination into the cells using TransIT®-CHO kit (Takara, V2170). After 5 days, the whole supernatant was collected and stored in a freezer set at −20° C. until use.

Measurement of Amount of Binding to hGDF15

A 100 µL hGDF15 solution (0.4 µg/ml) was added to a 96-well plate and left at 4° C. until the next morning to prepare a plate for ELISA. To the plate, 1% BSA was added for blocking for 1 hour. A dilution series of the culture supernatant containing the variant antibody was prepared from 30-fold dilution (common ratio of dilution factor was 3), and 100 µL of each solution was added to the ELISA plate and left for 2 hours. As a secondary antibody, an HRP conjugated anti-human IgG antibody (Gene Tex, GTX26759) (20000-fold dilution) was added and left for 1 hour. TMB (Sigma, T-0440) was used for color development reaction, and 2N sulfuric acid was used as a reaction terminator. The absorbance was measured at 450 nm.

Measurement of Antibody Concentration Using OCTET

The antibody concentration in the culture supernatant was measured by a biomolecular interaction analysis system OCTET QKe (Pall ForteBio). The sensor chip was Protein L (Pall ForteBio, 18-5085), the regenerated solution for the sensor chip was 10 mM Glycine (pH1.1), and the washing solution was ForteBio Sample Diluent (Pall ForteBio, 18-1048). As a standard, IgG from human serum regent grade (Sigma-Aldrich, I12511-10MG) was used at 50 mg/mL, 10 mg/mL, 1 mg/mL, and 0.1 mg/mL, and the culture supernatant to be measured was diluted 2-fold with Sample Diluent (Pall ForteBio, 18-1104) before use. In the measurement program, the sensor chip was regenerated for 5 seconds and washed for 5 seconds for 3 cycles, and then the antibody concentration measurement was set as 120 seconds.

Comparison of Amount of Binding to HuMAB2

The amount of binding to human hGDF15 at 5 ng/mL of antibody was calculated on Excel, and the amount of binding of each variant antibody was expressed as a relative value when the amount of HuMAB2 bound to hGDF15 was 100. Three independent tests were performed to determine the mean±standard error. The amount of binding was set to 0 when the antibody was not expressed due to the mutation. The results are shown in FIGS. 5A to 5D.

2 Results

Five antibodies that showed a relative amount of binding of 1.5 times or more that of HuMAB2 were obtained. In contrast, a decrease of the amount of binding to 50% or less was observed in 30 antibodies. The two results of "H50S-L7" shown in of FIG. 5A "H chain modified antibody 1/2" were obtained with the same vector to check errors between wells in culture and ELISA. Since the two showed similar values, the test system was shown to be stable.

The heavy chain variant antibodies H48S-L7, H83R-L7, and H120F-L7, and the light chain variant antibodies H3-L48K and H3-L112D had an approximately 1.5-fold increase in binding strength compared to HuMAB2. On the other hand, since the amount of binding was decreased in the variant at glycine at position 111 (111G) and the variant at leucine at position 114 (114L), which were variants of the light chain of HuMAB2, these amino acids were suggested to make an important site for binding to hGDF15 and maintaining the structure of the CDR sequences of HuMAB2.

TABLE 13

| Antibody name | Sequence name chain | chain | Mutation site Chain | Region | Sequence | SEQ ID NO: |
|---|---|---|---|---|---|---|
| H48R-L7 | H48R | L7 | H | FR1 | DVQLQESGPGLVKPSETLS LTCTVSGFSIR | 37 |
| H49R-L7 | H49R | L7 | H | CDR-H1 | RDCYWI | 38 |
| H49D-L7 | H49D | L7 | H | CDR-H1 | DDCYWI | 39 |
| H50R-L7 | H50R | L7 | H | CDR-H1 | SRCYWI | 40 |
| H50S-L7 | H50S | L7 | H | CDR-H1 | SSCYWI | 41 |
| H50F-L7 | H50F | L7 | H | CDR-H1 | SFCYWI | 42 |
| H52R-L7 | H52R | L7 | H | CDR-H1 | SDCRWI | 43 |
| H52Q-L7 | H52Q | L7 | H | CDR-H1 | SDCQWI | 44 |
| H72R-L7 | H72R | L7 | H | CDR-H2 | YTFRSGITYYNPSLAS | 45 |
| H73D-L7 | H73D | L7 | H | CDR-H2 | YTFYDGITYYNPSLAS | 46 |
| H73R-L7 | H73R | L7 | H | CDR-H2 | YTFYRGITYYNPSLAS | 47 |
| H73Y-L7 | H73Y | L7 | H | CDR-H2 | YTFYYGITYYNPSLAS | 48 |

TABLE 13-continued

| Antibody name | Sequence name chain | chain | Chain | Region | Sequence | SEQ ID NO: |
|---|---|---|---|---|---|---|
| H119R-L7 | H119R | L7 | H | CDR-H3 | DCRYAMDY | 49 |
| H119F-L7 | H119F | L7 | H | CDR-H3 | DCFYAMDY | 50 |
| H48S-L7 | H48S | L7 | H | FR1 | DVQLQESGPGLVKPSETLS LTCTVSGFSIS | 51 |
| H71Y-L7 | H71Y | L7 | H | CDR-H2 | YTYYSGITYYNPSLAS | 52 |
| H72A-L7 | H72A | L7 | H | CDR-H2 | YTFASGITYYNPSLAS | 53 |
| H72L-L7 | H72L | L7 | H | CDR-H2 | YTFLSGITYYNPSLAS | 54 |
| H72N-L7 | H72N | L7 | H | CDR-H2 | YTFNSGITYYNPSLAS | 55 |
| H72T-L7 | H72T | L7 | H | CDR-H2 | YTFTSGITYYNPSLAS | 56 |
| H72W-L7 | H72W | L7 | H | CDR-H2 | YTFWSGITYYNPSLAS | 57 |
| H75H-L7 | H75H | L7 | H | CDR-H2 | YTFYSGHTYYNPSLAS | 58 |
| H75L-L7 | H75L | L7 | H | CDR-H2 | YTFYSGLTYYNPSLAS | 59 |
| H75N-L7 | H75N | L7 | H | CDR-H2 | YTFYSGNTYYNPSLAS | 60 |
| H75Q-L7 | H75Q | L7 | H | CDR-H2 | YTFYSGQTYYNPSLAS | 61 |
| H79H-L7 | H79H | L7 | H | CDR-H2 | YTFYSGITYYHPSLAS | 62 |
| H79K-L7 | H79K | L7 | H | CDR-H2 | YTFYSGITYYKPSLAS | 63 |
| H79Q-L7 | H79Q | L7 | H | CDR-H2 | YTFYSGITYYQPSLAS | 64 |
| H79R-L7 | H79R | L7 | H | CDR-H2 | YTFYSGITYYRPSLAS | 65 |
| H83R-L7 | H83R | L7 | H | CDR-H2 | YTFYSGITYYNPSLRS | 66 |
| H117Q-L7 | H117Q | L7 | H | CDR-H3 | QCDYAMDY | 67 |
| H119E-L7 | H119E | L7 | H | CDR-H3 | DCEYAMDY | 68 |
| H119H-L7 | H119H | L7 | H | CDR-H3 | DCHYAMDY | 69 |
| H119K-L7 | H119K | L7 | H | CDR-H3 | DCKYAMDY | 70 |
| H119N-L7 | H119N | L7 | H | CDR-H3 | DCNYAMDY | 71 |
| H119Q-L7 | H119Q | L7 | H | CDR-H3 | DCQYAMDY | 72 |
| H119S-L7 | H119S | L7 | H | CDR-H3 | DCSYAMDY | 73 |
| H119T-L7 | H119T | L7 | H | CDR-H3 | DCTYAMDY | 74 |
| H120A-L7 | H120A | L7 | H | CDR-H3 | DCDAAMDY | 75 |
| H120D-L7 | H120D | L7 | H | CDR-H3 | DCDDAMDY | 76 |
| H120F-L7 | H120F | L7 | H | CDR-H3 | DCDFAMDY | 77 |
| H120N-L7 | H120N | L7 | H | CDR-H3 | DCDNAMDY | 78 |
| H120Q-L7 | H120Q | L7 | H | CDR-H3 | DCDQAMDY | 79 |
| H122F-L7 | H122F | L7 | H | CDR-H3 | DCDYAFDY | 80 |
| H3-L47R | H3delK | L47R | L | CDR-L1 | RASRDISNYLN | 81 |
| H3-L48E | H3delK | L48E | L | CDR-L1 | RASQEISNYLN | 82 |
| H3-L48R | H3delK | L48R | L | CDR-L1 | RASQRISNYLN | 83 |
| H3-L48S | H3delK | L48S | L | CDR-L1 | RASQSISNYLN | 84 |
| H3-L48K | H3delK | L48K | L | CDR-L1 | RASQKISNYLN | 85 |

TABLE 13-continued

| Antibody name | Sequence name chain | Sequence name chain | Mutation site Chain | Mutation site Region | Sequence | SEQ ID NO: |
|---|---|---|---|---|---|---|
| H3-L50C | H3delK | L50C | L | CDR-L1 | RASQDIDNYLN | 86 |
| H3-L50R | H3delK | L50R | L | CDR-L1 | RASQDIRNYLN | 87 |
| H3-L50F | H3delK | L50F | L | CDR-L1 | RASQDIFNYLN | 88 |
| H3-L50Y | H3delK | L50Y | L | CDR-L1 | RASQDIYNYLN | 89 |
| H3-L73R | H3delK | L73R | L | CDR-L2 | YTSRLHS | 90 |
| H3-L111F | H3delK | L111F | L | CDR-L3 | QQFNTLPWT | 91 |
| H3-L111Y | H3delK | L111Y | L | CDR-L3 | QQYNTLPWT | 92 |
| H3-L112E | H3delK | L112E | L | CDR-L3 | QQGETLPWT | 93 |
| H3-L112R | H3delK | L112R | L | CDR-L3 | QQGRTLPWT | 94 |
| H3-L112D | H3delK | L112D | L | CDR-L3 | QQGDTLPWT | 95 |
| H3-L112F | H3delK | L112F | L | CDR-L3 | QQGFTLPWT | 96 |
| H3-L113D | H3delK | L113D | L | CDR-L3 | QQGNDLPWT | 97 |
| H3-L113R | H3delK | L113R | L | CDR-L3 | QQGNRLPWT | 98 |
| H3-L113F | H3delK | L113F | L | CDR-L3 | QQGNFLPWT | 99 |
| H3-L48H | H3delK | L48H | L | CDR-L1 | RASQHISNYLN | 100 |
| H3-L48Y | H3delK | L48Y | L | CDR-L1 | RASQYISNYLN | 101 |
| H3-L50Q | H3delK | L50Q | L | CDR-L1 | RASQDIQNYLN | 102 |
| H3-L50W | H3delK | L50W | L | CDR-L1 | RASQDIWNYLN | 103 |
| H3-L51Q | H3delK | L51Q | L | CDR-L1 | RASQDISQYLN | 104 |
| H3-L69Y | H3delK | L69Y | L | FR2 | WYQQKPGKAVKLLIY | 105 |
| H3-L70F | H3delK | L70F | L | CDR-L2 | FTSTLHS | 106 |
| H3-L70H | H3delK | L70H | L | CDR-L2 | HTSTLHS | 107 |
| H3-L72D | H3delK | L72D | L | CDR-L2 | YTDTLHS | 108 |
| H3-L72E | H3delK | L72E | L | CDR-L2 | YTETLHS | 109 |
| H3-L72R | H3delK | L72R | L | CDR-L2 | YTRTLHS | 110 |
| H3-L72Y | H3delK | L72Y | L | CDR-L2 | YTYTLHS | 111 |
| H3-L73K | H3delK | L73K | L | CDR-L2 | YTSKLHS | 112 |
| H3-L73N | H3delK | L73N | L | CDR-L2 | YTSNLHS | 113 |
| H3-L73Y | H3delK | L73Y | L | CDR-L2 | YTSYLHS | 114 |
| H3-L75Q | H3delK | L75Q | L | CDR-L2 | YTSTLQS | 115 |
| H3-L87K | H3delK | L87K | L | FR3 | GVPSRFSGSGKGTDYTLTI SSLQPEDFATYFC | 116 |
| H3-L87N | H3delK | L87N | L | FR3 | GVPSRFSGSGNGTDYTLTI SSLQPEDFATYFC | 117 |
| H3-L111A | H3delK | L111A | L | CDR-L3 | QQANTLPWT | 118 |
| H3-L111N | H3delK | L111N | L | CDR-L3 | QQNNTLPWT | 119 |
| H3-L111S | H3delK | L111S | L | CDR-L3 | QQSNTLPWT | 120 |
| H3-L112H | H3delK | L112H | L | CDR-L3 | QQGHTLPWT | 121 |
| H3-L112Q | H3delK | L112Q | L | CDR-L3 | QQGQTLPWT | 122 |

TABLE 13-continued

| Antibody name | Sequence name chain | chain | Chain | Mutation site Region | Sequence | SEQ ID NO: |
|---|---|---|---|---|---|---|
| H3-L112T | H3delK | L112T | L | CDR-L3 | QQGTTLPWT | 123 |
| H3-L112Y | H3delK | L112Y | L | CDR-L3 | QQGYTLPWT | 124 |
| H3-L113S | H3delK | L113S | L | CDR-L3 | QQGNSLPWT | 125 |
| H3-L114F | H3delK | L114F | L | CDR-L3 | QQGNTFPWT | 126 |
| H3-L114H | H3delK | L114H | L | CDR-L3 | QQGNTHPWT | 127 |
| H3-L114T | H3delK | L114T | L | CDR-L3 | QQGNTIPWT | 128 |
| H3-L114N | H3delK | L114N | L | CDR-L3 | QQGNTNPWT | 129 |
| H3-L114Y | H3delK | L114Y | L | CDR-L3 | QQGNTYPWT | 130 |
| H3-L116H | H3delK | L116H | L | CDR-L3 | QQGNTLPHT | 131 |
| H3-L116Y | H3delK | L116Y | L | CDR-L3 | QQGNTLPYT | 132 |

II. Pharmacological Test (1)

A. Capture of hGDF15 in Blood

1 Test Materials and Methods

Animals

1) Species/Lineage: mouse/BALB-c Slc-nu/nu
2) Microbiological grade: specific pathogen-free (SPF)
3) Source: Japan SLC
4) Gender: Female
5) Week age: 6 weeks old (at the time of hGDF15 or antibody administration)
6) Breeding conditions Animals are bred under the environment set at the following conditions.

a) Temperature: 23±2° C.
b) Humidity: 60±10%
c) Lighting: Lighting time: 7:00 am to 7:00 pm
   Off time: 7:00 pm to 7:00 am
d) Food and water: Free intake, CRF-1 (Oriental Yeast Co., Ltd.), tap water Test Schedule Table 14 shows the test schedule wherein the day of antibody administration is set as Day 0.

TABLE 14

| Item | Day with the day of antibody administration as Day 0 (● indicates the day of implementation) | | | | |
|---|---|---|---|---|---|
| | −2 | 0 | 1 | 2 | 3 |
| Grouping | ● | | | | |
| rhGDF15 administration | | ● | ● | ● | ● |
| Antibody administration | | ● | | | |
| Body weight, food intake | ● | ● | ● | ● | ● |
| Blood collection | | | | | ● |

How to Raise Animals

Mice were separated into individual cages 3 days after delivery. In order to acclimatize to individual breeding, the acclimatization period until grouping was set to 5 days.

Grouping

Based on the body weight, mice were divided into 6 groups in total, 6 animals per group, by an experimental data collection and processing system (SAS institute Japan, R9.3).

Administration of Anti-hGDF15 Antibody rhGDF15, HuMAB2 antibody, and MAB17 antibody were intraperitoneally administered at 10 mL/kg. To the control group, Dulbecco's Phosphate-Buffered Saline (DPBS) was administered at 10 mL/kg. The groups are shown in Table 15.

TABLE 15

| | Treatment | n |
|---|---|---|
| 1 | DPBS | 6 |
| 2 | rhGDF15 0.3 mg/kg | 6 |
| 3 | rhGDF15 1 mg/kg | 6 |
| 4 | rhGDF15 3 mg/kg | 6 |
| 5 | rhGDF15 3 mg/kg + MAB17 3 mg/kg | 6 |
| 6 | rhGDF15 3 mg/kg + HuMAB2 3 mg/kg | 6 |

Measurement of Body Weight and Food Intake

Body weight and food intake were measured on the day of grouping and 0, 1, 2, and 3 days after administration.

Blood Collection and Anatomy

Blood was collected from the inferior vena cava of mice anesthetized with isoflurane inhalation on 3 days after antibody administration. Plasma was prepared using an EDTA2K blood collection tube and stored in a freezer set at −80° C. until use. After blood collection, the mice were exsanguinated and euthanized by inferior vena cava incision under anesthesia.

Blood Unbound hGDF15 Concentration

In order to measure hGDF15 that was not bound to antibodies in blood (unbound hGDF15), antigen-antibody complexes were removed by the following procedure. Five μL of Protein A/G agarose beads (Thermo scientific, 20421) was mixed with 50 μL of mouse plasma and 145 μL of PBS and mixed at 4° C. for 2 hours. After centrifugation, the supernatant was transferred to a new EPPEN® tube and stored in a freezer at −80° C. until use. Subsequent blood GDF15 measurement was performed with a GDF15 measurement ELISA kit (R&D systems, DY957) according to the instructions of the kit. For samples below the detection limit, the blood GDF15 concentration was set to 0 μg/mL.

Statistical Analysis

Wilcoxon rank sum test was performed on the concentration of unbound GDF15 in blood. SAS software (SAS institute Japan, R9.3) was used for statistical analysis.

2 Results

Figure 6:
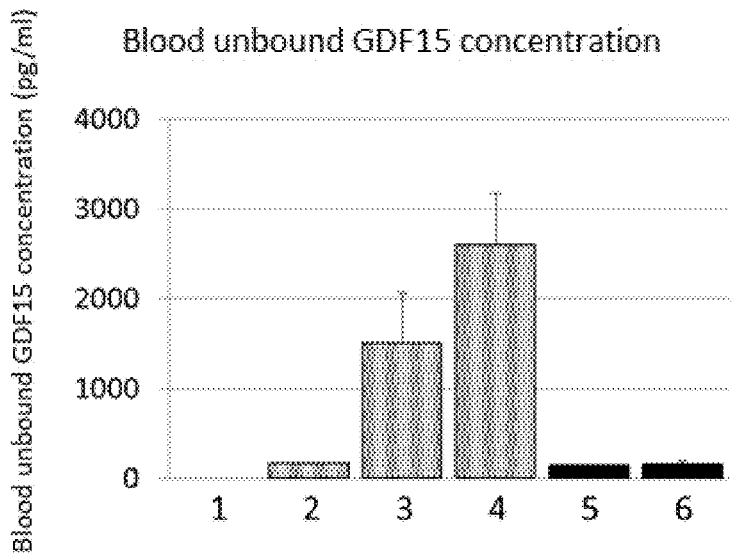
FIG. 6 shows the capture of hGDF15 in blood by HuMAB2 and MAB17.

The results are shown in FIG. 6. The blood hGDF15 concentration increased depending on the dose of rhGDF15, and both MAB17 and HuMAB2 captured GDF15 in blood.

B. Decreased Blood GDF15 Concentration in Cancer-Bearing Mouse Model

1 Test Materials and Methods

Test Substances

HuMAB2

MAB1

MAB13

Control Substances

MAB17

MAB957 (R&D Systems)

Hu01G06-127 (WO2014/100689)

Preparation of Test Substances and Control Substances

All antibodies were prepared at 1 mg/mL with DPBS and stored in a freezer at −80° C. until the day of administration.

Test System

Cells

1) Cell line name: MKN45

2) Origin: Human gastric cancer

3) Source: JCRB (Japanese Collection of Research Bioresources) cell bank

4) Culture conditions: 37° C., 5% $CO_2$ a) Culture medium: RPMI1640 i) Source: life technologies b) Serum: Fetal bovine serum i) Concentration: 10% ii) Source: Tissue Culture Biology

Animals

5) Species/Lineage: mouse/BALB-c Slc-nu/nu

6) Microbiological grade: specific pathogen-free (SPF)

7) Source: Japan SLC

8) Gender: Female

9) Week age: 7 weeks old (at the time of cell transplantation)

10) Animals were bred under the environment described in "A. Capture of hGDF15 in blood".

Group Composition

TABLE 16

| | | Test 1 | | |
|---|---|---|---|---|
| | Group | Cell transplantation | Agent administered (dose) | n |
| 1 | Normal(vehicle) | none | DPBS | 5 |
| 2 | MKN45(vehicle) | MKN45 | DPBS | 5 |
| 3 | MKN45(MAB17) | MKN45 | MAB17 (10 mg/kg) | 5 |
| 4 | MKN45(MAB957[1]) | MKN45 | MAB957 (10 mg/kg) | 5 |
| 5 | MKN45(Hu01G06-127[2]) | MKN45 | Hu01G06-127 (10 mg/kg) | 5 |
| 6 | MKN4S(HuMAB2) | MKN45 | HuMAB2 (10 mg/kg) | 5 |

[1]R&D Systems, MAB957, Lot No: UDC1014011
[2]Humanized anti-hGDF15 antibody (WO2014/100689)

TABLE 17

| | | Test 2 | | |
|---|---|---|---|---|
| | Group | Cell transplantation | Agent administered (dose) | n |
| 1 | Normal(vehicle) | none | DPBS | 5 |
| 2 | MKN45(vehicle) | MKN45 | DPBS | 5 |
| 3 | MKN45(MAB17) | MKN45 | MAB17 (10 mg/kg) | 5 |

TABLE 17-continued

| | | Test 2 | | |
|---|---|---|---|---|
| | Group | Cell transplantation | Agent administered (dose) | n |
| 4 | MKN45(MAB1) | MKN45 | MAB1 (10 mg/kg) | 5 |
| 5 | MKN45(MAB13) | MKH45 | MAB13 (10 mg/kg) | 5 |

Test Methods

How to Raise Animals

Mice were separated into individual cages 3 days after delivery. In order to acclimatize to individual breeding, the acclimatization period until transplantation of MKN45 was set to 5 days.

Cell Preparation and Cell Transplantation into Animals

MKN45 cells were cultured in a 150 mm petri dish. The cells were harvested by treatment with 0.25% trypsin-EDTA (SIGMA, T6689) on the day of transplantation, and the supernatant was removed by centrifugation (1200 rpm, 5 minutes). The cells were suspended in DPBS to $5 \times 10^6$ cells/mL and transplanted subcutaneously into the abdomen of mice anesthetized with isoflurane inhalation at 0.2 mL/body ($1 \times 10^6$ cells/body).

Grouping

In Test 1, 5 mice were randomly selected from 42 mice before transplantation of MKN45 as Normal (vehicle) group, and MKN45 was transplanted to the remaining 37 mice. Twelve days after transplantation of MKN45, the mice were divided into 6 groups, 5 mice per group, by SAS software (SAS institute Japan, R9.4) based on the body weight, and assigned to MKN45 (vehicle) group, MKN45 (MAB17) group, MKN45 (MAB957) group, MKN45 (Hu01G06-127) group, and MKN45 (HuMAB2) group. Similarly, in Test 2, the mice were assigned to Normal (vehicle) group, MKN45 (vehicle) group, MKN45 (MAB17) group, MKN45 (MAB1) group, and MKN45 (MAB13) group in 5 mice per group. After grouping, surplus animals were exsanguinated and euthanized under isoflurane anesthesia.

Administration of DPBS and Antibodies

DPBS and antibodies (10 mL/kg) were intraperitoneally administered 14 days after MKN45 transplantation (2 days after grouping). In Test 1, DPBS and antibodies were also administered 7 days after the start of antibody administration.

Blood Sampling

Blood was collected from the inferior vena cava of mice anesthetized with isoflurane inhalation 14 days (Test 1) or 7 days (Test 2) after the start of antibody administration. Plasma was prepared using an EDTA2K blood collection tube and stored in a freezer set at −80° C. until use. After blood collection, the mice were exsanguinated and euthanized by inferior vena cava incision under anesthesia.

Blood Unbound hGDF15 Concentration

In order to measure hGDF15 that was not bound to antibodies in blood (unbound hGDF15), the antigen-antibody complex was removed by the following procedure. Five μL of Protein A/G agarose beads (Thermo scientific, 20421), 50 μL of mouse plasma and 145 μL of PBS were mixed at 4° C. for 2 hours. After centrifugation, the supernatant was transferred to a new EPPEN® tube and stored in a freezer at −80° C. until use. Subsequent blood GDF15 measurement was performed with a GDF15 measurement ELISA kit (R&D systems, DY957) according to the instructions of the kit. For samples below the detection limit (62.5 pg/mL or less), the blood GDF15 concentration was set to 0 pg/mL.

Statistical Analysis

Wilcoxon rank sum test was performed on the concentration of unbound hGDF15 in blood 14 days (Test 1) or 7 days (Test 2) after the start of antibody administration. SAS software (SAS institute Japan, R9.4) was used for statistical analysis.

2 Results

In Test 1, the blood hGDF15 concentration was about 2000 pg/mL in the MKN45 group in which MKN45 cells were transplanted. Among the groups in which any of the antibodies was administered to the MKN45-transplanted model mouse, the blood hGDF15 concentration increased in the MAB17-, MAB957-, and Hu01G06-127-administered groups as compared with the solvent-administered group. On the other hand, in the HuMAB2-administered group, the blood hGDF15 concentration decreased (FIG. 7).

Table 18 shows the relative values when the blood hGDF15 concentration in the solvent-administered group was 100 in Test 2. Similar to HuMAB2, MAB1 and MAB13 also showed a decrease in blood hGDF15 concentration.

TABLE 18

| Group | Relative value of blood GDF15 level |
|---|---|
| MKN45(vehicle) | 100 |
| MKN45(MAB17) | 302.6 |
| MKN45(MAB1) | 72.1 |
| MKN45(MAB13) | 85.8 |

The above results were different from the results of MAB17 in the test administering a recombinant hGDF15 (FIG. 6). One of the reasons for this can be the difference in epitope between HuMAB2 and the other three antibodies used in the test. hGDF15 is produced by cleavage of pro hGDF15 by a proteolytic enzyme (A. R. Bauskin et al., Cancer Res. 2005; 65 (6): 2330-2336). It is considered that HuMAB2 has an epitope in the vicinity of this cleavage site, and binding to this epitope may suppress the production of hGDF15. It has been reported that an anti-CCL-2 neutralizing antibody (ABN912) did not improve but exacerbated the condition of rheumatoid arthritis patients. The antibody increased the blood CCL-2 concentration in a dose-dependent manner and this was considered to be one of the reasons of this exacerbation, suggesting the importance of reducing blood antigen levels (J. J. Haringman et al. Arthritis & Rheumatism 2006; 54 (8): 2387-2392). Therefore, anti-GDF15 antibodies that reduce the amount of blood GDF15 such as HuMAB2 are expected to be clinically more useful than those that increase blood hGDF15.

C. Improvement of Cachexia Symptoms in Cancer-Bearing Mouse Model (1)

1 Test Materials and Methods 1.1 Preparation of Test Substance

HuMAB2 was prepared at 1 mg/mL with DPBS and stored in a freezer at −80° C. until the day of administration.

1.2 Test system 1.2.1 Cells

1) Cell line name: MKN45

2) Origin: Human gastric cancer

3) Source: JCRB (Japanese Collection of Research Bioresources) cell bank

4) Culture conditions: 37° C., 5% $CO_2$ a) Culture medium: RPMI 1640 i) Source: life technologies b) Serum: Fetal bovine serum i) Concentration: 10% ii) Source: Tissue Culture Biology 1.2.2 Animal

1) Species/Lineage: mouse/BALB-c Slc-nu/nu

2) Microbiological grade: specific pathogen-free (SPF)

3) Source: Japan SLC

4) Gender: Female

5) Week age: 7 weeks old (at the time of cell transplantation)

6) Breeding conditions

Animals are bred under the environment set at the following conditions.

a) Temperature: 23±2° C.

b) Humidity: 60±10% c) Lighting: Lighting time: 7:00 am to 7:00 pm
Off time: 7:00 pm to 7:00 am d) Food and water: Free intake, CRF-1 (Oriental Yeast Co., Ltd.), tap water 1.2.3 Group Composition

TABLE 19

| Group | Cell transplantation | Agent administered (dose) | n |
|---|---|---|---|
| 1　Normal(vehicle) | none | DPBS | 8 |
| 2　MKN45(vehicle) | MKN45 | DPBS | 8 |
| 3　MKN45(HuMAB2) | MKN45 | HuMAB2 (10 mg/kg) | 8 |

1.3 Test Methods 1.3.1 Test Schedule

Table 20 shows the test schedule wherein the day of antibody administration was set as Day 0.

TABLE 20

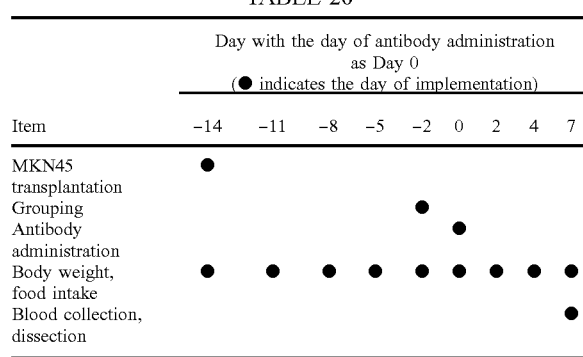

| Item | Day with the day of antibody administration as Day 0 (● indicates the day of implementation) | | | | | | | |
|---|---|---|---|---|---|---|---|---|
| | −14 | −11 | −8 | −5 | −2 | 0 | 2 | 4 | 7 |
| MKN45 transplantation | ● | | | | | | | | |
| Grouping | | | | ● | | | | | |
| Antibody administration | | | | | ● | | | | |
| Body weight, food intake | ● | ● | ● | ● | ● | ● | ● | ● | ● |
| Blood collection, dissection | | | | | | | | | ● |

1.3.2 how to Raise Animals

Mice were separated into individual cages 3 days after delivery. In order to acclimatize to individual breeding, the acclimatization period until transplantation of MKN45 was set to 5 days.

1.3.3 Cell Preparation and Cell Transplantation into Animals

MKN45 cells were cultured in a 150 mm petri dish. The cells were harvested by treatment with 0.25% trypsin-EDTA (SIGMA, T6689) on the day of transplantation, and the supernatant was removed by centrifugation (1200 rpm, 5 minutes). The cells were suspended in DBPS to $5×10^6$ cells/mL and transplanted subcutaneously into the abdomen of mice anesthetized with isoflurane inhalation at 0.2 mL/body ($1×10^6$ cells/body).

1.3.4 Grouping

Prior to transplantation of MKN45, 8 mice were randomly selected from 32 mice as Normal group, and MKN45 was transplanted to the remaining 24 mice. Twelve days after transplantation of MKN45, the mice were divided into 2 groups in total, 8 mice per group, based on the body weight, by an experimental data collection and processing system (EDCS, ver. 2.1) and assigned to MKN45 group and HuMAB2 group. After grouping, surplus animals were exsanguinated and euthanized under isoflurane anesthesia.

1.3.5 Administration of DPBS and HuMAB2

DPBS and HuMAB2 were administered 14 days after MKN45 transplantation (2 days after grouping). DPBS and HuMAB2 were administered intraperitoneally at 10 mL/kg.

1.3.6 Measurement of Body Weight and Food Intake

Body weight and food intake were measured every 3 days from the day of MKN45 transplantation to the day of antibody administration. Measurements were taken 0, 2, 4, and 7 days after antibody administration.

1.3.7 Blood Collection and Anatomy

Blood was collected from the inferior vena cava of mice anesthetized with isoflurane inhalation on 7 days after antibody administration. Plasma was prepared using an EDTA2K blood collection tube and stored in a freezer set at −80° C. until use. After blood collection, the mice were exsanguinated and euthanized by inferior vena cava incision under anesthesia. The tumor was collected by dissecting the skin of the tumor site with surgical scissors and the collected tumor was weighed.

1.4 Statistical Analysis

Regarding body weight and tumor weight 7 days after antibody administration and cumulative food intake from the day of antibody administration to Day 7, unpaired t-tests were performed between Normal group and MKN45 group and between MKN45 group and HuMAB2 group, respectively. Wilcoxon rank sum test was performed on the concentration of unbound GDF15 in blood. SAS software (SAS institute Japan, R9.3) was used for statistical analysis.

2 Results

Figure 8:
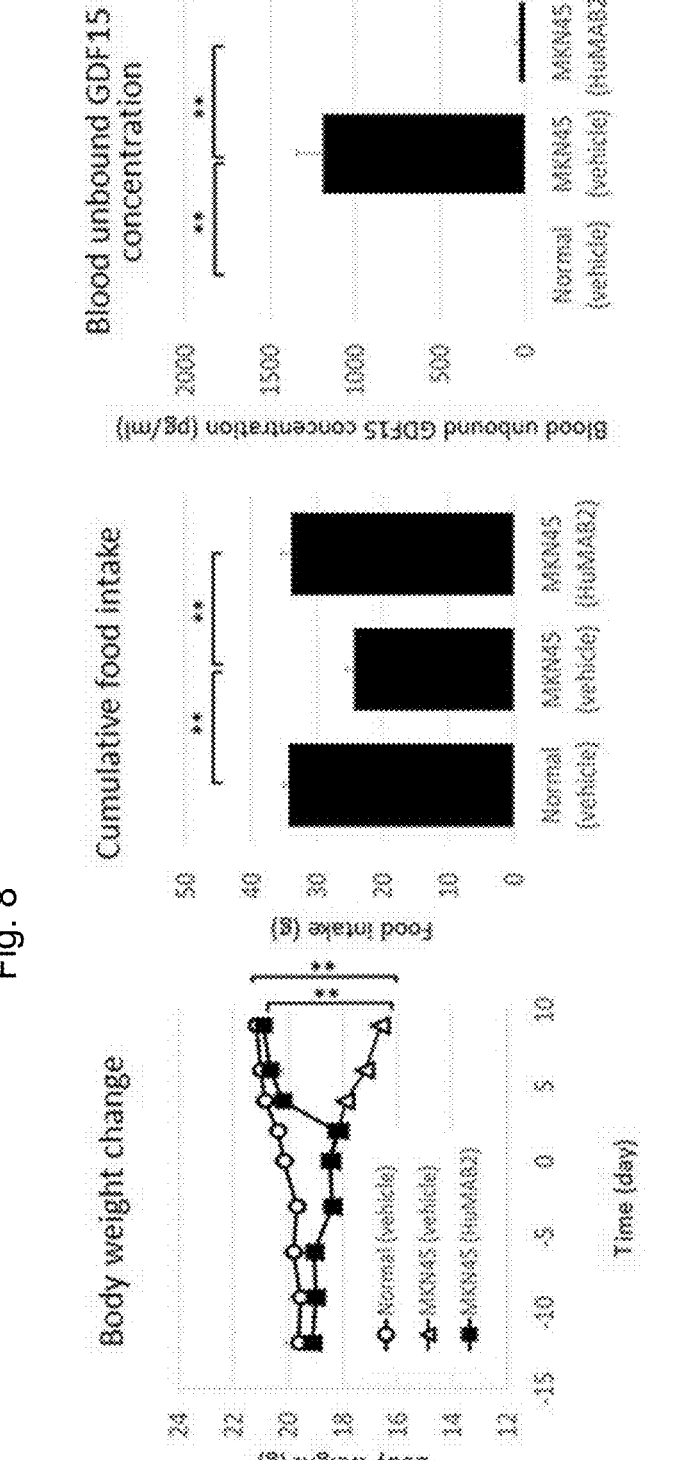
FIG. 8 shows the effect of HuMAB2 on weight loss, cumulative food intake, and blood unbound hGDF15 concentration in the cancer-bearing mouse model.

Using cancer-bearing (MKN45-transplanted) mice, the effect of HuMAB2 on changes in body weight and food intake, which are symptoms of cancer cachexia, was investigated, and the effect on the amount of unbound GDF15 in blood was also examined. FIG. 8 shows changes in body weight, cumulative food intake for 7 days after antibody administration, and blood unbound GDF15 concentration 7 days after antibody administration. The body weight 7 days after antibody administration was reduced by about 4 g in MKN45 group as compared with Normal group, and a significant weight loss was observed by transplantation of MKN45 cells (P<0.01). On the other hand, in HuMAB2 group, recovery of body weight loss was observed after administration of the antibody, and a significant increase in body weight was observed as compared with MKN45 group (P<0.01). Similarly, the cumulative food intake for 7 days after antibody administration was significantly decreased in MKN45 group (P<0.01), and significantly increased in HuMAB2 group compared with MKN45 group (P<0.01). No unbound GDF15 in blood was detected in Normal group, but the blood unbound GDF15 concentration significantly increased to about 1500 µg/mL in MKN45 group (P<0.01), and similar to the result in FIG. 7, it significantly decreased to about one twentieth in HuMAB2 group (P<0.01). These results confirmed that the cachexia-like symptoms (weight loss, food intake) in MKN45-transplanted mice were recovered by administration of HuMAB2.

D. Improvement of Cachexia Symptoms in Cancer-Bearing Mouse Model (2)

1 Test Materials and Methods 1.1 Preparation of Test Substance

HuMAB2 was prepared at 1 mg/mL with DPBS and stored in a freezer at −80° C. until the day of administration.

1.2 Test System 1.2.1 Cells

1) Cell line name: MKN45

1) Origin: Human (human gastric cancer tissue)

2) Source: JCRB (Japanese Collection of Research Bioresources)

3) Culture conditions: 37° C., 5% $CO_2$, Pre-culture conditions: 37° C., 5% $CO_2$ a) Culture medium: RPMI1640 i) Source: life technologies b) Serum: Fetal bovine serum i) Concentration: 10% ii) Source: Tissue Culture Biology 1.2.2 Animals

1) Species/Lineage: mouse/BALB-c Slc-nu/nu

2) Microbiological grade: specific pathogen-free (SPF)

3) Source: Japan SLC

4) Gender: Female

5) Week age: 6-12 weeks old

6) Breeding conditions

Animals were bred under the environment set at the following conditions.

a) Temperature: 23±2° C.

b) Humidity: 60±10% c) Lighting: Lighting time: 7:00 am to 7:00 pm

Off time: 7:00 pm to 7:00 am d) Food and water: Free intake (Pair-feeding group in Test 1 was fed with a prescribed amount daily), CRF-1 (Oriental Yeast Co., Ltd.), tap water 1.2.3 Group Composition

TABLE 21

| | Group | Cell transplantation | Agent administered (dose) | n |
|---|---|---|---|---|
| 1 | Normal(vehicle) | none | DPBS | 5 |
| 2 | MKN45(vehicle) | MKN45 | DPBS | 4 |
| 3 | MKN45(HuMAB2) | MKN45 | HuMAB2 (10 mg/kg) | 4 |

1.3 Test Methods 1.3.1 Model Preparation, Grouping, and Antibody Administration

Figure 9:
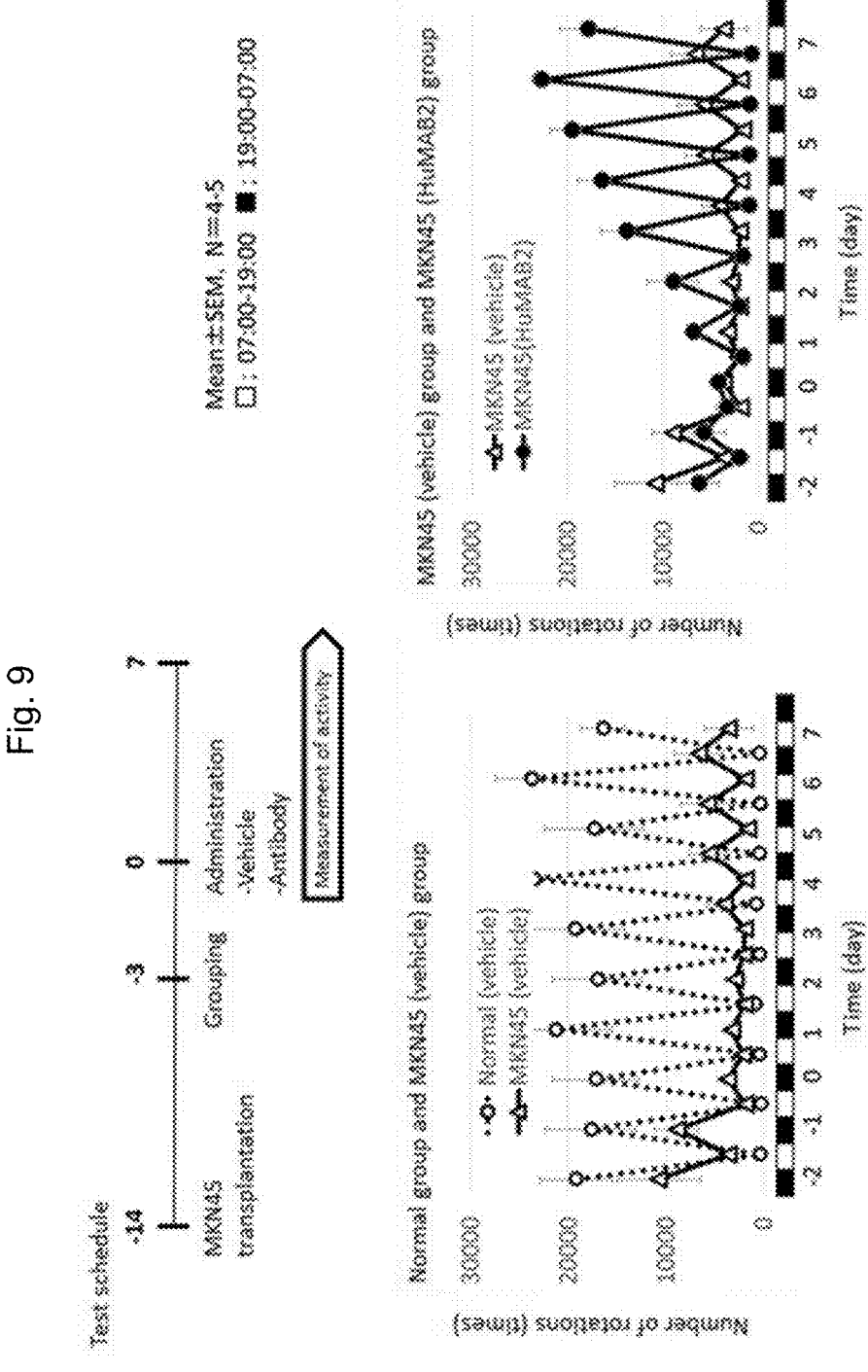
FIG. 9 shows the effect of HuMAB2 on the activity (circadian rhythm) of the cancer-bearing mouse model.

First, 5 animals were randomly selected as Normal group. The cachexia model was prepared as described in C above, and the antibody was intraperitoneally administered (FIG. 9).

1.3.2 Measurement of Locomotor Activity

To measure the locomotor activity, a wireless running wheel (Brain Science Idea, ENV-044) was installed in the cage, and the number of rotations of the running wheel was measured as the locomotor activity. The measured values were gathered every 12 hours in the light period (7 am to 7 pm) and the dark period (7 pm to 7 am).

1.4 Endpoint

Body weight

Locomotor activity 1.5 Statistical Analysis

Grouping was done in one dimension using weight as an index. SAS software (SAS institute Japan, R9.3) was used for grouping and testing.

2 Results

To assess cachexia-like symptoms induced by GDF15, a running wheel was placed in the cage and locomotor activity was measured. FIG. 9 shows the test schedule. Compared with Normal group, the amount of activity in MKN45 group decreased to about ¹/₁₀. It was demonstrated that this decrease in the amount of activity recovered to almost the same level as Normal group about 3 days after administration of HuMAB2. It was also demonstrated that in MKN45 group, not only the decrease in the amount of activity, but also a change in the activity pattern was observed. In Normal group, the characteristics of nocturnal animals, which become active in the dark period and less active in the light period, were observed. However, in MKN45 group, the activity pattern was clearly reversed. Then, in HuMAB2 group, to which the antibody was administered, the pattern was restored as in Normal group.

III. Antibody Production (2)

A. Sequencing

The amino acid sequences of MAB1 and MAB13 (Table 1) were determined in the same manner as those of MAB2. The amino acid sequences of the H and L chain variable regions are shown in Table 22, and the CDR sequences are shown in Table 23.

TABLE 22

| Antibody name | Sequence name (vector name) | Amino acid sequence (CDR sequence is underlined) | SEQ ID NO: |
|---|---|---|---|
| MAB1 | H chain variable | MSSPQSLKTLTITMGWTWIFTLILSVTTGVH SEVQLQQSGPELEKPGASVKISCKASGYSFT GYNMNWVKQSNGKSLEWIGNIDPYYGGTSYN QKFKGKATLTVDKSSSTAYMQLKSLTSEDSA VYYCARPGRYDGAWFAYWGQGTLVTVSA | 133 |
| | L chain variable region | MDFQVQIFSFLLISASVIMSRGQIVLSQSPA ILSASPGEKVTMTCRASSNVNYMHWYQQKPG SSPKPWIYATSNLASGVPARFSGSGSGTSYS LTISRVEAEDAATYYCQQWSDNPLTFGAGTK LELK | 134 |
| MAB13 | H chain variable region | MSSPQSLKTLTLTMGGIWIFLFLLSGTAGVH SEIQLQQTGPELVKPGASVKISCKASGYSFT DYIMLWVKQRHGKSLEWIGNIHPYYGTTSYN LKFKGKATLTVDKSSSTAYMQLNSLTSEDSA VYYCARGIGGSPFAYWGQGTLVTVSA | 135 |
| | L chain variable region | MKLPVRLLVLMFWIPASSSDVLMTQTPLSLP VSLGDQASISCRSSQSIVHSNGNTYLEWYLQ KPGQSPKLLIYKVSNRFSGVPDRFTGTGSGT DFTLKISRVEAEDLGVYYCFQGSHVPYTFGG GTKLEIK | 136 |

TABLE 23

| Antibody name | Chain | CDR number | Sequence | SEQ ID NO: |
|---|---|---|---|---|
| MAB1 | H | CDR-H1 | GYNMN | 137 |
| | H | CDR-H2 | NIDPYYGGTSYNQKFKG | 138 |
| | H | CDR-H3 | PGRYDGAWFAY | 139 |
| | L | CDR-L1 | RASSNVNYMH | 140 |
| | L | CDR-L2 | ATSNLAS | 141 |
| | L | CDR-L3 | QQWSDNPLT | 142 |
| MAB13 | H | CDR-H1 | DYIML | 143 |
| | H | CDR-H2 | NIHPYYGTTSYNLKFKG | 144 |
| | H | CDR-H3 | GIGGSPFAY | 145 |
| | L | CDR-L1 | RSSQSIVHSNGNTYLE | 146 |
| | L | CDR-L2 | KVSNRFS | 147 |
| | L | CDR-L3 | FQGSHVPYT | 148 |

B. Preparation of variant antibodies

In the same manner as in "I. Antibody production (1) G. Binding to hGDF15 of HuMAB2 variant prepared by amino acid substitution in CDR", HuMAB2 variants shown in Table 24 were further prepared. FIG. 10 shows the amount of binding to hGDF15 of each variant antibody when the amount of binding of HuMAB2 was 100. Antibodies showing a binding amount equal to or higher than that of HuMAB2 were obtained.

TABLE 24

| Antibody name | Sequence name | | Mutation site | | SEQ ID NO: |
|---|---|---|---|---|---|
| | H chain | L chain | Chain | Region | Sequence | |

| Antibody name | H chain | L chain | Chain | Region | Sequence | SEQ ID NO: |
|---|---|---|---|---|---|---|
| H54T-L7 | H54T | L7 | H | CDR-H1 | SDCYWT | 149 |
| H54N-L7 | H54N | L7 | H | CDR-H1 | SDCYWN | 150 |
| H71R-L7 | H71R | L7 | H | CDR-H2 | YTRYSGITYYNPSLAS | 151 |
| H71H-L7 | H71H | L7 | H | CDR-H2 | YTHYSGITYYNPSLAS | 152 |
| H77I-L7 | H77I | L7 | H | CDR-H2 | YTIYSGITYYNPSLAS | 153 |
| H3-L51Y | H3 | L51Y | L | CDR-L1 | RASQDISYYLN | 154 |
| H3-L72F | H3 | L72F | L | CDR-L2 | YTFTLHS | 155 |
| H3-L73Q | H3 | L73Q | L | CDR-L2 | YTSQLHS | 156 |
| H3-L74H | H3 | L74H | L | CDR-L2 | YTSTHHS | 157 |

Figure 11:
FIG. 11 shows the binding of HuMAB2 variants to hGDF15, wherein the HuMAB2 variants are composed of a variant H chain (H49R, H49D, H48S, H71Y, H83R, or H120F) and a variant L chain (L48K, L112D, L72F, or L74H).

Further, the H chain (H49R, H49D, H48S, H71Y, H83R, or H120F) and L chain (L48K, L112D, L72F, or L74H) (Table 25), which were from the HuMAB2 variants having high binding activity to hGDF15, were combined and the binding of the antibody thus obtained to hGDF15 was examined. The results are shown in FIG. 11. A large number of antibodies showing a binding amount equal to or higher than that of HuMAB2 were obtained.

TABLE 25

| Sequence name | Mutation site | | | SEQ ID NO: |
|---|---|---|---|---|
| | Chain | Region | Sequence | |
| H49R | H | CDR-H1 | RDCYWI | 38 |
| H49D | H | CDR-H1 | DDCYWI | 39 |
| H48S | H | FR1 | DVQLQESGPGLVKPSETL SLTCTVSGFSIS | 51 |
| H71Y | H | CDR-H2 | YTYYSGITYYNPSLAS | 52 |
| H83R | H | CDR-H2 | YTFYSGITYYNPSLRS | 66 |
| H120F | H | CDR-H3 | DCDFAMDY | 77 |
| L48K | L | CDR-L1 | RASQKISNYLN | 85 |
| L112D | L | CDR-L3 | QQGDTLPWT | 95 |
| L72F | L | CDR-L2 | YTFTLHS | 155 |
| L74H | L | CDR-L2 | YTSTHHS | 157 |

C. Evaluation of Inhibitory Activity Against GDF15, GFRAL and RET Complex Formation GDF15 forms a complex with the receptor GFRAL and the co-receptor RET to transduce intracellular signals. Then, the effects of HuMAB2 on GDF15, GFRAL and RET complex formation were examined.

Figure 12:
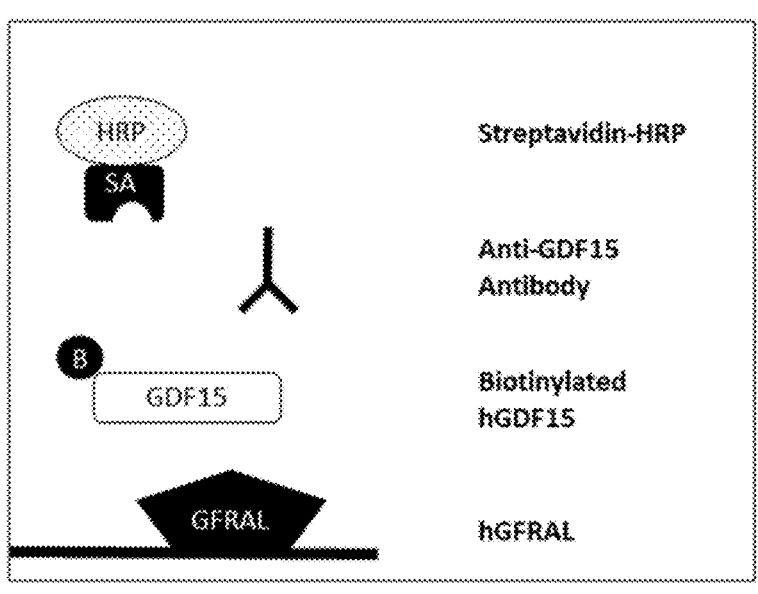
FIG. 12 shows a schema of evaluation of inhibitory activity of an anti-hGDF15 antibody against GDF15 and GFRAL complex formation.

First, the effect on GDF15 and GFRAL complex formation was examined (FIG. 12). GFRAL (R&D systems, 9697-GR) was immobilized on a plate, and GDF15 (R&D systems, 957-GD/CF) biotinylated with EZ-Link™ Micro NHS-PEG4-Biotinylation Kit (Thermo Fisher Scientific, 21955) and a serially diluted solution of an anti-GDF15 monoclonal antibody (Table 26) were reacted with the plate. Human IgG1, kappa-Isotype Control (Abcam) was used as a negative control antibody. GDF15 bound to GFRAL was detected using Pierce High Sensitivity Streptavidin-HRP (Thermo Fisher Scientific, 21130). TMB 1-Component Microwell Peroxidase Substrate, SureBlue™ (SeraCare Life Sciences) was used for color development, and the reaction was stopped by adding a stop solution (Wako). Absorbance was measured at 450 nm (OD450) using Emax (Molecular Devices). The % of control value was calculated according to Equation-1 from the OD450 value when each antibody was added, with the OD450 value when no antibody was added as a control. The IC50 value was obtained by calculating the inhibition rate from the % of control value thus obtained according to Equation-2 and using an Excel macro for IC50 calculation.

% of control=OD450 value of antibody-added sample/OD450 value without antibody addition×100 (Equation-1)

Inhibition rate=100−% of control (Equation-2)

As shown in Table 26, anti-GDF15 antibodies other than HuMAB2 inhibited the complex formation of GDF15 and GFRAL, while HuMAB2 did not. This difference was thought to be due to difference of the epitopes of these antibodies.

TABLE 26

| Antibody | IC50 (nM) |
|---|---|
| HuMAB2 | >500 |
| Hu01G06-127[1] | 0.05 |
| MAB17 | 11.98 |
| MAB957[2] | 11.13 |
| Human IgG[3] (Negative Control) | >500 |

[1]Humanized anti-hGDF15 antibody (WO2014/100689)
[2]R&D Systems, MAB957, Lot No: UDC1014011
[3]Human IgG1, kappa-Isotype Control (Abcam)

Next, the effects on GDF15, GFRAL and RET complex formation were examined. To an ELISA plate on which 30 nM GFRAL (R&D systems) was immobilized, a mixture of 50 nM GDF15 (R&D Systems, 9279-GD), 30 nM RET (R&D Systems, 1168-CR), and a serially diluted solution of HuMAB2 (0-500 nM) was added. Human IgG1, kappa-Isotype Control (Abcam) was used as a negative control antibody. The GDF15/GFRAL/RET complex thus formed was detected using Anti-His Peroxidase conjugated antibody (R&D systems, MAB050H). TMB 1-Component Microwell Peroxidase Substrate, SureBlue™ (SeraCare Life Sciences) was used for color development, and the reaction was stopped by adding a stop solution (Wako). Absorbance was measured at 450 nm using Emax (Molecular Devices). The % of control value was calculated according to Equation-1 from the OD450 value when each antibody was added, with the OD450 value when no antibody (0 nM antibody) was added as a control. The IC50 value was obtained by calculating the inhibition rate from the % of control value thus obtained according to Equation-2 and using an Excel macro for IC50 calculation.

HuMAB2 failed to show inhibitory activity against GDF15/GFRAL complex formation (Table 26), but showed against GDF15/GFRAL/RET complex formation (FIG. 13). From these result, HuMAB2 was considered to exert its inhibitory activity on the function of GDF15 by inhibiting complex formation with RET, which functions to transmit signals into cells.

VI. Pharmacological Test (2)

A. Improvement of Cachexia Symptoms in Cancer-Bearing Mouse Model (3)

In the same manner as in "II. Pharmacological test (1) C. Improvement of cachexia symptoms in cancer-bearing mouse model (1)", the effect of MAB1 on body weight, food intake, and the amount of unbound GDF15 in blood was examined with cancer-bearing (MKN45 cell-transplanted) mice. The groups are shown in Table 27.

TABLE 27

| Group | Cell transplantation | Agent administered (dose) | n |
|---|---|---|---|
| 1 Normal(vehicle) | none | DPBS | 8 |
| 2 MKN45(vehicle) | MKN45 | DPBS | 8 |
| 3 MKN45(MAB17) | MKN45 | MAB17 (10 mg/kg) | 8 |
| 4 MKN45(MAB1) | MKN45 | MAB1 (10 mg/kg) | 8 |

FIG. 14 shows changes in body weight, cumulative food intake for 7 days after antibody administration, and blood unbound GDF15 concentration 7 days after antibody administration. Weight loss was observed in MKN45 group, whereas recovery of weight loss was observed in MAB1 group after administration of the antibody. The cumulative food intake for 7 days after antibody administration also tended to increase in MAB1 group compared with MKN45 group. The blood unbound GDF15 concentration increased by MKN45 transplantation was decreased by MAB1, as was by HuMAB2 (FIG. 8). These results confirmed that the cachexia-like symptoms (weight loss, food intake) of MKN45 transplanted mice are recovered by administration of MAB1.

The invention claimed is:

1. An anti-hGDF15 antibody selected from:

(1) an anti-hGDF15 antibody comprising:

a heavy chain variable region that contains

CDR1 comprising an amino acid sequence selected from the group consisting of the amino acid sequences of SEQ ID NOs: 18, 38-44, and 149-150, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(2) an anti-hGDF15 antibody comprising:

a heavy chain variable region that contains

CDR1 comprising the amino acid sequence of SEQ ID NO: 18,

CDR2 comprising an amino acid sequence selected from the group consisting of the amino acid sequences of SEQ ID NOs: 19, 45-48, 52-66, and 151-153, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(3) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising an amino acid sequence selected from the group consisting of the amino acid sequences of SEQ ID NOs: 20, 49, 50 and 67-80; and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 23;

(4) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising an amino acid sequence selected from the group consisting of the amino acid sequences of SEQ ID NOs: 21, 81-83, 85-89, 100-104, and 154, CDR2 comprising the amino acid sequence of SEQ ID NO: 22, and CDR3 comprising the amino acid sequence of SEQ ID NO: 23;

(5) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising the amino acid sequence of SEQ ID NO: 21, CDR2 comprising an amino acid sequence selected from the group consisting of the amino acid sequences of SEQ ID NOs: 22, 90, 106-115, and 155-157, and CDR3 comprising the amino acid sequence of SEQ ID NO: 23;

(6) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising an amino acid sequence selected from the group consisting of the amino acid sequences of SEQ ID NOs: SEQ ID NO: 23, 91-99, and 118-132;

(7) an anti-hGDF15 antibody comprising:

a heavy chain variable region that contains

CDR1 comprising an amino acid sequence selected from the group consisting of the amino acid sequences of SEQ ID NOs: 38 and 39, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 85, CDR2 comprising the amino acid sequence of SEQ ID NO: 22, and CDR3 comprising the amino acid sequence of SEQ ID NO: 23;

(8) an anti-hGDF15 antibody comprising:

a heavy chain variable region that contains

CDR1 comprising the amino acid sequence of SEQ ID NOs: 18,

CDR2 comprising an amino acid sequence selected from the group consisting of the amino acid sequences of SEQ ID NOs: 52 and 66, and CDR3 comprising the amino acid sequence of SEQ ID NO: 20; and a light chain variable region that contains CDR1 comprising the amino acid sequence of SEQ ID NO: 85, CDR2 comprising the amino acid sequence of SEQ ID NO: 22, and CDR3 comprising the amino acid sequence of SEQ ID NO: 23;

(9) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 77; and a light chain variable region that contains CDR1 comprising the amino acid sequence of SEQ ID NO: 85, CDR2 comprising the amino acid sequence of SEQ ID NO: 22, and CDR3 comprising the amino acid sequence of SEQ ID NO: 23;

(10) an anti-hGDF15 antibody comprising:

a heavy chain variable region that contains

CDR1 comprising an amino acid sequence selected from the group consisting of the amino acid sequences of SEQ ID NOs: 38 and 39, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 95;

(11) an anti-hGDF15 antibody comprising:

a heavy chain variable region that contains

CDR1 comprising the amino acid sequence of SEQ ID NO: 18,

CDR2 comprising an amino acid sequence selected from the group consisting of the amino acid sequences of SEQ ID NOs: 52 and 66, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 95;

(12) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 77; and a light chain variable region that contains CDR1 comprising the amino acid sequence of SEQ ID NO: 21, CDR2 comprising the amino acid sequence of SEQ ID NO: 22, and CDR3 comprising the amino acid sequence of SEQ ID NO: 95;

(13) an anti-hGDF15 antibody comprising:

a heavy chain variable region that contains

CDR1 comprising an amino acid sequence selected from the group consisting of the amino acid sequences of SEQ ID NOs: 38 and 39, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 155, and CDR3 comprising the amino acid sequence of SEO ID NO: 23;

(14) an anti-hGDF15 antibody comprising:

a heavy chain variable region that contains

CDR1 comprising the amino acid sequence of SEQ ID NO: 18,

CDR2 comprising an amino acid sequence selected from the group consisting of the amino acid sequences of SEO ID NOs: 52, 66, and 152, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 155, and CDR3 comprising the amino acid sequence of SEQ ID NO: 23;

(15) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 77, and a light chain variable region that contains CDR1 comprising the amino acid sequence of SEQ ID NO: 21, CDR2 comprising the amino acid sequence of SEQ ID NO: 155, and CDR3 comprising the amino acid sequence of SEQ ID NO: 23;

(16) an anti-hGDF15 antibody comprising:

a heavy chain variable region that contains

CDR1 comprising an amino acid sequence selected from the group consisting of the amino acid sequences of SEQ ID NOs: 38 and 39, CDR2 comprising the amino acid sequence of SEQ ID NO: 19, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 157, and CDR3 comprising the amino acid sequence of SEQ ID NO: 23;

(17) an anti-hGDF15 antibody comprising:

a heavy chain variable region that contains

CDR1 comprising the amino acid sequence of SEQ ID NO: 18,

CDR2 comprising an amino acid sequence selected from the group consisting of the amino acid sequences of SEQ ID NOs: 52, 66, and 152, and CDR3 comprising the amino acid sequence of SEQ ID NO: 20; and a light chain variable region that contains CDR1 comprising the amino acid sequence of SEQ ID NO: 21, CDR2 comprising the amino acid sequence of SEQ ID NO: 157, and CDR3 comprising the amino acid sequence of SEQ ID NO: 23; and

(18) an anti-hGDF15 antibody comprising:

a heavy chain variable region that contains

CDR1 comprising the amino acid sequence of SEQ ID NO: 18,

CDR2 comprising the amino acid sequence of SEQ ID NO: 19, and

CDR3 comprising the amino acid sequence of SEQ ID NO: 77; and a light chain variable region that contains CDR1 comprising the amino acid sequence of SEQ ID NO: 21, CDR2 comprising the amino acid sequence of SEQ ID NO: 157, CDR3 comprising the amino acid sequence of SEQ ID NO: 23.

2. The anti-hGDF15 antibody of claim 1, wherein the heavy chain variable region comprises the amino acid sequence of SEQ ID NO: 4, and the light chain variable region comprises the amino acid sequence of SEQ ID NO: 5.

3. The antibody of claim 1, wherein the antibody comprises a heavy chain variable region comprising an amino acid sequence having 90% or more sequence identity to the amino acid sequence of SEQ ID NO: 8, or the amino acid sequence of SEQ ID NO: 8 or an amino acid sequence that differs from the amino acid sequence of SEQ ID NO: 8 by having amino acid modification of 1 to 20 amino acid residues;

and a light chain variable region comprising an amino acid sequence having 90% or more sequence identity to the amino acid sequence of SEQ ID NO: 9, or the amino acid sequence of SEQ ID NO: 9 or an amino acid sequence that differs from the amino acid sequence of SEQ ID NO: 9 by having amino acid modification of 1 to 20 amino acid residues.

4. The anti-hGDF15 antibody of claim 1, wherein the heavy chain variable region comprises the amino acid sequence of SEQ ID NO: 8 or an amino acid sequence that differs from the amino acid sequence of SEQ ID NO: 8 by having an amino acid substitution selected from 48R and 48S; and the light chain variable region comprises the amino acid sequence of SEQ ID NO: 9 or an amino acid sequence that differs from the amino acid sequence of SEQ ID NO: 9 by having an amino acid substitution selected from 69Y, 87K, and 87N.

5. A polynucleotide encoding the antibody of claim 1.

6. An expression vector comprising the polynucleotide of claim 5.

7. A transformed cell comprising the polynucleotide of claim 5.

8. A pharmaceutical composition comprising the anti-hGDF15 antibody of claim 1.

9. A method of treating a disease or symptom associated with GDF15, comprising administering an effective amount of the anti-hGDF15 antibody of claim 1 to a subject in need thereof.

10. The method of claim 9, wherein the disease or symptom associated with GDF15 is cancer.

11. The method of claim 9, wherein the disease or symptom associated with GDF15 is cachexia.

12. The method of claim 11, wherein the cachexia is cancer cachexia.

13. A method of decreasing blood GDF15 concentration, comprising administering an effective amount of the anti-hGDF15 antibody of claim 1 to a subject in need thereof.

14. The anti-hGDF15 antibody of claim 1, wherein the heavy variable region contains:

FR1 comprising the amino acid sequence of SEQ ID NO: 37 or 51; and/or wherein the light chain variable region contains:

FR2 comprising the amino acid sequence of SEQ ID NO: 105, and/or

FR3 comprising the amino acid sequence of SEQ ID NO: 116 or 117.

15. The anti-hGDF15 antibody of claim 4, wherein the heavy chain variable region comprises the amino acid sequence of SEQ ID NO: 8 and the light chain variable region comprises the amino acid sequence of SEQ ID NO: 9.

* * * * *

SEQUENCE LISTING

<160> NUMBER OF SEQ ID NOS: 157

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu

-continued

```
              20                    25                    30

Ala Glu Ala Ser Arg Ala Ser Phe Pro Gly Pro Ser Glu Leu His Ser
              35                    40                    45

Glu Asp Ser Arg Phe Arg Glu Leu Arg Lys Arg Tyr Glu Asp Leu Leu
          50                    55                    60

Thr Arg Leu Arg Ala Asn Gln Ser Trp Glu Asp Ser Asn Thr Asp Leu
65                    70                    75                    80

Val Pro Ala Pro Ala Val Arg Ile Leu Thr Pro Glu Val Arg Leu Gly
                  85                    90                    95

Ser Gly Gly His Leu His Leu Arg Ile Ser Arg Ala Ala Leu Pro Glu
                  100                   105                   110

Gly Leu Pro Glu Ala Ser Arg Leu His Arg Ala Leu Phe Arg Leu Ser
          115                   120                   125

Pro Thr Ala Ser Arg Ser Trp Asp Val Thr Arg Pro Leu Arg Arg Gln
          130                   135                   140

Leu Ser Leu Ala Arg Pro Gln Ala Pro Ala Leu His Leu Arg Leu Ser
145                   150                   155                   160

Pro Pro Pro Ser Gln Ser Asp Gln Leu Leu Ala Glu Ser Ser Ser Ala
                  165                   170                   175

Arg Pro Gln Leu Glu Leu His Leu Arg Pro Gln Ala Ala Arg Gly Arg
              180                   185                   190

Arg Arg Ala Arg Ala Arg Asn Gly Asp His Cys Pro Leu Gly Pro Gly
              195                   200                   205

Arg Cys Cys Arg Leu His Thr Val Arg Ala Ser Leu Glu Asp Leu Gly
          210                   215                   220

Trp Ala Asp Trp Val Leu Ser Pro Arg Glu Val Gln Val Thr Met Cys
225                   230                   235                   240

Ile Gly Ala Cys Pro Ser Gln Phe Arg Ala Ala Asn Met His Ala Gln
                  245                   250                   255

Ile Lys Thr Ser Leu His Arg Leu Lys Pro Asp Thr Val Pro Ala Pro
              260                   265                   270

Cys Cys Val Pro Ala Ser Tyr Asn Pro Met Val Leu Ile Gln Lys Thr
              275                   280                   285

Asp Thr Gly Val Ser Leu Gln Thr Tyr Asp Asp Leu Leu Ala Lys Asp
          290                   295                   300

Cys His Cys Ile
305
```

```
<210> SEQ ID NO 2
<211> LENGTH: 112
<212> TYPE: PRT
<213> ORGANISM: Homo sapiens

<400> SEQUENCE: 2

Ala Arg Asn Gly Asp His Cys Pro Leu Gly Pro Gly Arg Cys Cys Arg
1                 5                    10                    15

Leu His Thr Val Arg Ala Ser Leu Glu Asp Leu Gly Trp Ala Asp Trp
              20                    25                    30

Val Leu Ser Pro Arg Glu Val Gln Val Thr Met Cys Ile Gly Ala Cys
          35                    40                    45

Pro Ser Gln Phe Arg Ala Ala Asn Met His Ala Gln Ile Lys Thr Ser
      50                    55                    60

Leu His Arg Leu Lys Pro Asp Thr Val Pro Ala Pro Cys Cys Val Pro
65                    70                    75                    80
```

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 3
<211> LENGTH: 14
<212> TYPE: PRT
<213> ORGANISM: Homo sapiens

<400> SEQUENCE: 3

Asp His Cys Pro Leu Gly Pro Gly Arg Cys Cys Arg Leu His
1               5                   10

<210> SEQ ID NO 4
<211> LENGTH: 134
<212> TYPE: PRT
<213> ORGANISM: Mus musculus

<400> SEQUENCE: 4

Met Arg Met Leu Ser Val Leu Tyr Leu Leu Ser Ala Leu Pro Gly Ile
1               5                   10                  15

Leu Ser Asp Val Gln Leu Gln Glu Ser Gly Pro Ser Leu Val Arg Pro
                20                  25                  30

Ser Gln Thr Leu Ser Leu Thr Cys Thr Val Thr Gly Phe Ser Ile Asn
            35                  40                  45

Ser Asp Cys Tyr Trp Ile Trp Ile Arg Gln Phe Pro Gly Asn Lys Leu
        50                  55                  60

Glu Tyr Ile Gly Tyr Thr Phe Tyr Ser Gly Ile Thr Tyr Tyr Asn Pro
65                  70                  75                  80

Ser Leu Ala Ser Arg Thr Tyr Ile Thr Arg Asp Thr Ser Lys Asn Gln
                85                  90                  95

Phe Ser Leu Lys Leu Asn Ser Val Thr Thr Glu Asp Thr Ala Thr Tyr
            100                 105                 110

Tyr Cys Ala Arg Asp Cys Asp Tyr Ala Met Asp Tyr Trp Gly Gln Gly
        115                 120                 125

Thr Ser Val Thr Val Ser
        130

<210> SEQ ID NO 5
<211> LENGTH: 131
<212> TYPE: PRT
<213> ORGANISM: Mus musculus

<400> SEQUENCE: 5

Met Gly Tyr Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
                20                  25                  30

Ala Ser Leu Gly Asp Arg Val Thr Ile Ser Cys Arg Ala Ser Gln Asp
            35                  40                  45

Ile Ser Asn Tyr Leu Asn Trp Tyr Gln Gln Lys Pro Asp Gly Thr Val
        50                  55                  60

Lys Leu Leu Ile His Tyr Thr Ser Thr Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn

```
                100              105              110
Thr Leu Pro Trp Thr Phe Gly Gly Gly Thr Lys Leu Glu Ile Lys Arg
        115              120              125

Ala Asp Ala
    130

<210> SEQ ID NO 6
<211> LENGTH: 136
<212> TYPE: PRT
<213> ORGANISM: Mus musculus

<400> SEQUENCE: 6

Met Asp Arg Leu Thr Phe Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Asn Thr His Gly Met Gly Val Gly Trp Ile Arg Gln Pro Ser Gly Lys
    50                  55                  60

Gly Leu Glu Trp Leu Ala Asn Ile Trp Trp Asn Asp Asp Lys Tyr Tyr
65                  70                  75                  80

Asn Ser Ala Leu Lys Ser Arg Leu Thr Leu Ser Lys Asp Thr Ser Asn
            85                  90                  95

Asn Gln Val Phe Leu Lys Ile Ser Ser Val Asp Thr Ala Asp Thr Ala
            100             105             110

Thr Tyr Phe Cys Ala Gln Val Ala Trp Asp Trp Phe Ala Tyr Trp Gly
        115             120             125

Gln Gly Thr Leu Val Thr Ile Ser
    130             135

<210> SEQ ID NO 7
<211> LENGTH: 132
<212> TYPE: PRT
<213> ORGANISM: Mus musculus

<400> SEQUENCE: 7

Met Asp Ser Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Ala Ser Leu Gly Glu Glu Ile Thr Leu Thr Cys Ser Ala Ser
        35                  40                  45

Ser Ser Val Arg Tyr Met His Trp Tyr Gln Gln Lys Ser Gly Thr Ser
    50                  55                  60

Pro Lys Val Leu Ile Tyr Ser Thr Ser Asn Leu Ala Ser Gly Val Pro
65                  70                  75                  80

Ser Arg Phe Ser Gly Ser Gly Ser Gly Thr Phe Tyr Ser Leu Thr Ile
            85                  90                  95

Ser Ser Val Glu Ala Glu Asp Ala Ala Asp Tyr Tyr Cys His Gln Trp
            100             105             110

Ser Ser Tyr Pro Trp Thr Phe Gly Gly Gly Thr Lys Leu Glu Ile Lys
        115             120             125

Arg Ala Asp Ala
    130
```

<210> SEQ ID NO 8
<211> LENGTH: 155
<212> TYPE: PRT
<213> ORGANISM: Artificial Sequence
<220> FEATURE:
<223> OTHER INFORMATION: Synthetic sequence, HuMAB2

<400> SEQUENCE: 8

Met Lys His Leu Trp Phe Leu Leu Leu Ala Ala Pro Arg Trp Val
1               5                   10                  15

Leu Ser Gln Val Gln Leu Gln Glu Ser Gly Pro Gly Leu Val Lys Pro
            20                  25                  30

Ser Glu Thr Leu Ser Leu Thr Cys Thr Val Ser Gly Phe Ser Ile Asn
        35                  40                  45

Ser Asp Cys Tyr Trp Ile Trp Ile Arg Gln Pro Pro Gly Lys Gly Leu
    50                  55                  60

Glu Tyr Ile Gly Tyr Thr Phe Tyr Ser Gly Ile Thr Tyr Tyr Asn Pro
65                  70                  75                  80

Ser Leu Ala Ser Arg Thr Thr Ile Ser Arg Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asp Cys Asp Tyr Ala Met Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly
145                 150                 155

<210> SEQ ID NO 9
<211> LENGTH: 140
<212> TYPE: PRT
<213> ORGANISM: Artificial Sequence
<220> FEATURE:
<223> OTHER INFORMATION: Synthetic sequence, HuMAB2

<400> SEQUENCE: 9

Met Arg Val Pro Ala Gln Leu Leu Gly Leu Leu Leu Leu Trp Leu Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Asn Tyr Leu Asn Trp Tyr Gln Gln Lys Pro Gly Lys Ala Val
    50                  55                  60

Lys Leu Leu Ile His Tyr Thr Ser Thr Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Gly Asn
            100                 105                 110

Thr Leu Pro Trp Thr Phe Gly Gln Gly Thr Lys Leu Glu Ile Lys Arg
        115                 120                 125

Thr Val Ala Ala Pro Ser Val Phe Ile Phe Pro Pro
    130                 135                 140

<210> SEQ ID NO 10
<211> LENGTH: 464

<212> TYPE: PRT
<213> ORGANISM: Artificial Sequence
<220> FEATURE:
<223> OTHER INFORMATION: Synthetic sequence, HuMAB2

<400> SEQUENCE: 10

Met Lys His Leu Trp Phe Leu Leu Leu Ala Ala Pro Arg Trp Val
1               5                   10                  15

Leu Ser Gln Val Gln Leu Gln Glu Ser Gly Pro Gly Leu Val Lys Pro
                20                  25                  30

Ser Glu Thr Leu Ser Leu Thr Cys Thr Val Ser Gly Phe Ser Ile Asn
            35                  40                  45

Ser Asp Cys Tyr Trp Ile Trp Ile Arg Gln Pro Pro Gly Lys Gly Leu
        50                  55                  60

Glu Tyr Ile Gly Tyr Thr Phe Tyr Ser Gly Ile Thr Tyr Tyr Asn Pro
65                  70                  75                  80

Ser Leu Ala Ser Arg Thr Thr Ile Ser Arg Asp Thr Ser Lys Asn Gln
                85                  90                  95

Phe Ser Leu Lys Leu Ser Ser Val Thr Ala Ala Asp Thr Ala Val Tyr
                100                 105                 110

Tyr Cys Ala Arg Asp Cys Asp Tyr Ala Met Asp Tyr Trp Gly Gln Gly
            115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
            355                 360                 365

Leu Pro Pro Ser Arg Glu Glu Met Thr Lys Asn Gln Val Ser Leu Thr
    370                 375                 380

-continued

```
Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
            450                 455                 460

<210> SEQ ID NO 11
<211> LENGTH: 234
<212> TYPE: PRT
<213> ORGANISM: Artificial Sequence
<220> FEATURE:
<223> OTHER INFORMATION: Synthetic sequence, HuMAB2

<400> SEQUENCE: 11

Met Arg Val Pro Ala Gln Leu Leu Gly Leu Leu Leu Leu Trp Leu Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45

Ile Ser Asn Tyr Leu Asn Trp Tyr Gln Gln Lys Pro Gly Lys Ala Val
        50                  55                  60

Lys Leu Leu Ile His Tyr Thr Ser Thr Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Gly Asn
                100                 105                 110

Thr Leu Pro Trp Thr Phe Gly Gln Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
            165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230

<210> SEQ ID NO 12
<211> LENGTH: 7
<212> TYPE: PRT
<213> ORGANISM: Mus musculus

<400> SEQUENCE: 12

Thr His Gly Met Gly Val Gly
```

```
1               5

<210> SEQ ID NO 13
<211> LENGTH: 16
<212> TYPE: PRT
<213> ORGANISM: Mus musculus

<400> SEQUENCE: 13

Asn Ile Trp Trp Asn Asp Asp Lys Tyr Tyr Asn Ser Ala Leu Lys Ser
1               5                   10                  15

<210> SEQ ID NO 14
<211> LENGTH: 8
<212> TYPE: PRT
<213> ORGANISM: Mus musculus

<400> SEQUENCE: 14

Val Ala Trp Asp Trp Phe Ala Tyr
1               5

<210> SEQ ID NO 15
<211> LENGTH: 10
<212> TYPE: PRT
<213> ORGANISM: Mus musculus

<400> SEQUENCE: 15

Ser Ala Ser Ser Ser Val Arg Tyr Met His
1               5                   10

<210> SEQ ID NO 16
<211> LENGTH: 7
<212> TYPE: PRT
<213> ORGANISM: Mus musculus

<400> SEQUENCE: 16

Ser Thr Ser Asn Leu Ala Ser
1               5

<210> SEQ ID NO 17
<211> LENGTH: 9
<212> TYPE: PRT
<213> ORGANISM: Mus musculus

<400> SEQUENCE: 17

His Gln Trp Ser Ser Tyr Pro Trp Thr
1               5

<210> SEQ ID NO 18
<211> LENGTH: 6
<212> TYPE: PRT
<213> ORGANISM: Mus musculus

<400> SEQUENCE: 18

Ser Asp Cys Tyr Trp Ile
1               5

<210> SEQ ID NO 19
<211> LENGTH: 16
<212> TYPE: PRT
<213> ORGANISM: Mus musculus

<400> SEQUENCE: 19

Tyr Thr Phe Tyr Ser Gly Ile Thr Tyr Tyr Asn Pro Ser Leu Ala Ser
1               5                   10                  15
```

-continued

```
<210> SEQ ID NO 20
<211> LENGTH: 8
<212> TYPE: PRT
<213> ORGANISM: Mus musculus

<400> SEQUENCE: 20

Asp Cys Asp Tyr Ala Met Asp Tyr
1               5

<210> SEQ ID NO 21
<211> LENGTH: 11
<212> TYPE: PRT
<213> ORGANISM: Mus musculus

<400> SEQUENCE: 21

Arg Ala Ser Gln Asp Ile Ser Asn Tyr Leu Asn
1               5                   10

<210> SEQ ID NO 22
<211> LENGTH: 7
<212> TYPE: PRT
<213> ORGANISM: Mus musculus

<400> SEQUENCE: 22

Tyr Thr Ser Thr Leu His Ser
1               5

<210> SEQ ID NO 23
<211> LENGTH: 9
<212> TYPE: PRT
<213> ORGANISM: Mus musculus

<400> SEQUENCE: 23

Gln Gln Gly Asn Thr Leu Pro Trp Thr
1               5

<210> SEQ ID NO 24
<211> LENGTH: 465
<212> TYPE: DNA
<213> ORGANISM: Artificial Sequence
<220> FEATURE:
<223> OTHER INFORMATION: Synthetic sequence, HuMAB2

<400> SEQUENCE: 24
atgaagcacc tgtggtttct gctgctgctg ccgctccca gatgggtgct gtctcaggtg      60
cagctgcagg aatctggccc tggcctcgtg aagcccagcg agacactgag cctgacctgt     120
accgtgtccg gcttcagcat caacagcgac tgctactgga tctggatcag acagcccct     180 ggcaagggcc tggagtacat cggctacacc ttctacagcg gcatcaccta ctacaacccc     240
agcctggcca gccggaccac catcagcaga gacaccagca gaaccagtt cagcctgaag     300 ctgagcagcg tgacagccgc cgataccgcc gtgtactact cgccagaga ctgcgactac     360 gccatggact attggggcca gggcaccctc gtgaccgtgt ctagcgcctc tacaaagggc     420
cccagcgtgt ccctctggc ccctagcagc aagagcacat ctggc                     465

<210> SEQ ID NO 25
<211> LENGTH: 420
<212> TYPE: DNA
<213> ORGANISM: Artificial Sequence
<220> FEATURE:
<223> OTHER INFORMATION: Synthetic sequence, HuMAB2

<400> SEQUENCE: 25
```

-continued

```
atgagagtgc ctgctcagct gctgggactg ctgctgctgt ggctgcctgg cgctagatgc      60
gacatccaga tgacccagag ccccagcagc ctgtctgcca gcgtgggcga cagagtgacc     120
atcacctgta gagccagcca ggacatcagc aactacctga actggtatca gcagaaaccc     180
ggcaaggccg tgaagctgct gatccactac accagcaccc tgcacagcgg cgtgcccagc     240
agattttctg gcagcggctc cggcaccgac tacaccctga caatcagctc cctgcagccc     300
gaggacttcg ctacctactt ctgtcagcaa ggcaacaccc tgccctggac ctttggccag     360
ggcaccaagc tggaaatcaa gcggacagtg gccgctccca gcgtgttcat cttcccacct     420
```

```
<210> SEQ ID NO 26
<211> LENGTH: 1395
<212> TYPE: DNA
<213> ORGANISM: Artificial Sequence
<220> FEATURE:
<223> OTHER INFORMATION: Synthetic sequence, HuMAB2

<400> SEQUENCE: 26
atgaagcacc tgtggtttct gctgctgctg gccgctccca gatgggtgct gtctcaggtg      60
cagctgcagg aatctggccc tggcctcgtg aagcccagcg agacactgag cctgacctgt     120
accgtgtccg gcttcagcat caacagcgac tgctactgga tctggatcag acagcccct     180 ggcaagggcc tggagtacat cggctacacc ttctacagcg gcatcaccta ctacaacccc     240
agcctggcca gccggaccac catcagcaga gacaccagca gaaccagtt cagcctgaag     300 ctgagcagcg tgacagccgc cgataccgcc gtgtactact gcgccagaga ctgcgactac     360
gccatggact attggggcca gggcaccctc gtgaccgtgt ctagcgcctc tacaaagggc     420
cccagcgtgt tccctctggc ccctagcagc aagagcacat ctggcggaac agccgccctg     480
ggctgcctcg tgaaagacta cttccccgag cccgtgacag tgtcctggaa ctctggcgcc     540
ctgacaagcg gcgtgcacac ctttccagcc gtgctgcaga gcagcggcct gtactctctg     600
tccagcgtcg tgactgtgcc cagcagctct ctgggcaccc agacctacat ctgcaacgtg     660
aaccacaagc ccagcaacac caaggtggac aagaaggtgg aacccaagag ctgcgacaag     720
acccacacct gtccccttg tcctgccccc gaactgctgg gaggcccttc cgtgttcctg     780
ttccccccaa agcccaagga caccctgatg atcagcagaa cccccgaagt gacctgcgtg     840
gtggtggacg tgtcccacga ggaccctgaa gtgaagttca attggtacgt ggacggcgtg     900
gaagtgcaca cgccaagac caagcctaga gaggaacagt acaacagcac ctaccgggtg     960
gtgtccgtgc tgacagtgct gcaccaggac tggctgaacg gcaaagagta caagtgcaag    1020
gtgtccaaca aggccctgcc tgcccccatc gagaaaacca tctccaaggc caagggacag    1080 cccgcgagc cccaggtgta cactgcct ccaagccggg aagagatgac caagaatcag    1140
gtgtccctga catgcctcgt gaagggcttc taccctccg atattgccgt ggaatgggag    1200
agcaacggcc agcccgagaa caactacaag accacccccc ctgtgctgga cagcgacggc    1260
tcattcttcc tgtacagcaa gctgaccgtg gacaagtccc ggtggcagca gggcaacgtg    1320
ttcagctgca gcgtgatgca cgaggccctg cacaaccact acacccagaa gtccctgtcc    1380
ctgagccccg gctaa                                                      1395
```

```
<210> SEQ ID NO 27
<211> LENGTH: 705
<212> TYPE: DNA
<213> ORGANISM: Artificial Sequence
<220> FEATURE:
```

<223> OTHER INFORMATION: Synthetic sequence, HuMAB2

<400> SEQUENCE: 27
atgagagtgc ctgctcagct gctgggactg ctgctgctgt ggctgcctgg cgctagatgc      60
gacatccaga tgacccagag ccccagcagc ctgtctgcca gcgtgggcga cagagtgacc     120
atcacctgta gagccagcca ggacatcagc aactacctga actggtatca gcagaaaccc     180
ggcaaggccg tgaagctgct gatccactac accagcaccc tgcacagcgg cgtgcccagc     240
agattttctg gcagcggctc cggcaccgac tacaccctga caatcagctc cctgcagccc     300
gaggacttcg ctacctactt ctgtcagcaa ggcaacaccc tgccctggac ctttggccag     360
ggcaccaagc tggaaatcaa gcggacagtg gccgctccca gcgtgttcat cttcccacct     420
agcgacgagc agctgaagtc tggcaccgcc tctgtcgtgt gcctgctgaa caacttctac     480
ccccgcgagg ccaaggtgca gtggaaggtg acaatgcccc tgcagtccgg caacagccag     540
gaaagcgtga ccgagcagga cagcaaggac tccacctaca gcctgtcctc caccctgacc     600
ctgagcaagg ccgactacga gaagcacaag gtgtacgcct gcgaagtgac ccaccagggc     660
ctgagcagcc ctgtgaccaa gagcttcaac cggggcgagt gctga                     705

<210> SEQ ID NO 28
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 28

Ala Arg Asn Gly Asp Ala Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 29

Ala Arg Asn Gly Asp His Cys Pro Leu Gly Pro Gly Ala Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser

-continued

```
        50              55              60

Leu His Arg Leu Lys Pro Asp Thr Val Pro Ala Pro Cys Cys Val Pro
65              70              75              80

Ala Ser Tyr Asn Pro Met Val Leu Ile Gln Lys Thr Asp Thr Gly Val
                85              90              95

Ser Leu Gln Thr Tyr Asp Asp Leu Leu Ala Lys Asp Cys His Cys Ile
            100             105             110

<210> SEQ ID NO 30
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 30

Ala Arg Asn Gly Asp His Cys Pro Leu Gly Pro Gly Arg Cys Cys Ala
1               5               10              15

Leu His Thr Val Arg Ala Ser Leu Glu Asp Leu Gly Trp Ala Asp Trp
                20              25              30

Val Leu Ser Pro Arg Glu Val Gln Val Thr Met Cys Ile Gly Ala Cys
            35              40              45

Pro Ser Gln Phe Arg Ala Ala Asn Met His Ala Gln Ile Lys Thr Ser
    50              55              60

Leu His Arg Leu Lys Pro Asp Thr Val Pro Ala Pro Cys Cys Val Pro
65              70              75              80

Ala Ser Tyr Asn Pro Met Val Leu Ile Gln Lys Thr Asp Thr Gly Val
                85              90              95

Ser Leu Gln Thr Tyr Asp Asp Leu Leu Ala Lys Asp Cys His Cys Ile
            100             105             110

<210> SEQ ID NO 31
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 31

Ala Arg Asn Gly Asp His Cys Pro Leu Gly Pro Gly Ala Cys Cys Ala
1               5               10              15

Leu His Thr Val Arg Ala Ser Leu Glu Asp Leu Gly Trp Ala Asp Trp
                20              25              30

Val Leu Ser Pro Arg Glu Val Gln Val Thr Met Cys Ile Gly Ala Cys
            35              40              45

Pro Ser Gln Phe Arg Ala Ala Asn Met His Ala Gln Ile Lys Thr Ser
    50              55              60

Leu His Arg Leu Lys Pro Asp Thr Val Pro Ala Pro Cys Cys Val Pro
65              70              75              80

Ala Ser Tyr Asn Pro Met Val Leu Ile Gln Lys Thr Asp Thr Gly Val
                85              90              95

Ser Leu Gln Thr Tyr Asp Asp Leu Leu Ala Lys Asp Cys His Cys Ile
            100             105             110

<210> SEQ ID NO 32
<211> LENGTH: 112
<212> TYPE: PRT
<213> ORGANISM: Artificial Sequence
<220> FEATURE:
```

<223> OTHER INFORMATION: Synthetic sequence, hGDF15 mutant

<400> SEQUENCE: 32

Ala Arg Asn Gly Asp His Cys Pro Leu Gly Pro Ala Ala Cys Cys Ala
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 33
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 33

Ala Arg Asn Gly Asp His Cys Pro Leu Gly Pro Ala Ala Cys Cys Ala
1               5                   10                  15

Ala His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 34
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 34

Ala Arg Asn Gly Asp His Cys Pro Leu Ala Ala Ala Ala Cys Cys Ala
1               5                   10                  15

Ala His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro 65                70                75                80

Ala Ser Tyr Asn Pro Met Val Leu Ile Gln Lys Thr Asp Thr Gly Val
                85                90                95

Ser Leu Gln Thr Tyr Asp Asp Leu Leu Ala Lys Asp Cys His Cys Ile
                100               105               110

<210> SEQ ID NO 35
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 35

Ala Arg Asn Gly Asp His Cys Ala Ala Ala Ala Ala Ala Cys Cys Ala
1                5                 10                15

Ala His Thr Val Arg Ala Ser Leu Glu Asp Leu Gly Trp Ala Asp Trp
                20                25                30

Val Leu Ser Pro Arg Glu Val Gln Val Thr Met Cys Ile Gly Ala Cys
                35                40                45

Pro Ser Gln Phe Arg Ala Ala Asn Met His Ala Gln Ile Lys Thr Ser
        50                55                60

Leu His Arg Leu Lys Pro Asp Thr Val Pro Ala Pro Cys Cys Val Pro
65                70                75                80

Ala Ser Tyr Asn Pro Met Val Leu Ile Gln Lys Thr Asp Thr Gly Val
                85                90                95

Ser Leu Gln Thr Tyr Asp Asp Leu Leu Ala Lys Asp Cys His Cys Ile
                100               105               110

<210> SEQ ID NO 36
<211> LENGTH: 112
<212> TYPE: PRT
<213> ORGANISM: Artificial Sequence
<220> FEATURE:
<223> OTHER INFORMATION: Synthetic sequence, hGDF15 mutant

<400> SEQUENCE: 36

Ala Arg Asn Gly Asp His Cys Pro Leu Gly Pro Gly Arg Cys Cys Arg
1                5                 10                15

Leu His Thr Val Arg Ala Ser Leu Glu Asp Leu Gly Trp Ala Asp Trp
                20                25                30

Val Leu Ser Pro Arg Glu Val Gln Val Thr Met Cys Ile Gly Ala Cys
                35                40                45

Pro Ser Gln Phe Arg Ala Ala Asn Met His Ala Gln Ile Lys Thr Ser
        50                55                60

Leu His Arg Leu Lys Pro Asp Ala Val Pro Ala Pro Cys Cys Val Pro
65                70                75                80

Ala Ser Tyr Asn Pro Met Val Leu Ile Gln Lys Thr Asp Thr Gly Val
                85                90                95

Ser Leu Gln Thr Tyr Asp Asp Leu Leu Ala Lys Asp Cys His Cys Ile
                100               105               110

<210> SEQ ID NO 37
<211> LENGTH: 30
<212> TYPE: PRT
<213> ORGANISM: Artificial Sequence
<220> FEATURE:
<223> OTHER INFORMATION: Synthetic sequence, HuMAB2 variant

<400> SEQUENCE: 37

```
Asp Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Arg
            20                  25                  30

<210> SEQ ID NO 38
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 38

Arg Asp Cys Tyr Trp Ile
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 39

Asp Asp Cys Tyr Trp Ile
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 40

Ser Arg Cys Tyr Trp Ile
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 41

Ser Ser Cys Tyr Trp Ile
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 42

Ser Phe Cys Tyr Trp Ile
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic sequence, HuMAB2 variant
```

<400> SEQUENCE: 43

Ser Asp Cys Arg Trp Ile
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 44

Ser Asp Cys Gln Trp Ile
1               5

<210> SEQ ID NO 45
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 45

Tyr Thr Phe Arg Ser Gly Ile Thr Tyr Tyr Asn Pro Ser Leu Ala Ser
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 46

Tyr Thr Phe Tyr Asp Gly Ile Thr Tyr Tyr Asn Pro Ser Leu Ala Ser
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 47

Tyr Thr Phe Tyr Arg Gly Ile Thr Tyr Tyr Asn Pro Ser Leu Ala Ser
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 48

Tyr Thr Phe Tyr Tyr Gly Ile Thr Tyr Tyr Asn Pro Ser Leu Ala Ser
1               5                   10                  15

<210> SEQ ID NO 49
<211> LENGTH: 8
<212> TYPE: PRT
<213> ORGANISM: Artificial Sequence
<220> FEATURE:
<223> OTHER INFORMATION: Synthetic sequence, HuMAB2 variant -continued

```
<400> SEQUENCE: 49

Asp Cys Arg Tyr Ala Met Asp Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 50

Asp Cys Phe Tyr Ala Met Asp Tyr
1               5

<210> SEQ ID NO 51
<211> LENGTH: 30
<212> TYPE: PRT
<213> ORGANISM: Artificial Sequence
<220> FEATURE:
<223> OTHER INFORMATION: Synthetic sequence, HuMAB2 variant

<400> SEQUENCE: 51

Asp Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Ser
            20                  25                  30

<210> SEQ ID NO 52
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 52

Tyr Thr Tyr Tyr Ser Gly Ile Thr Tyr Tyr Asn Pro Ser Leu Ala Ser
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 53

Tyr Thr Phe Ala Ser Gly Ile Thr Tyr Tyr Asn Pro Ser Leu Ala Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 54

Tyr Thr Phe Leu Ser Gly Ile Thr Tyr Tyr Asn Pro Ser Leu Ala Ser
1               5                   10                  15

<210> SEQ ID NO 55
<211> LENGTH: 16
<212> TYPE: PRT
<213> ORGANISM: Artificial Sequence
<220> FEATURE:
```

<223> OTHER INFORMATION: Synthetic sequence, HuMAB2 variant

<400> SEQUENCE: 55

Tyr Thr Phe Asn Ser Gly Ile Thr Tyr Tyr Asn Pro Ser Leu Ala Ser
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 56

Tyr Thr Phe Thr Ser Gly Ile Thr Tyr Tyr Asn Pro Ser Leu Ala Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 57

Tyr Thr Phe Trp Ser Gly Ile Thr Tyr Tyr Asn Pro Ser Leu Ala Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 58

Tyr Thr Phe Tyr Ser Gly His Thr Tyr Tyr Asn Pro Ser Leu Ala Ser
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 59

Tyr Thr Phe Tyr Ser Gly Leu Thr Tyr Tyr Asn Pro Ser Leu Ala Ser
1               5                   10                  15

<210> SEQ ID NO 60
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 60

Tyr Thr Phe Tyr Ser Gly Asn Thr Tyr Tyr Asn Pro Ser Leu Ala Ser
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: Synthetic sequence, HuMAB2 variant -continued

<400> SEQUENCE: 61

Tyr Thr Phe Tyr Ser Gly Gln Thr Tyr Tyr Asn Pro Ser Leu Ala Ser
1               5                   10                  15

<210> SEQ ID NO 62
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 62

Tyr Thr Phe Tyr Ser Gly Ile Thr Tyr Tyr His Pro Ser Leu Ala Ser
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 63

Tyr Thr Phe Tyr Ser Gly Ile Thr Tyr Tyr Lys Pro Ser Leu Ala Ser
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 64

Tyr Thr Phe Tyr Ser Gly Ile Thr Tyr Tyr Gln Pro Ser Leu Ala Ser
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 65

Tyr Thr Phe Tyr Ser Gly Ile Thr Tyr Tyr Arg Pro Ser Leu Ala Ser
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 66

Tyr Thr Phe Tyr Ser Gly Ile Thr Tyr Tyr Asn Pro Ser Leu Arg Ser
1               5                   10                  15

<210> SEQ ID NO 67
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 67

Gln Cys Asp Tyr Ala Met Asp Tyr
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 68

Asp Cys Glu Tyr Ala Met Asp Tyr
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 69

Asp Cys His Tyr Ala Met Asp Tyr
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 70

Asp Cys Lys Tyr Ala Met Asp Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 71

Asp Cys Asn Tyr Ala Met Asp Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 72

Asp Cys Gln Tyr Ala Met Asp Tyr
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 73

-continued

```
Asp Cys Ser Tyr Ala Met Asp Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 74

Asp Cys Thr Tyr Ala Met Asp Tyr
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 75

Asp Cys Asp Ala Ala Met Asp Tyr
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 76

Asp Cys Asp Asp Ala Met Asp Tyr
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 77

Asp Cys Asp Phe Ala Met Asp Tyr
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 78

Asp Cys Asp Asn Ala Met Asp Tyr
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 79
```

```
Asp Cys Asp Gln Ala Met Asp Tyr
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic sequence, HuMAB2 variant

<400> SEQUENCE: 80

Asp Cys Asp Tyr Ala Phe Asp Tyr
1               5

<210> SEQ ID NO 81
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 81

Arg Ala Ser Arg Asp Ile Ser Asn Tyr Leu Asn
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 82

Arg Ala Ser Gln Glu Ile Ser Asn Tyr Leu Asn
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 83

Arg Ala Ser Gln Arg Ile Ser Asn Tyr Leu Asn
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 84

Arg Ala Ser Gln Ser Ile Ser Asn Tyr Leu Asn
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 85

Arg Ala Ser Gln Lys Ile Ser Asn Tyr Leu Asn
```

-continued

```
1               5                    10
```

<210> SEQ ID NO 86
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 86

```
Arg Ala Ser Gln Asp Ile Asp Asn Tyr Leu Asn
1               5                    10
```

<210> SEQ ID NO 87
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 87

```
Arg Ala Ser Gln Asp Ile Arg Asn Tyr Leu Asn
1               5                    10
```

<210> SEQ ID NO 88
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 88

```
Arg Ala Ser Gln Asp Ile Phe Asn Tyr Leu Asn
1               5                    10
```

<210> SEQ ID NO 89
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 89

```
Arg Ala Ser Gln Asp Ile Tyr Asn Tyr Leu Asn
1               5                    10
```

<210> SEQ ID NO 90
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 90

```
Tyr Thr Ser Arg Leu His Ser
1               5
```

<210> SEQ ID NO 91
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 91

```
Gln Gln Phe Asn Thr Leu Pro Trp Thr
1               5
```

```
<210> SEQ ID NO 92
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 92

Gln Gln Tyr Asn Thr Leu Pro Trp Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 93

Gln Gln Gly Glu Thr Leu Pro Trp Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 94

Gln Gln Gly Arg Thr Leu Pro Trp Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 95

Gln Gln Gly Asp Thr Leu Pro Trp Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 96

Gln Gln Gly Phe Thr Leu Pro Trp Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 97

Gln Gln Gly Asn Asp Leu Pro Trp Thr
1               5
```

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 98

Gln Gln Gly Asn Arg Leu Pro Trp Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 99

Gln Gln Gly Asn Phe Leu Pro Trp Thr
1               5

<210> SEQ ID NO 100
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 100

Arg Ala Ser Gln His Ile Ser Asn Tyr Leu Asn
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 101

Arg Ala Ser Gln Tyr Ile Ser Asn Tyr Leu Asn
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 102

Arg Ala Ser Gln Asp Ile Gln Asn Tyr Leu Asn
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 103

Arg Ala Ser Gln Asp Ile Trp Asn Tyr Leu Asn
1               5                   10

-continued

```
<210> SEQ ID NO 104
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 104

Arg Ala Ser Gln Asp Ile Ser Gln Tyr Leu Asn
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic sequence, HuMAB2 variant

<400> SEQUENCE: 105

Trp Tyr Gln Gln Lys Pro Gly Lys Ala Val Lys Leu Leu Ile Tyr
1               5                   10                  15

<210> SEQ ID NO 106
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 106

Phe Thr Ser Thr Leu His Ser
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 107

His Thr Ser Thr Leu His Ser
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 108

Tyr Thr Asp Thr Leu His Ser
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 109

Tyr Thr Glu Thr Leu His Ser
1               5

<210> SEQ ID NO 110
```

```
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 110

Tyr Thr Arg Thr Leu His Ser
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 111

Tyr Thr Tyr Thr Leu His Ser
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 112

Tyr Thr Ser Lys Leu His Ser
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 113

Tyr Thr Ser Asn Leu His Ser
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 114

Tyr Thr Ser Tyr Leu His Ser
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 115

Tyr Thr Ser Thr Leu Gln Ser
1               5

<210> SEQ ID NO 116
<211> LENGTH: 32
```

-continued

```
<212> TYPE: PRT
<213> ORGANISM: Artificial Sequence
<220> FEATURE:
<223> OTHER INFORMATION: Synthetic sequence, HuMAB2 variant

<400> SEQUENCE: 116

Gly Val Pro Ser Arg Phe Ser Gly Ser Gly Lys Gly Thr Asp Tyr Thr
1               5                   10                  15

Leu Thr Ile Ser Ser Leu Gln Pro Glu Asp Phe Ala Thr Tyr Phe Cys
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Synthetic sequence, HuMAB2 variant

<400> SEQUENCE: 117

Gly Val Pro Ser Arg Phe Ser Gly Ser Gly Asn Gly Thr Asp Tyr Thr
1               5                   10                  15

Leu Thr Ile Ser Ser Leu Gln Pro Glu Asp Phe Ala Thr Tyr Phe Cys
            20                  25                  30

<210> SEQ ID NO 118
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 118

Gln Gln Ala Asn Thr Leu Pro Trp Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 119

Gln Gln Asn Asn Thr Leu Pro Trp Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 120

Gln Gln Ser Asn Thr Leu Pro Trp Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 121

Gln Gln Gly His Thr Leu Pro Trp Thr
```

```
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 122

Gln Gln Gly Gln Thr Leu Pro Trp Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 123

Gln Gln Gly Thr Thr Leu Pro Trp Thr
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 124

Gln Gln Gly Tyr Thr Leu Pro Trp Thr
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 125

Gln Gln Gly Asn Ser Leu Pro Trp Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 126

Gln Gln Gly Asn Thr Phe Pro Trp Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 127

Gln Gln Gly Asn Thr His Pro Trp Thr
1               5
```

```
<210> SEQ ID NO 128
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 128

Gln Gln Gly Asn Thr Ile Pro Trp Thr
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 129

Gln Gln Gly Asn Thr Asn Pro Trp Thr
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 130

Gln Gln Gly Asn Thr Tyr Pro Trp Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 131

Gln Gln Gly Asn Thr Leu Pro His Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic sequence, HuMAB2 variant

<400> SEQUENCE: 132

Gln Gln Gly Asn Thr Leu Pro Tyr Thr
1               5

<210> SEQ ID NO 133
<211> LENGTH: 152
<212> TYPE: PRT
<213> ORGANISM: Mus musculus

<400> SEQUENCE: 133

Met Ser Ser Pro Gln Ser Leu Lys Thr Leu Thr Ile Thr Met Gly Trp
1               5                   10                  15

Thr Trp Ile Phe Ile Leu Ile Leu Ser Val Thr Thr Gly Val His Ser
            20                  25                  30
```

```
Glu Val Gln Leu Gln Gln Ser Gly Pro Glu Leu Glu Lys Pro Gly Ala
        35                  40                  45

Ser Val Lys Ile Ser Cys Lys Ala Ser Gly Tyr Ser Phe Thr Gly Tyr
    50                  55                  60

Asn Met Asn Trp Val Lys Gln Ser Asn Gly Lys Ser Leu Glu Trp Ile
65                  70                  75                  80

Gly Asn Ile Asp Pro Tyr Tyr Gly Gly Thr Ser Tyr Asn Gln Lys Phe
                85                  90                  95

Lys Gly Lys Ala Thr Leu Thr Val Asp Lys Ser Ser Ser Thr Ala Tyr
            100                 105                 110

Met Gln Leu Lys Ser Leu Thr Ser Glu Asp Ser Ala Val Tyr Tyr Cys
        115                 120                 125

Ala Arg Pro Gly Arg Tyr Asp Gly Ala Trp Phe Ala Tyr Trp Gly Gln
    130                 135                 140

Gly Thr Leu Val Thr Val Ser Ala
145                 150

<210> SEQ ID NO 134
<211> LENGTH: 128
<212> TYPE: PRT
<213> ORGANISM: Mus musculus

<400> SEQUENCE: 134

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Asn Val Asn Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Asp Asn Pro Leu Thr Phe Gly Ala Gly Thr Lys Leu Glu Leu Lys
        115                 120                 125

<210> SEQ ID NO 135
<211> LENGTH: 150
<212> TYPE: PRT
<213> ORGANISM: Mus musculus

<400> SEQUENCE: 135

Met Ser Ser Pro Gln Ser Leu Lys Thr Leu Thr Leu Thr Met Gly Gly
1               5                   10                  15

Ile Trp Ile Phe Leu Phe Leu Leu Ser Gly Thr Ala Gly Val His Ser
            20                  25                  30

Glu Ile Gln Leu Gln Gln Thr Gly Pro Glu Leu Val Lys Pro Gly Ala
        35                  40                  45

Ser Val Lys Ile Ser Cys Lys Ala Ser Gly Tyr Ser Phe Thr Asp Tyr
    50                  55                  60

Ile Met Leu Trp Val Lys Gln Arg His Gly Lys Ser Leu Glu Trp Ile
65                  70                  75                  80
```

Gly Asn Ile His Pro Tyr Tyr Gly Thr Thr Ser Tyr Asn Leu Lys Phe
                85              90              95

Lys Gly Lys Ala Thr Leu Thr Val Asp Lys Ser Ser Ser Thr Ala Tyr
            100             105             110

Met Gln Leu Asn Ser Leu Thr Ser Glu Asp Ser Ala Val Tyr Tyr Cys
        115             120             125

Ala Arg Gly Ile Gly Gly Ser Pro Phe Ala Tyr Trp Gly Gln Gly Thr
    130             135             140

Leu Val Thr Val Ser Ala
145             150

<210> SEQ ID NO 136
<211> LENGTH: 131
<212> TYPE: PRT
<213> ORGANISM: Mus musculus

<400> SEQUENCE: 136

Met Lys Leu Pro Val Arg Leu Leu Val Leu Met Phe Trp Ile Pro Ala
1               5               10              15

Ser Ser Ser Asp Val Leu Met Thr Gln Thr Pro Leu Ser Leu Pro Val
            20              25              30

Ser Leu Gly Asp Gln Ala Ser Ile Ser Cys Arg Ser Ser Gln Ser Ile
        35              40              45

Val His Ser Asn Gly Asn Thr Tyr Leu Glu Trp Tyr Leu Gln Lys Pro
    50              55              60

Gly Gln Ser Pro Lys Leu Leu Ile Tyr Lys Val Ser Asn Arg Phe Ser
65              70              75              80

Gly Val Pro Asp Arg Phe Thr Gly Thr Gly Ser Gly Thr Asp Phe Thr
                85              90              95

Leu Lys Ile Ser Arg Val Glu Ala Glu Asp Leu Gly Val Tyr Tyr Cys
            100             105             110

Phe Gln Gly Ser His Val Pro Tyr Thr Phe Gly Gly Gly Thr Lys Leu
        115             120             125

Glu Ile Lys
    130

<210> SEQ ID NO 137
<211> LENGTH: 5
<212> TYPE: PRT
<213> ORGANISM: Mus musculus

<400> SEQUENCE: 137

Gly Tyr Asn Met Asn
1               5

<210> SEQ ID NO 138
<211> LENGTH: 17
<212> TYPE: PRT
<213> ORGANISM: Mus musculus

<400> SEQUENCE: 138

Asn Ile Asp Pro Tyr Tyr Gly Gly Thr Ser Tyr Asn Gln Lys Phe Lys
1               5               10              15

Gly

<210> SEQ ID NO 139
<211> LENGTH: 11
<212> TYPE: PRT

```
<213> ORGANISM: Mus musculus

<400> SEQUENCE: 139

Pro Gly Arg Tyr Asp Gly Ala Trp Phe Ala Tyr
1               5                   10

<210> SEQ ID NO 140
<211> LENGTH: 10
<212> TYPE: PRT
<213> ORGANISM: Mus musculus

<400> SEQUENCE: 140

Arg Ala Ser Ser Asn Val Asn Tyr Met His
1               5                   10

<210> SEQ ID NO 141
<211> LENGTH: 7
<212> TYPE: PRT
<213> ORGANISM: Mus musculus

<400> SEQUENCE: 141

Ala Thr Ser Asn Leu Ala Ser
1               5

<210> SEQ ID NO 142
<211> LENGTH: 9
<212> TYPE: PRT
<213> ORGANISM: Mus musculus

<400> SEQUENCE: 142

Gln Gln Trp Ser Asp Asn Pro Leu Thr
1               5

<210> SEQ ID NO 143
<211> LENGTH: 5
<212> TYPE: PRT
<213> ORGANISM: Mus musculus

<400> SEQUENCE: 143

Asp Tyr Ile Met Leu
1               5

<210> SEQ ID NO 144
<211> LENGTH: 17
<212> TYPE: PRT
<213> ORGANISM: Mus musculus

<400> SEQUENCE: 144

Asn Ile His Pro Tyr Tyr Gly Thr Thr Ser Tyr Asn Leu Lys Phe Lys
1               5                   10                  15

Gly

<210> SEQ ID NO 145
<211> LENGTH: 9
<212> TYPE: PRT
<213> ORGANISM: Mus musculus

<400> SEQUENCE: 145

Gly Ile Gly Gly Ser Pro Phe Ala Tyr
1               5

<210> SEQ ID NO 146
<211> LENGTH: 16
<212> TYPE: PRT
```

<213> ORGANISM: Mus musculus

<400> SEQUENCE: 146

Arg Ser Ser Gln Ser Ile Val His Ser Asn Gly Asn Thr Tyr Leu Glu
1               5                   10                  15

<210> SEQ ID NO 147
<211> LENGTH: 7
<212> TYPE: PRT
<213> ORGANISM: Mus musculus

<400> SEQUENCE: 147

Lys Val Ser Asn Arg Phe Ser
1               5

<210> SEQ ID NO 148
<211> LENGTH: 9
<212> TYPE: PRT
<213> ORGANISM: Mus musculus

<400> SEQUENCE: 148

Phe Gln Gly Ser His Val Pro Tyr Thr
1               5

<210> SEQ ID NO 149
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 149

Ser Asp Cys Tyr Trp Thr
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic sequence, HuMAB2 variant

<400> SEQUENCE: 150

Ser Asp Cys Tyr Trp Asn
1               5

<210> SEQ ID NO 151
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 151

Tyr Thr Arg Tyr Ser Gly Ile Thr Tyr Tyr Asn Pro Ser Leu Ala Ser
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 152

Tyr Thr His Tyr Ser Gly Ile Thr Tyr Tyr Asn Pro Ser Leu Ala Ser

-continued

```
1              5              10             15
```

```
<210> SEQ ID NO 153
<211> LENGTH: 16
<212> TYPE: PRT
<213> ORGANISM: Artificial Sequence
<220> FEATURE:
<223> OTHER INFORMATION: Synthetic sequence, HuMAB2 variant

<400> SEQUENCE: 153

Tyr Thr Ile Tyr Ser Gly Ile Thr Tyr Tyr Asn Pro Ser Leu Ala Ser
1              5              10             15

<210> SEQ ID NO 154
<211> LENGTH: 11
<212> TYPE: PRT
<213> ORGANISM: Artificial Sequence
<220> FEATURE:
<223> OTHER INFORMATION: Synthetic sequence, HuMAB2 variant

<400> SEQUENCE: 154

Arg Ala Ser Gln Asp Ile Ser Tyr Tyr Leu Asn
1              5              10

<210> SEQ ID NO 155
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 155

Tyr Thr Phe Thr Leu His Ser
1              5

<210> SEQ ID NO 156
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 156

Tyr Thr Ser Gln Leu His Ser
1              5

<210> SEQ ID NO 157
<211> LENGTH: 7
<212> TYPE: PRT
<213> ORGANISM: Artificial Sequence
<220> FEATURE:
<223> OTHER INFORMATION: Synthetic sequence, HuMAB2 variant

<400> SEQUENCE: 157

Tyr Thr Ser Thr His His Ser
1              5
```